US008956866B2

(12) United States Patent
Idelson et al.

(10) Patent No.: US 8,956,866 B2
(45) Date of Patent: Feb. 17, 2015

(54) RETINAL PIGMENT EPITHELIAL CELLS DIFFERENTIATED FROM EMBRYONIC STEM CELLS WITH NICOTINAMIDE AND ACTIVIN A

(75) Inventors: Masha Idelson, MaAle Adumim (IL); Ruslana Alper-Pinus, Jerusalem (IL); Alex Obolensky, Jerusalem (IL); Eyal Banin, Jerusalem (IL); Benjamin Reubinoff, Moshav Bar-Giora-Doar-Na HaEla (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 403 days.

(21) Appl. No.: 12/450,943

(22) PCT Filed: Apr. 27, 2008

(86) PCT No.: PCT/IL2008/000556
§ 371 (c)(1),
(2), (4) Date: Oct. 19, 2009

(87) PCT Pub. No.: WO2008/129554
PCT Pub. Date: Oct. 30, 2008

(65) Prior Publication Data
US 2011/0027333 A1    Feb. 3, 2011

Related U.S. Application Data

(60) Provisional application No. 60/907,818, filed on Apr. 18, 2007.

(51) Int. Cl.
*C12N 5/02* (2006.01)
*C12N 5/079* (2010.01)
*A61K 35/44* (2006.01)
*A61K 35/48* (2006.01)
*C12N 5/074* (2010.01)

(52) U.S. Cl.
CPC ........ *C12N 5/0621* (2013.01); *C12N 2501/115* (2013.01); *C12N 2500/99* (2013.01); *C12N 5/0696* (2013.01); *C12N 2533/52* (2013.01); *C12N 2502/13* (2013.01); *A61K 35/44* (2013.01); *A61K 35/48* (2013.01); *C12N 2500/38* (2013.01); *C12N 2501/15* (2013.01); *C12N 2501/155* (2013.01); *C12N 2501/16* (2013.01); *C12N 2506/02* (2013.01)
USPC .......................... 435/377; 435/384; 435/387

(58) Field of Classification Search
CPC ............. C12N 2506/02; C12N 5/0606; C12N 2501/16; C12N 2501/115; C12N 2501/155; C12N 2533/52; C12N 5/0621; C12N 5/0696; C12N 2500/99; C12N 2501/15; C12N 2502/13
See application file for complete search history.

(56) References Cited

U.S. PATENT DOCUMENTS

| 5,843,780 A | 12/1998 | Thomson |
| 6,045,791 A | 4/2000 | Liu |
| 2009/0104695 A1* | 4/2009 | Shushan et al. ............... 435/366 |

FOREIGN PATENT DOCUMENTS

| EP | 2401794 | 1/2012 |
| GB | 2327675 | 2/1999 |
| WO | WO 94/25569 | 11/1994 |
| WO | WO 01/15544 | 3/2001 |
| WO | WO 02/060875 | 8/2002 |
| WO | WO 03/068233 | 8/2003 |
| WO | WO 2005/007011 | 1/2005 |
| WO | WO 2006/070370 | 7/2006 |
| WO | WO 2006/080952 | * 8/2006 |
| WO | WO 2008/129554 | 10/2008 |

OTHER PUBLICATIONS

Office Action Dated Sep. 27, 2011 From the Israeli Patent Office Re. Application No. 201600 and Its Translation Into English.
Translation of Office Action Dated Jan. 5, 2012 From the State Intellectual Property Office of the People's Republic of China Re. Application No. 200880020748.0.
Response Dated Nov. 17, 2011 to Office Action of Aug. 4, 2011 From the State Intellectual Property Office of the People's Republic of China Re. Application No. 200880020748.0.
Translation of Office Action Dated Aug. 4, 2011 From the State Intellectual Property Office of the People's Republic of China Re. Application No. 200880020748.0.
Communication Pursuant to Article 94(3) EPC Dated Aug. 12, 2010 From the European Patent Office Re. Application No. 08738258.6.
International Search Report and the Written Opinion Dated Aug. 20, 2008 From the International Searching Authority Re. Application No. PCT/IL2008/000556.

(Continued)

*Primary Examiner* — Deborah Crouch

(57) ABSTRACT

The present invention concerns RPE cells obtainable by directed differentiation from stem cell, particularly, human stem cells. It has been specifically found that culturing stem cells in the presence of one or more member of the TGFβ superfamily, such as Activin A) induced directed differentiation into mature and functional RPE cells. This was evidenced by the expression of markers specific to mature RPE cells, including MiTF-A, RPE65 or Bestrophin). In accordance with one particular embodiment, the cells are a priori cultured with nicotinamide (NA) which was found to augment the cells' response to the inductive effect of the one or more member of the TGFβ superfamily. The invention also provides methods of performing the directed differentiation, as well as methods for use of the resulting RPE cells.

9 Claims, 41 Drawing Sheets
(6 of 41 Drawing Sheet(s) Filed in Color)

(56) References Cited

OTHER PUBLICATIONS

Das et al. "Stem Cell Therapy for Retinal Degeneration: Retinal Neurons from Heterologous Sources", Seminars in Ophthalmology, XP002991776, 20(1): 3-10, Jan. 1, 2005. Abstract.
Haruta et al. "In Vitro and In Vivo Characterization of Pigment Epithelial Cells Differentiated from Primate Embryonic Stem Cells", Investigative Ophthalmology & Visual Science, XP002487262, 45(3): 1020-1025, Mar. 1, 2004. Abstract.
Kawasaki et al. "Generation of Dopaminergic Neurons and Pigmented Epithelia From Primate ES Cells by Stromal Cell-Derived Inducing Activity", Proc. Natl. Acad. Sci. USA, PNAS, XP002971360, 99(3): 1580-1585, Feb. 5, 2002. Abstract, p. 1580, col. 2, § 3-p. 1582, col. 1, § 2.
Kubota et al. "Transplantable Retinal Pigment Epithelial Cell Sheets for Tissue Engineering", Biomaterials, XP005365321, 27(19): 3639-3644, Jul. 1, 2006. Abstract. Abstract, p. 3642-3643.
Response Dated Feb. 10, 2011 to Communication Pursuant to Article 94(3) EPC of Aug. 12, 2010 From the European Patent Office Re. Application No. 08738258.6.
Communication Pursuant to Article 94(3) EPC Dated Oct. 29, 2012 From the European Patent Office Re. Application No. 08738258.6.
Chung et al. "Human Embryonic Stem Cell Lines Generated Without Embryo Destruction", Cell Stem Cell, XP002604696, 2(2): 113-117, Feb. 7, 2008.
Salero et al. "Adult Human RPE Can Be Activated Into a Multipotent Stem Cell That Produces Mesenchymal Derivatives", Cell Stem Cell, 10: 88-95, Jan. 6, 2012.
Communication Pursuant to Rules 70(2) and 70a(2) EPC and Reference to Rule 39(1) EPC Dated Feb. 11, 2013 From the European Patent Office Re. Application No. 12181140.0.
Office Action Dated May 14, 2012 From the Israeli Patent Office Re. Application No. 201600 and Its Translation Into English.
Translation of Office Action Dated Jul. 25, 2012 From the State Intellectual Property Office of the People's Republic of China Re. Application No. 200880020748.0.
Thomson et al. "Embryonic Stem Cell Lines Derived From Human Blastocysts", Science, 282: 1145-1147, Nov. 6, 1998.
Thomson et al. "Isolation of a Primate Embryonic Stem Cell Line", Proc. Natl. Acad. Sci. USA, 92: 7844-7848, Aug. 1995.
Patent Examination Report Dated Jan. 7, 2013 From the Australian Government, IP Australia Re. Application No. 2008242106.
European Search Report and the European Search Opinion Dated Jan. 9, 2013 From the European Patent Office Re. Application No. 12181140.0.
Communication Under Rule 71(3) EPC Dated Jun. 27, 2014 From the European Patent Office Re. Application No. 08738258.6.
Requisition by the Examiner Dated Jun. 4, 2014 From the Canadian Intellectual Property Office Re. Application No. 2,684,460.
Translation of Notice of Reason for Rejection Dated May 17, 2013 From the Japanese Patent Office Re. Application No. 2010-503665.
Examination Report Dated Jan. 30, 2014 From the Government of India, Patent Office, Intellectual Property Building Re. Application No. 6790/CHENP/2009.
Office Action Dated Jan. 30, 2014 From the Israel Patent Office Re. Application No. 225163 and Its Translation Into English.
Translation of Notification of Office Action and Search Report Dated Feb. 17, 2013 From the State Intellectual Property Office of the People's Republic of China Re. Application No. 200880020748.0.
Office Action Dated Sep. 21, 2014 From the Israel Patent Office Re. Application No. 225163 and Its Translation Into English.
Communication Pursuant to Rule 94(3) EPC Dated Jun. 13, 2014 From the European Patent Office Re. Application No. 08738258.6.
Communication Pursuant to Article 94(3) EPC Dated Jul. 4, 2013 From the European Patent Office Re. Application No. 08738258.6.
Communication Pursuant to Article 94(3) EPC Dated Sep. 13, 2013 From the European Patent Office Re. Application No. 12181140.0.
Examination Report Dated Oct. 10, 2014 From the Government of India, Patent Office, Intellectual Property Building Re. Application No. 6790/CHENP/2009.
Communication of A Notice of Opposition Dated Oct. 16, 2014 From the European Patent Office Re. Application No. 08738258.6.
Communication Pursuant to Rule 114(2) EPC Dated Oct. 22, 2014 From the European Patent Office Re. Application No. 12181140.0.
Chow et al. "Early Eye Development in Vertebrates", Annual Review of Cell and Developmental Biology, 17: 255-296, 2001.
Davis el al. "Activin A Promotes Progenitor Differentiation Into Photoreceptors in Rodent Retina", Molecular and Cellular Neuroscience, 15: 11-21, 2000.
Fuhrmann et al. "Extraocular Mesenchyme Patterns the Optic Vesicle During Early Eye Development in the Embryonic Chick", Development, 127: 4599-4609, 2000.
Klimanskaya et al. "Derive and Conquer: Sourcing and Differentiating Stem Cells for Therapeutic Applications", Nature Reviews Drug Discovery, 7: 131-142, Published Online Dec. 14, 2007.
Lamba et al. "Efficient Generation of Retinal Progenitor Cells From Human Embryonic Stem Cells", Proc. Natl. Acad. Sci. USA, PNAS, 103(34): 12769-12774, Aug. 22, 2006.
Piek et al. "Specificity, Diversity, and Regulation in TGF-Beta Superfamily Signaling", The FASEB Journal, 13: 2105-2124, Dec. 13, 1999.
Shi et al. "Mechanisms of TGF-Beta Signaling From Cell Membrane to the Nucleus", Cell, 113: 685-700, Jun. 13, 2003.
Thermo Fischer Scientific "21331—DMEM/F-12, No Glutamine, No HEPES", Life Technologies, Data Sheet, 2 P., 2014.
Thermo Fischer Scientific "41965—DMEM, High Glucose", Life Technologies, Data Sheet, 2 P., 2014.
US Patent and Trademark Office Response to Final Filed in Conjunction With RCE Dated Jul. 4, 2013 From the Re. U.S. Appl. No. 12/450,943.
Vaca et al. "Nicotinamide Induces Differentiation of Embryonic Stem Cells Into Insulin-Secreting Cells", Experimental Cell Research, 314(5): 969-974, Available Online Dec. 4, 2007.
Vugler et al. "Embryonic Stem Cells and Retinal Repair", Mechanisms of Development, 124: 807-829, Available Online Aug. 15, 2007.
Yao et al. "Long-Term Self-Renewal and Directed Differentiation of Human Embryonic Stem Cells in Chemically Defined Conditions", Proc. Natl. Acad. Sci. USA, PNAS, 103(18): 6907-6912, May 2, 2006.

* cited by examiner

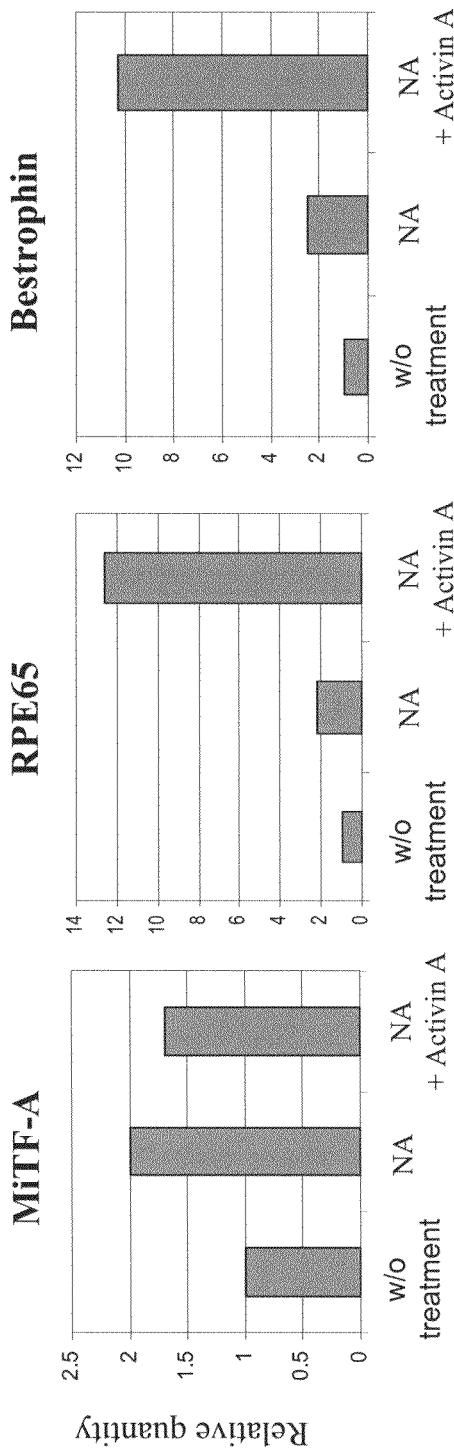

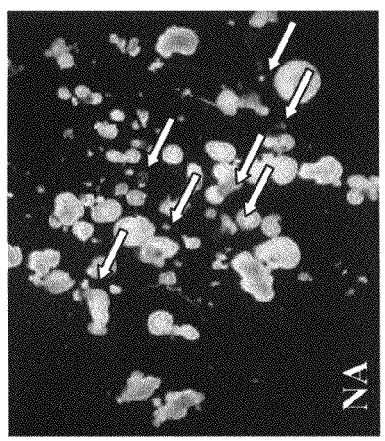
Fig. 5B NA
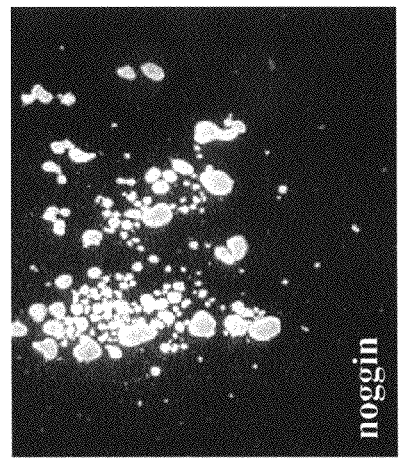
Fig 5D noggin
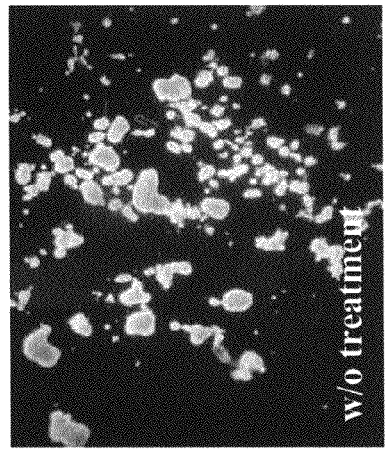
Fig. 5A w/o treatment
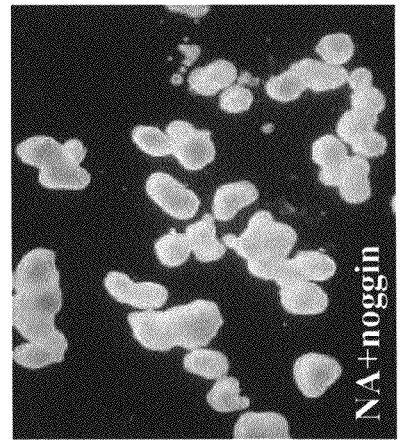
Fig 5C NA+noggin

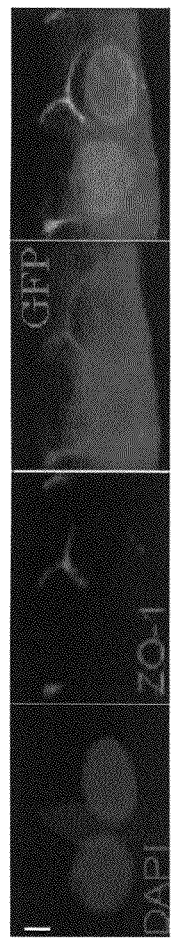
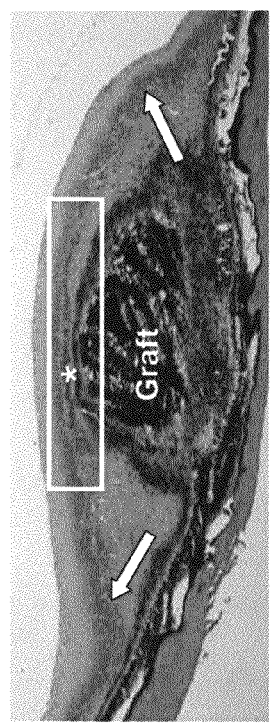
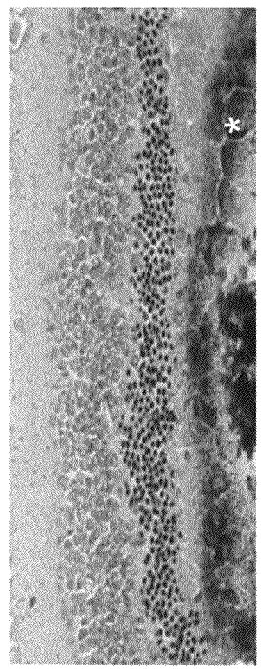
Fig. 6K  Fig. 6L  Fig. 6M  Fig. 6N
Fig. 6O
Fig. 6P

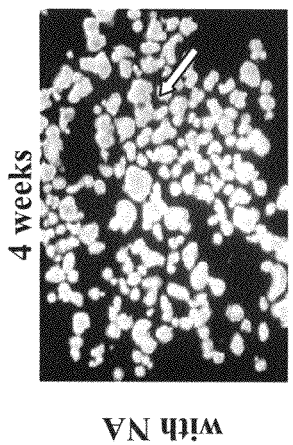
Fig. 8A (with NA, 4 weeks)
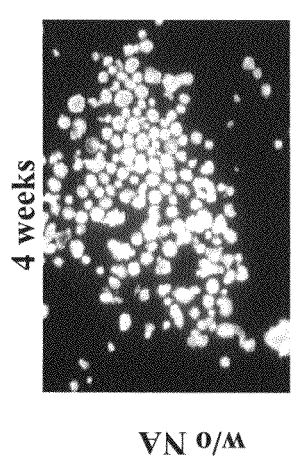
Fig. 8B (w/o NA, 4 weeks)
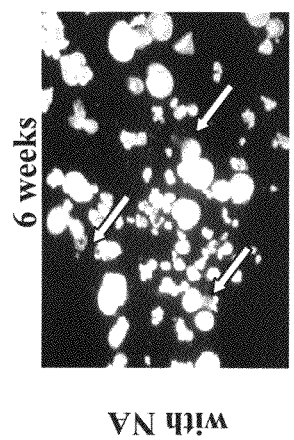
Fig. 8C (with NA, 6 weeks)
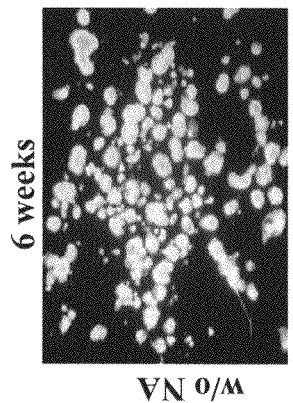
Fig. 8D (w/o NA, 6 weeks)
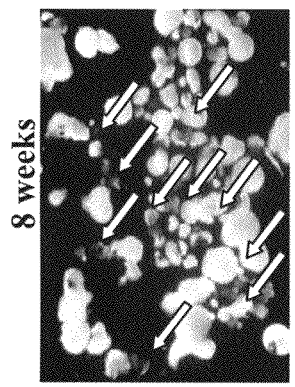
Fig. 8E (with NA, 8 weeks)
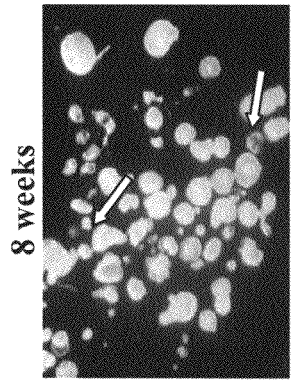
Fig. 8F (w/o NA, 8 weeks)

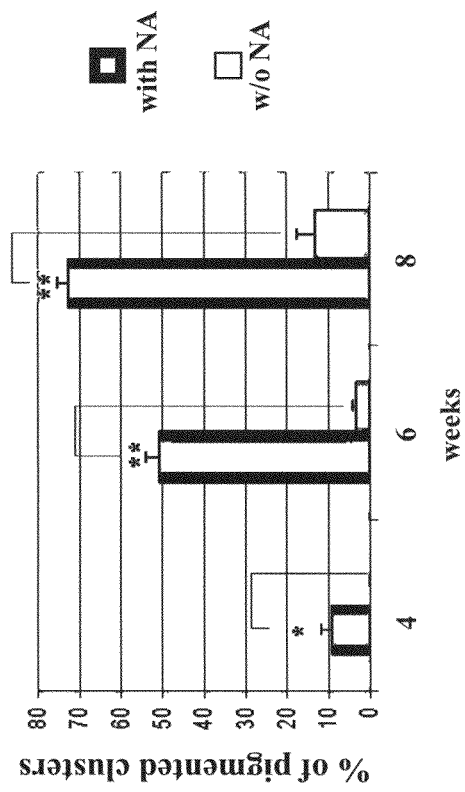
Fig. 8G
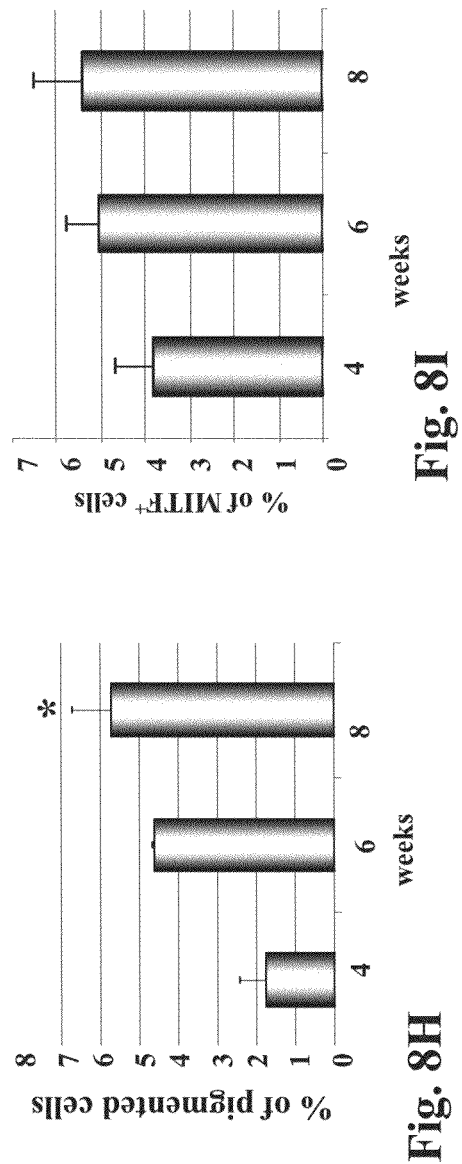
Fig. 8H
Fig. 8I

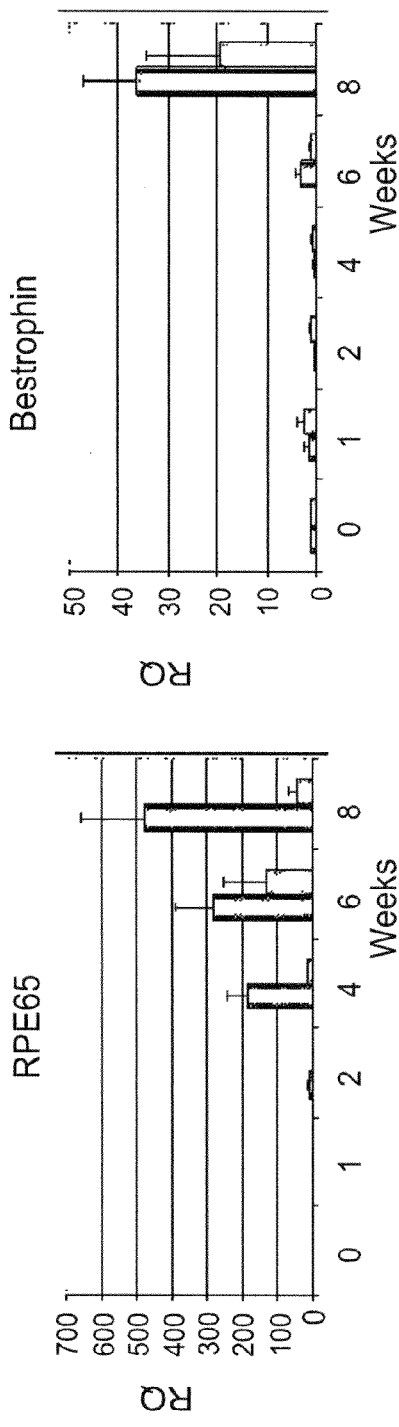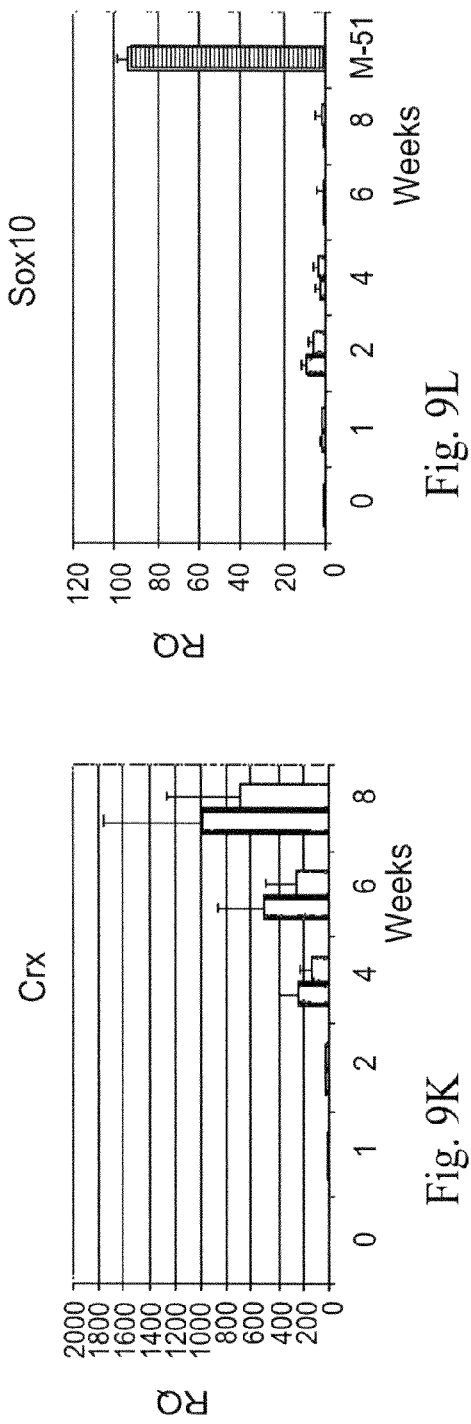
Fig. 9I  Fig. 9J  Fig. 9K  Fig. 9L

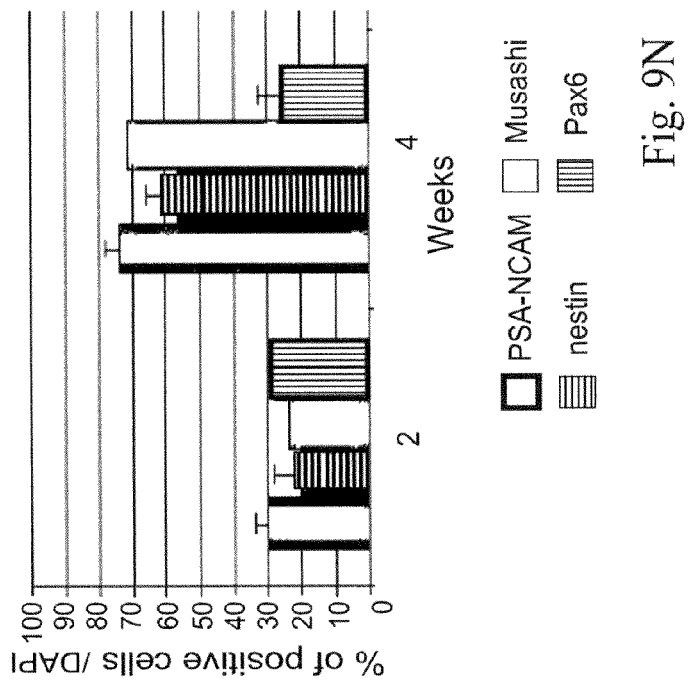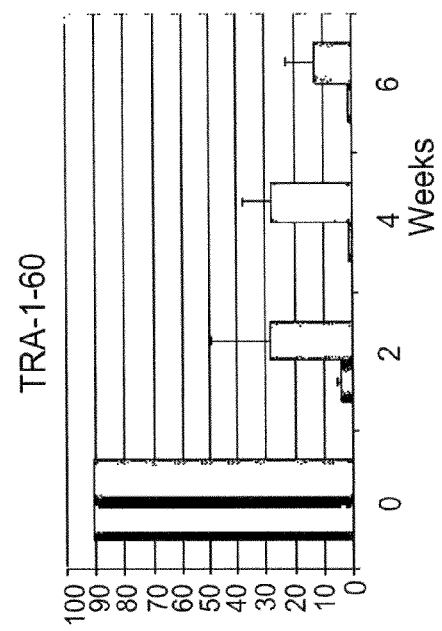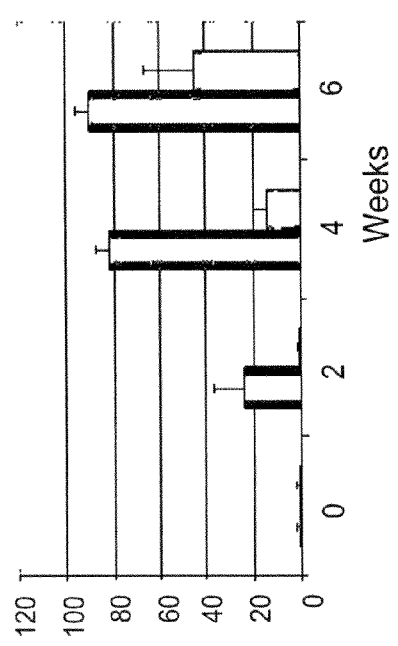

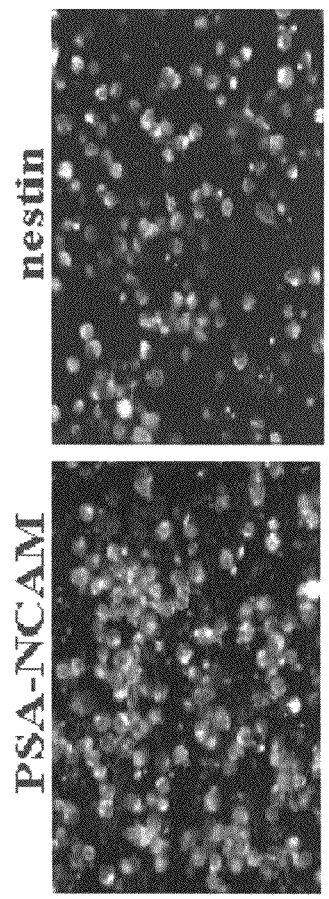
Fig. 9P PSA-NCAM
Fig. 9Q nestin
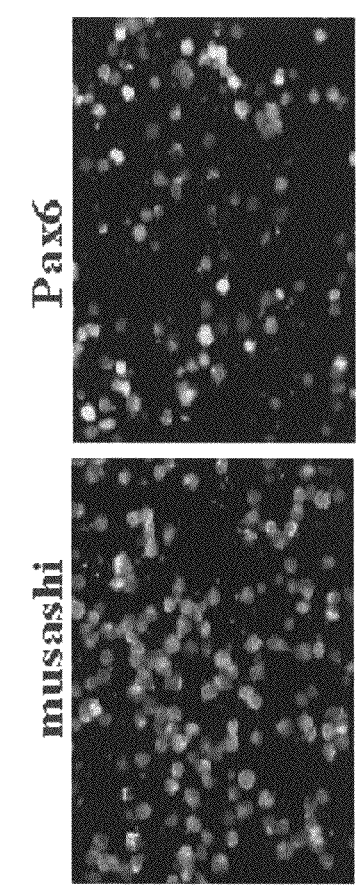
Fig. 9R musashi
Fig. 9S Pax6

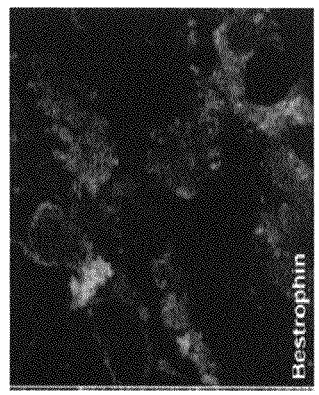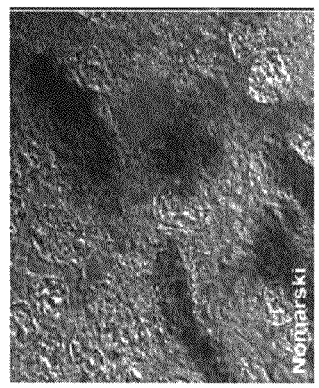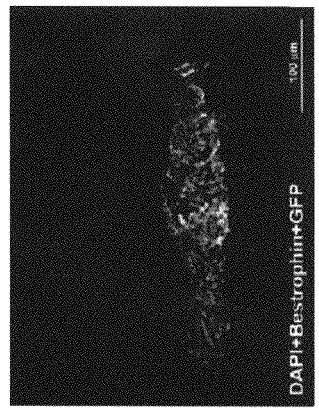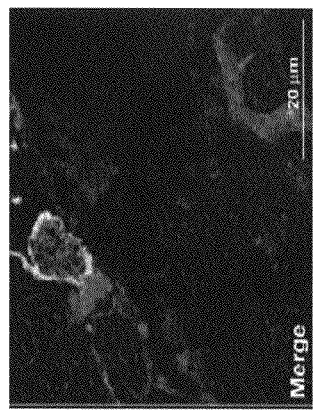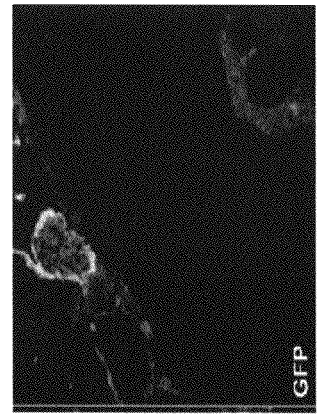

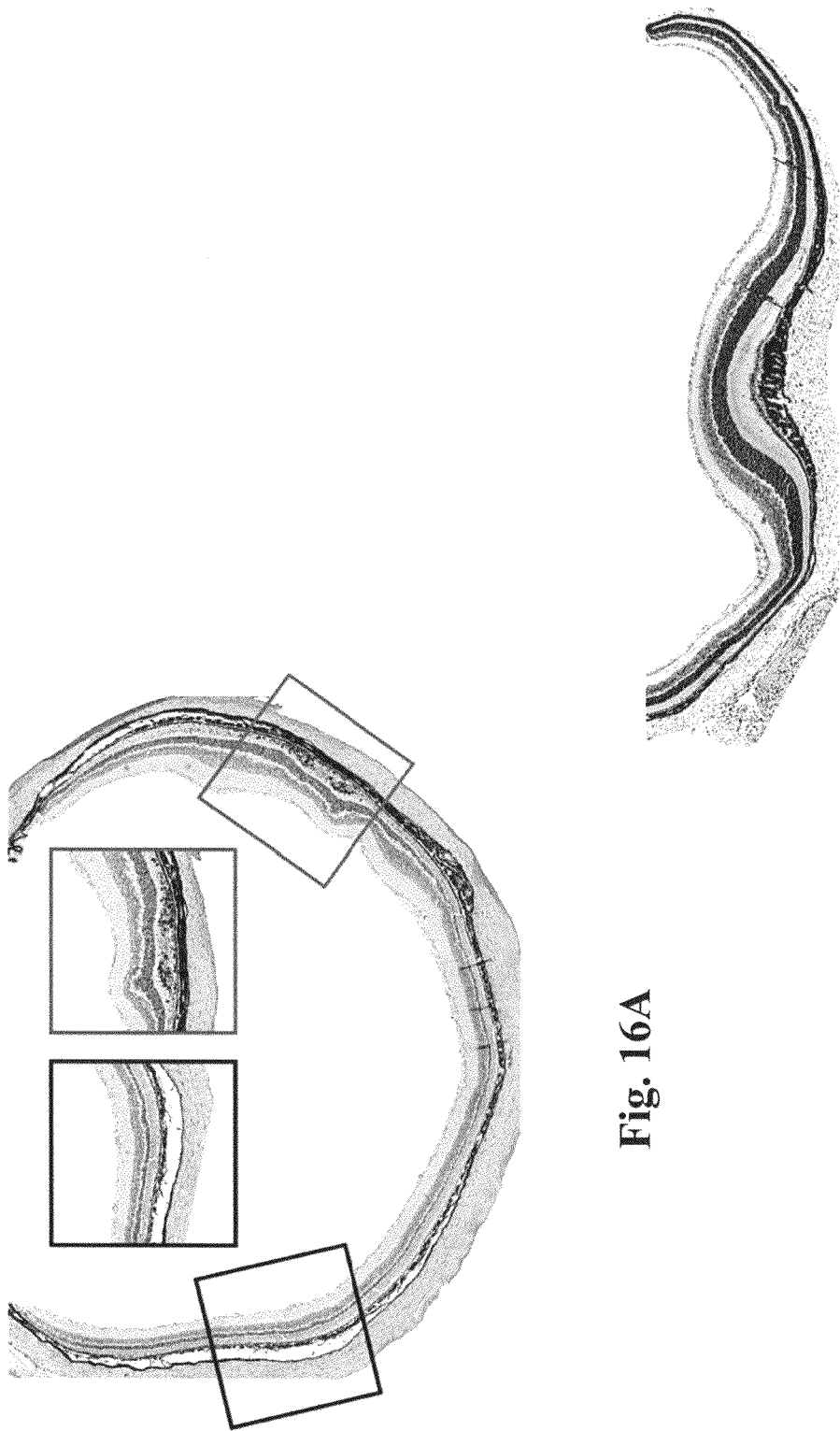
Fig. 16A
Fig. 16B

RETINAL PIGMENT EPITHELIAL CELLS DIFFERENTIATED FROM EMBRYONIC STEM CELLS WITH NICOTINAMIDE AND ACTIVIN A

RELATED APPLICATIONS

This application is a National Phase Application of PCT Patent Application No. PCT/IL2008/000556 having International Filing Date of Apr. 27, 2008, which claims priority from U.S. Provisional Patent Application No. 60/907,818, filed on Apr. 18, 2007. The contents of the above Application are all incorporated herein by reference.

FIELD OF THE INVENTION

This invention relates to methods and systems for producing differentiated retinal pigment epithelial cells (RPE) and to therapeutic uses of RPE cells obtained thereby.

LIST OF RELATED ART

The following is a list of references which are considered to be pertinent for describing the state of the art in the field of the invention.
(1) Strauss O., The retinal pigment epithelium in visual function; *Physiol. Rev.* 85: 845-881, 2005.
(2) Lund R D. et al., Cell transplantation as a treatment for retinal disease; *Prog Retin Eye Res* 20: 415-449, 2001.
(3) Haruta M., Embryonic stem cells: potential source for ocular repair; *Semin Opthalmol.* 20(1):17-23, 2005.
(4) Haruta M. et al., In vitro and in vivo characterization of pigment epithelial cells differentiated from primate embryonic stem cells; *Invest Opthalmol Vis Sci* 45:1020-1024, 2004.
(5) Aoki H. et al., Embryonic stem cells that differentiate into RPE cell precursors in vitro develop into RPE cell monolayers in vivo; *Exp Eye Res.* 82(2):265-274, 2006.
(6) Klimanskaya I. et al., Derivation and comparative assessment of retinal pigment epithelium from human embryonic stem cells using transcriptomics; *Cloning Stem Cells* 6(3): 217-245, 2004.
(7) Lund R D. et al., Human embryonic stem cell-derived cells rescue visual function in dystrophic RCS rats; *Cloning Stem Cells* 8(3):189-199, 2006.
(8) PCT application publication No. WO 06/070370.

BACKGROUND OF THE INVENTION

Dysfunction, injury, and loss of retinal pigment epithelium (RPE) cells are prominent features of certain eye diseases and disorders, such as age-related macular degeneration (AMD), hereditary macular degenerations including Best disease (the early onset form of vitelliform macular dystrophy), and subtypes of retinitis pigmentosa (RP). A potential treatment for such diseases is the transplantation of RPE (and photoreceptors) into the retina of those affected with the diseases. It is believed that replenishment of RPE cells by their transplantation may delay, halt or reverse degeneration, improve retinal function and prevent blindness stemming from such conditions.

The macula, the central part of the retina, is responsible for fine visual detail and color perception, and is crucial for many of our daily visual tasks such as facial recognition and reading. The macula is often affected as part of the disease process in widespread retinal degenerations such as retinitis pigmentosa (RP), as well as in different diseases that more specifically target the macular region such as age-related macular degeneration (AMD) and Best disease. In many of these diseases, the primary dysfunction and failure occurs in the retinal pigment epithelium (RPE) cells which underlie the photoreceptors.

The highly specialized RPE cells play a major role in supporting photoreceptor function: they actively transport nutrients from the choroidal vessels, participate in the recycling of vitamin A, which is necessary for the chromophores in the photoreceptors, and take-up and recycle shed photoreceptor outer segments as part of the normal renewal process of these cells[1].

In subtypes of RP, Best disease, and AMD, failure of the RPE ultimately leads to visual loss and blindness. Replacement of these cells is a possible therapeutic intervention[2], but obtaining such cells from human donors or embryos is difficult. Human embryonic stem cells (hESCs) may serve as a potential unlimited donor source for RPE cells, if the means to direct their differentiation into functional RPE cells can be elucidated[3]. Methods to direct the differentiation of hESCs into cultures highly enriched for neural precursor cells (NPs) have previously been described (Reubinoff B E. et al., Neural progenitors from human embryonic stem cells; *Nat Biotechnol* 19: 1134-1140, 2001; Itsykson P. et al., Derivation of neural precursors from human embryonic stem cells in the presence of noggin; *Mol Cell Neurosci.* 30(1):24-36, 2005). In addition, the potential of hESCs to give rise to retinal cells both in vitro and in vivo following transplantation to the subretinal space in rodents has been shown (Banin E. et al., Retinal Incorporation and Differentiation of Neural Precursors Derived from Human Embryonic Stem Cells; *Stem Cells* 24(2):246-257, 2006.)

The potential of mouse and non-human primate ESCs to differentiate into RPE cells, and to survive and attenuate retinal degeneration after transplantation, has been demonstrated[4,5]. Spontaneous differentiation of hESCs into RPE cells was shown, however, the efficiency of the differentiation process was low, a substantial time of differentiation was required and only a low (<1%) percentage of clusters containing RPE cells were obtained after 4-8 weeks of differentiation. Furthermore, while improved retinal function was observed in RCS rats after sub retinal transplantation of these RPE cells, function of the transplanted cells as authentic mature RPE cells was not demonstrated and this effect could potentially be related to a non-RPE-specific trophic effect.[6,7,9,10]

It was also recently shown that hESCs may be directed to reproducibly differentiate into RPE cells, in which directed rather than spontaneous differentiation of hESCs towards an RPE fate occurred in the presence of Nicotinamide (NA)[8].

SUMMARY OF THE INVENTION

In accordance with a first aspect, the present invention provides the use of a member of the transforming growth factor-β(TGFβ) superfamily for the preparation of a culture system for promoting directed and augmented differentiation of human stem cells (hSCs) into retinal pigment epithelial (RPE) cells.

In accordance with a second aspect, the present invention provides a method for promoting directed differentiation of hSCs into RPE fate, the method comprising:
 (a) providing a cell culture comprising hSCs; and
 (b) culturing cells in said cell culture in a culture system comprising a basic medium supplemented with one or more member of TGFβ superfamily whereby said hSCs are promoted towards directed differentiation into RPE fate.

In accordance with a third aspect, there is provided a cell culture comprising RPE cells obtained by directed differentiation of hSCs in the presence of one or more member of TGFβ superfamily. Preferably, the RPE cells are terminally differentiated (mature) RPE cells obtained by the method disclosed herein. As will be shown herein, such RPE cells exhibit several characteristic traits that are different from those obtained when hSCs are spontaneously differentiated into RPE cells. Preferably, the RPE cells are capable of responding to TGFβ signaling during their differentiation.

In accordance with a fourth aspect, there is provided a method of transplanting hSCs-derived RPE cells into a subject's eye, said RPE cells obtained by directed differentiation of said hSCs, the method comprises
  (a) providing a cell culture comprising hSCs;
  (b) culturing said cell culture in a culture system comprising a basic medium supplemented with one or more member of TGFβ superfamily whereby said hSCs are induced to differentiate into RPE cells;
  (c) harvesting from said cell culture RPE cells; and
  (d) transplanting said RPE cells into said subject's eye.

In accordance with a fifth aspect, there is provided a cell culture system comprising transplantable hSCs-derived RPE cells obtained by directed differentiation of said hSCs. The transplanted RPE cells exhibited one or more parameters indicative that said transplanted cells are functional within said subject eye. The functionality of the transplanted RPE cells is exhibited by their ability to uptake shed outer segments of photoreceptors in parallel to improving retinal function The hSCs in the culture system of the methods disclosed herein are differentiating hSCs, i.e. a population of hSCs essentially in an undifferentiated state, or wherein at least part of said cells have been induced to undergo initial stages of directed differentiation and at times, the majority of said cells have been induced to undergo initial stages of directed differentiation. In accordance with one embodiment, the initial stage of differentiation is achieved by a priori exposing the cells to NA although initial stages of differentiation will occur also when the undifferentiated cells are co-exposed to NA and the one or more member of the TGFβ superfamily. Without being bound to theory, it is postulated that the prior exposure to NA (prior to incubation with the one or more member of the TGFβ superfamily) primes the cells towards directed differentiation (as opposed to spontaneous differentiation) into RPE cells with specific RPE morphology, as will be further discussed below.

According to a preferred embodiment, the hSCs are human embryonic stem cells (hESCs).

According to one embodiment, the culturing of cells in a medium comprising one or more member of TGFβ superfamily is at least two days after the hSCs have initiated differentiation, directed differentiation, preferably directed by NA.

In accordance with a fifth aspect, there is provided a method of treating or preventing in a subject a retinal disease or disorder comprising dysfunction, injury, and/or loss of retinal pigment epithelium, the method comprises intraocular transplantation to said subject of hSC-derived RPE cells, the RPE cells obtained by inducing the hSCs towards directed differentiation. The transplantable RPE cells are preferably obtained by the method disclosed herein.

BRIEF DESCRIPTION OF THE DRAWINGS

In order to understand the invention and to show how it may be carried out in practice, a preferred embodiment will now be described, by way of non-limiting example only, with reference to the accompanying drawings, in which:

The patent or application file contains at least one drawing executed in color. Copies of this patent or patent application publication with color drawing(s) will be provided by the Office upon request and payment of the necessary fee.

FIGS. 4A-4E: Activin A induces RPE differentiation. Human ESCs were allowed to differentiate as free floating clusters for 6 weeks in the absence or presence of activin A which was supplemented after the first week of differentiation. Dark field micrographs of the clusters show that activin A significantly increased the percentage of clusters that included pigmented cells (FIGS. 4A, B) (white arrows mark pigmented areas within differentiating clusters and the borders of pigmented areas within some of the clusters are marked by dashed lines). In the presence of activin A the borders of the pigmented areas are more sharply demarcated from surrounding non-pigmented areas within the clusters. Furthermore, the pigmented cells are darker in the presence of activin A (FIG. 4B). At the RNA level, Real-Time PCR analysis showed that the expression of RPE65 (FIG. 4D) and Bestrophin (FIG. 4E) is significantly enhanced in the presence of activin A. The expression of MiTF-A was not altered by activin A treatment (FIG. 4C).

FIGS. 5A-5G: BMPs and TGFβ3 have a role in RPE differentiation. Human ESCs were induced to differentiate as free floating clusters for 6 weeks. Spontaneous differentiation into pigmented cells was infrequently observed (FIG. 5A) but was significantly enhanced when the medium was supplemented with NA (FIG. 5B, far-left and left dark field images; white arrows mark pigmented areas within differentiating clusters). Supplementation of the medium by noggin blocked the differentiation into pigmented cells both in the absence (FIG. 5D) and in the presence of NA (FIG. 5C). At the RNA level, Real-Time PCR analysis showed that noggin reduced the expression levels of MiTF-A both in the presence and absence of NA (FIG. 5E). When TGFβ3 was added to the culture medium during differentiation of hESC clusters in the presence of NA, it significantly augmented the expression levels of MiTF-A (FIG. 5F) but not of RPE65 (FIG. 5G).

FIGS. 8A-8I: Analysis of morphology and marker expression showing the effect of NA in inducing the development of pigmented cells from hESCs. Dark field micrographs showing the progressive appearance of pigmented cells during culturing of hESC-derived clusters for 4 weeks (FIGS. 8A, 8B), 6 weeks (FIGS. 8C, 8D) and 8 weeks (FIGS. 8E, 8F) in the presence (FIGS. 8A, 8C, and 8E) or absence of NA (FIG. 8B, 8D or 8F) (white arrows mark pigmented areas within differentiating clusters). Histogram presentation of the percentage of clusters containing pigmented areas at different time points during culture in medium supplemented with NA (bars with bold line) and in control cultures (bars with fine line) (FIG. 8G). Histogram presentation of the percentage of pigmented cells (FIG. 8H). and the cells that are immunoreactive with anti-MiTF (FIG. 8I), an early RPE marker, during 8 weeks of culture with NA supplementation Scale bars: (A) 200 μm; *p<0.05; **p<0.001.

FIGS. 9A-9S: Real-time PCR, immunostaining and flow cytometry analysis showing the progression of RPE development along time in hESC differentiating clusters. (FIG. 9A-9L) Real-time PCR, analyzing the timing of the expression of key genes in RPE development in clusters cultured in the presence (bars with bold line) or absence (bars with fine line) of NA. The progressive expression of the following markers was analyzed at sequential time points during 8 weeks differentiation of hESC-derived clusters: the hESC-specific marker, Oct4 (FIG. 9A); the early neural markers, Otx2 (FIG. 9B), Musashi (FIG. 9C) and Pax6 (FIG. 9D); the retinal progenitor markers, Six3 (FIG. 9E), Rx1 (FIG. 9F), and Chx10 (FIG. 9G); the RPE markers, MiTF-A (FIG. 9H), RPE65 (FIG. 9I) and bestrophin (FIG. 9J); the photoreceptor progenitor marker, Crx (FIG. 9K); the melanocyte developmental marker, Sox 10 (bars with horizontal stripes, FIG. 9L) (The M51 melanoma cell line is used as a control). FACS analysis demonstrating the progressive expression of the hESC-specific marker, TRA-1-60 (FIG. 9M), and the neural progenitor marker, PSA-NCAM (FIG. 9O), in clusters differentiating for 8 weeks in the presence bars with (bold line) or absence (bars with fine line) of NA. Indirect immunofluorescence analysis of the percentage of cells expressing the early neural markers: PSA-NCAM (bars with bold line), nestin (bars with horizontal stripes), Musashi (bars with fine line), Pax6 (bars with vertical stripes), within the clusters differentiating for 2 and 4 weeks in the presence of NA (FIG. 9N). Immunofluorescence images, demonstrating the cells expressing these markers, PSA-NCAM (FIG. 9P), nestin (FIG. 9Q), musashi (FIG. 9R), Pax6 (FIG. 9S).

FIGS. 14A, 14F and 14K show low-magnification fluorescent image of grafts co-expressing GFP and the relevant marker. High magnification confocal images in each row show pigment (by Nomarski optics) as well as co-expression of GFP and the different markers at the single-cell level. These series confirm that the cells are indeed hESC-derived and that they express markers of mature RPE in-vivo.

FIG. 15C shows the marked difference in mean amplitudes between transplanted eyes and the different groups of control eyes (-◆- injected eye (n=13); -■- non injected eye (n=13); --▢-- medium non-injected eyes (n=5); -▲- medium injected eye (n=5)). As shown, there is a trend towards better preservation of retinal function following transplantation of activin-A treated RPE cells (shown here) as compared to the rescue effect achieved following transplantation of RPE cells derived without activin-A (FIG. 7).

FIG. 16A-16D: Transplanted hESC-derived, Activin-A treated RPE cells provide structural rescue in the RCS rat retinal degeneration model. The effects of transplanted hESC-derived, activin-treated RPE cells on the degenerating host retina were examined and quantified using high resolution microscopic images of hematoxylin and eosin stained sections. Relative preservation of the outer nuclear (photoreceptor) layer (ONL) and of the inner and outer photoreceptor segments (IS+OS) was observed in proximity to sub-retinal RPE grafts as compared with areas distant from the grafts (two examples shown in FIGS. 16A, 16B). Inserts in FIG. 16A demonstrate this difference (rescued retina with relatively thick ONL shown in right insert in proximity to graft; severe thinning of the ONL is seen in left insert, distant from the graft). Total retinal thickness (FIG. 16C) as well as ONL and IS+OS thickness (FIG. 16D) were significantly increased in vicinity to hESC-derived RPE grafts (black bars, mean±SEM, n=7) as compared to areas distant from grafts (gray bars). This type of structural rescue was observed only in proximity to sub-retinal and deep intra-retinal grafts, and not when grafts were exclusively intra-vitreal (not shown). For details of quantification technique, please see methods.

DETAILED DESCRIPTION OF THE INVENTION

Figure 1B:
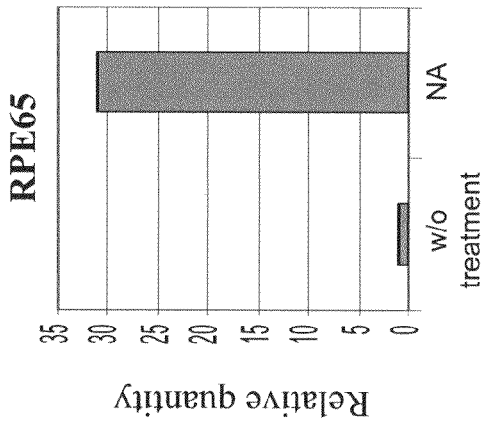
FIGS. 1A-1E: Real-Time PCR, analyzing the expression of RPE markers in the presence of NA. Differentiation of hESCs was induced by culturing them as free floating clusters. At 6 weeks of differentiation, the level of expression of the RPE markers MiTF-A (FIG. 1A) and RPE65 (FIG. 1B) was significantly enhanced in the presence of NA. Real-Time PCR analysis at sequential time points demonstrated the progressive increase in the expression levels of MiTF-A (FIG. 1C) and RPE65 (FIG. 1D) along time in the presence of NA. Expression of additional transcripts of RPE markers including Bestrophin, CRALBP and Mertk were demonstrated by RT-PCR analysis of plated pigmented clusters (FIG. 1E). +/− indicates presence or absence, respectively, of reverse transcriptase.

The present disclosure provides the use of one or more members of the transforming growth factor-β (TGFβ) superfamily for the preparation of a culture system for promoting differentiation of human stem cells (hSCs), preferably human embryonic stem cells (hESCs) into retinal pigment epithelial (RPE) cells. It should be noted that in addition to the specified uses discussed in detailed herein, also encompassed within the present disclosure are RPE cells obtained by directed differentiation of hSCs in the presence of one or more the TGFβ superfamily; as well as a method for promoting directed differentiation of hSCs into RPE fate, as well as methods for growing and maintaining such hSCs-derived RPE cells and methods making use of such hSCs-derived RPE cells. In accordance with some preferred embodiments, the RPE cells obtained according to the teaching herein are mature (in other words, terminally differentiated) and functional RPE cells, as will be further discussed and explained below.

The present disclosure broadly concerns the use of one or more members of the TGFβ superfamily of growth factors in promoting/inducing/augmenting the directed differentiation of hSCs into RPE cells, preferably mature RPE cells.

In the following description and claims use will be made, at times, with a variety of terms, and the meaning of such terms as they should be construed in accordance with the present teaching is as follows:

GLOSSARY

"Transforming growth factor-β(TGFβ superfamily growth factor", as used herein, denotes any member of the TGFβ superfamily of growth factors, such as transforming growth factor-β proteins, including the TGFβ1, TGFβ2, and TGFβ3 subtypes, as well as homologous ligands including activin (e.g., activin A, activin B, and activin AB), nodal, anti-mullerian hormone (AMH), some bone morphogenetic proteins (BMP), e.g. BMP2, BMP3, BMP4, BMP5, BMP6, and BMP7, and growth and differentiation factors (GDF).

"Human stem cells" or "hSCs", as used herein, refers to cells of human origin which under suitable conditions are capable of differentiating into other cell types having a particular, specialized function while under other suitable conditions are capable of self renewing and remaining in an undifferentiated pluripotential state as detailed below.

A "cell" as used herein refers to a single cell as well as to a population of (i.e. more than one) cells. The population may be a pure population comprising one cell type. Alternatively, the population may comprise more than one cell type. The hSCs cells are preferably hematopoietic or mesenchymal stem cells obtained from bone marrow tissue of an individual at any age or from cord blood or tissue of a newborn individual, neural stem cells obtained from fetal, any age post birth, or cadaver brain, embryonic stem (ES) cells obtained from the embryonic tissue formed after fertilization (e.g., blastomere, blastocyst), or embryonic germ (EG) cells obtained from the genital tissue of a fetus any time during gestation, preferably before 10 weeks of gestation. The term cell may denote a single cell or a cluster of cells.

"Embryonic stem cell" and "Pluripotent embryonic stem cell", as used herein, refer to a cell which can give rise to any differentiated cell types in an embryo or an adult, including the germ cells (sperm and eggs).

"Cell culture" or "Cultured cell", as used herein, refer to cells or tissues that are cultured, cultivated or grown in an artificial, in vitro environment.

"Undifferentiated pluripotential hSCs", "Pluripotent hSCs" as used herein, refer to precursor cells of human source that have the ability to form any adult cell. Such cells are true cell lines in that they: (i) are capable of extensive proliferation in vitro in an undifferentiated state; and (ii) are capable of differentiation to derivatives of all three embryonic germ layers (endoderm, mesoderm, and ectoderm) even after prolonged culture. hESCs are derived from fertilized embryos that are less than one week old (in the cleavage or blastocyte stage) or produced by artificial means (such as by nuclear transfer) that have equivalent characteristics. Other pluripotent hSCs include, without being limited thereto, multipotent adult progenitor cells (MAPs), induced pluripotent stem cells (iPS cells) and amniotic fluid stem cells.

"Undifferentiated", as used herein, refers to cultured cells when a substantial proportion (at least 20%, and possibly over 50% or 80%) of the cells and their derivatives in the population display characteristic markers and morphological characteristics of undifferentiated cells, distinguishing them from differentiated cells of embryo or adult origin. Cells are recognized as proliferating in an undifferentiated state when they go through at least 1 population doubling during a cultivation period of at least 3 weeks, while retaining at least about 50%, or the same proportion of cells bearing characteristic markers or morphological characteristics of undifferentiated cells after said cultivation period.

"Cell suspension" or "freely floating cells" as used herein, refers to a culture of cells in which the majority of the cells freely float in the medium, typically a culture medium (system), and the cells floating as single cells, as cell clusters and/or as cell aggregates. In other words, the cells survive and propagate in the medium without being attached to a substrate.

"Culture system", as used herein, refers to a culture system suitable for the propagation of SCs. The term denotes a combination of elements, at minimum including a basic medium (a cell culture medium usually comprising a defined base solution, which includes salts, sugars and amino acids) and the one or more member of a the transforming growth factor-β (TGFβ) superfamily of growth factors. The culture system in accordance with the invention may further comprise other elements such as, without being limited thereto, a serum or serum replacement, a culture (nutrient) medium and other exogenously added factors, which together provide suitable conditions that support SC growth as well as other components typically used in cell culture systems. The above elements may be collectively classified as soluble elements. However, in the context of the present invention, the elements may also be associated to a carrier, i.e. non-soluble elements. The association may be by chemical or physical attachment/binding. For example, the element may be immobilized onto a matrix (e.g. extracellular matrix), presented by cells added to the system or bound to biodegradable material. Further, the element may be released from a carrier, the carrier may be a cell or a vesicle encapsulating or embedding the element. Thus, in the following text, elements supplementing the basic media to form the culture system comprise both soluble and non-soluble elements.

"Differentiation", as used herein, refers to the process of switching the state of a cell from one cell type to another, and more specifically in the context of the present disclosure indicates the process of a human stem cell acquiring the cell type of a retinal pigment epithelial (RPE) cell with at least one characteristic feature indicative that said RPE cell is a mature (terminally differentiated) cell. As used herein, the term "cell type" refers to a distinct morphological or functional form of a cell.

"Differentiating hSCs" as used herein, refer to undifferentiated hSCs which under suitable conditions are capable of differentiating in an augmented, directed fashion into a predetermined fate; the term also referring to a population of hSCs in which at least part thereof has already been induced to undergo at least initial differentiation, namely directed differentiation or combination of same.

"Prime", "augment" "promote" or "direct", as used herein interchangeably unless the context dictates otherwise, refer to initiating non-spontaneous differentiation of stem cells into RPE cells.

"Differentiation inducer" or "differentiation promoter", "differentiation priming agent" or "differentiation promoting factor" as interchangeably used herein denotes any agent which is capable of priming, augmenting, promoting or directing differentiation of pluripotent SCs into a somatic cell, preferably, into RPE cells.

"Retinal pigment epithelial cells", "RPE cells", "RPEs", which may be used interchangeably as the context allows, mean cells of a cell type functionally similar to that of native RPE cells which form the pigmented cell layer of the retina (e.g. upon transplantation within an eye, they exhibit functional activities similar to those of native RPE cells). Thus, the terms "retinal pigment epithelial cells", "RPE cells", or "RPEs" may be used to refer to both native RPE cells of the pigmented layer of the retina and RPE cells directly differentiated from hSCs, in accordance with the present disclosure.

The term "hSC-derived RPE cells" is used herein to denote RPE cells that are obtained by directed differentiation from hSCs. In accordance with a preferred embodiment, the hSC-derived RPE cells are mature (terminally differentiated) and functional RPE cells as exhibited by parameters defined hereinbelow. The term "directed differentiation" is used interchangeably with the term "RPE induced differentiation" and is to be understood as meaning the process of manipulating hSCs under culture conditions which induce/promote differentiation into RPE cell type only.

"Functional RPE cells" is used herein to denote cells obtained by directed differentiation of hSCs in the presence of one or more members of the TGFβ superfamily, the RPE cells exhibiting at least one of the following characteristics:

during differentiation, the cultured cells respond to TGFβ signaling;

the RPE cells are mature, terminally differentiated cells as exhibited by the expression of markers indicative of terminal differentiation, e.g. bestrophin or RPE65 as well or alternatively, by their lack of potency to proliferate in vivo.

following transplantation (i.e. in situ), the RPE cells exhibit trophic effect supporting photoreceptors adjacent to RPE cells;

further, in situ the RPE cells are capable of functioning with phagocytosis of shed photoreceptor outer segments as part of the normal renewal process of these photoreceptors.

Thus, the RPE cells in accordance with the present invention are especially suitable for regeneration of host RPE thereby providing improved vision following transplantation therewith into a subject's eye.

"Similar", when used in the context of differentiated RPE cells, means that the differentiated RPE cells share one or more distinct morphological or functional features with native RPE cells. For example, sufficient similarity might be indicated by, for example, determining that the differentiated cell expresses one or more markers of naturally occurring RPE cells, such as MiTF, ZO-1, Bestrophin, RPE65, Otx2, Mertk, and CRALBP; or that the cell manifests one or more physical morphological features of RPE cells, such as typical F-actin distribution within the cells, pigmentation by pigmented granules, polygonal (e.g., hexagonal) shape, a cobblestone-like appearance and ultrastructural features of RPE as demonstrated by electron microscopy. In addition, may include any one of the functions listed above, e.g., trophic effect supporting photoreceptors adjacent to RPE cells; functionality with phagocytosis of shed photoreceptor outer segments that harbor rhodopsin or lack of potency to proliferate in vivo.

"Large scale", as used herein with regard to cell cultivation and expansion, refers to the production of RPE cells under conditions which permit at least the doubling of cells in the cell culture after 4 weeks, the cell population after the 4 weeks consisting essentially of RPE cells.

"Cell marker", as used herein, refers to any phenotypic feature of a cell that can be used to characterize it or discriminate it from other cell types. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Associated with each marker is the gene that encodes the transcript, and the events that lead to marker expression. A marker is said to be preferentially expressed in an undifferentiated or differentiated cell population, if it is expressed at a level that is at least 50% higher (in terms of total gene product measured in an antibody or PCR assay) or 30% more frequently (in terms of positive cells in the population) than an acceptable control such as actin or glyceraldehyde 3-phosphate dehydrogenase (GAPDH). Markers that are expressed 2, 10, 100, or 10,000 times higher or more frequently are increasingly more preferred.

The present disclosure makes use of hSCs from which RPE are derived, due to inductive and directed differentiation of the hSCs in the presence of a unique culture system applied to the hSCs in suspension.

Non-limiting examples of hSCs are neural stem cells obtained from the fetus, or at any age post birth or from cadaver, hematopoietic stem cells obtained from bone marrow tissue of a human individual at any age or from cord blood of a newborn individual, mesenchymal stem cells, amniotic fluid stem cells, embryonic stem (ES) cells obtained from the embryonic tissue formed after fertilization (e.g., from a single blastomere, or from blastocyst), embryonic germ (EG) cells obtained from the genital tissue of a fetus any time during gestation, preferably before 10 weeks of gestation, induced pluripotent stem cells, or stem cells obtained from the gonads of human individual at any age. Preferred human stem cells according to the present invention are human embryonic stem cells (hESC).

hSCs can be obtained using well-known cell-culture methods. For example, hESC can be isolated from single blastomeres of the cleavage or morula stage human embryo, from cleavage stage and morula human embryos and human blastocysts. Human embryos may be obtained from in vivo pre-implantation embryos or more typically from in vitro fertilized (IVF) embryos. Alternatively, non-fertilized human oocyte can be parthenogenetically activated to cleave and develop to the blastocyst stage. In addition a single cell human embryo can be expanded to the blastocyst stage. For the isolation of hESCs from a blastocyst, the zona pellucida is removed and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by mechanical dissociation or by enzymatic digestion and the cells are then re-plated on a fresh tissue culture medium. Colonies demonstrating undifferentiated morphology are individually selected by micropipette, mechanically dissociated into clumps, and re-plated. Resulting ESCs are then routinely split every 1-2 weeks. For further details on methods of preparation of hESCs see Thomson et al. [U.S. Pat. No. 5,843,780; Science 282:1145, 1998; Curr. Top. Dev. Biol. 38:133, 1998; Proc. Natl. Acad. Sci. USA 92: 7844, 1995]; Bongso et al. [Hum Reprod 4: 706, 1989].

Commercially available hSCs can be also used in accordance with the invention. HSCs can be purchased from the NIH human embryonic stem cells registry. Non-limiting examples of commercially available embryonic stem cell lines are BG01, BG02, BG03, BG04, CY12, CY30, CY92, CY10, TE03 and TE32.

Potential applications of hESC and cells derived from them are far ranging and include drug discovery and testing, generation of cells, tissues and organs for use in transplantation, production of biomolecules, testing the toxicity and/or teratogenicity of compounds, high through put screening of molecules for their toxic, regenerative, protective or any other effect, and facilitating the study of developmental and other biological processes. For example, diseases presently expected to be treatable by therapeutic transplantation of hESC or hESC-derived cells include Parkinson's disease, cardiac infarcts, juvenile-onset diabetes mellitus, and leukemia [Gearhart J. *Science* 282: 1061-1062, 1998; Rossant and Nagy, *Nature Biotech.* 17: 23-24, 1999].

There are, however, significant hurdles to the practical exploitation of hESC. Two such hurdles include: maintaining hESC in an undifferentiated, pluripotential state without spontaneous differentiation; and directing the differentiation of hESC into specific types of somatic cells. Several culture systems have been described for maintaining and propagating stem cells, and particularly hESC, in an undifferentiated state[8].

Because of the potential of differentiated cells derived from stem cells in countless therapeutic applications, directing or promoting the differentiation of stem cells in culture toward a specific somatic cell fate is of great interest.

In certain eye diseases and disorders of, e.g., the retina and the macula, failure of RPE cells ultimately leads to visual loss and even blindness. Transplantation of RPE cells to replace and support the failing host RPE has been suggested as a possible therapeutic intervention, but obtaining such cells from human donors or embryos is difficult. hSCs thus may serve as a potential unlimited donor source for RPE cells, if the means to direct their differentiation into functional RPE cells can be elucidated.

It has now been surprisingly found that contacting hSCs with a member of the TGFβ superfamily of growth factors strongly promotes differentiation of hSCs towards an RPE fate. In other words, these growth factors have an inducting effect on the hSCs. Thus, the use of member/members of the transforming growth factor-β (TGFβ) superfamily for the preparation of a culture system for inducing differentiation of human stem cells (hSCs) into retinal pigment epithelial (RPE) cells, has thus been envisaged.

While many members of the TGFβ superfamily of growth factors are known (some non-limiting examples being listed above), according to a preferred embodiment, the member of the TGFβ superfamily is preferably the TGFβ1, TGFβ3 growth factors or activin A or a combination of same.

It was previously found that nicotinamide (NA) in a cell culture has an inhibitory effect on differentiation of stem cells into extraembryonic cells, and further that NA promotes somatic differentiation toward neural and further toward an RPE cell-like fate[8]. NA, also known as "niacinamide", is the amide derivative form of Vitamin B3 (niacin) which is thought to preserve and improve beta cell function. NA has the chemical formula $C_6H_6N_2O$, NA is essential for growth and the conversion of foods to energy, and it has been used in arthritis treatment and diabetes treatment and prevention.

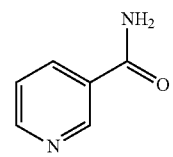

Nicotinamide (NA)

In the context of the present disclosure, the term NA also denotes derivatives of NA.

The term "derivative of nicotinamide (NA)" as used herein denotes a compound which is a chemically modified derivative of the natural NA. The chemical modification may include, for example, a substitution on the pyridine ring of the basic NA structure (via the carbon or nitrogen member of the ring), via the nitrogen or the oxygen atoms of the amide moiety, as well as deletion or replacement of a group, e.g. to form a thiobenzamide analog of NA, all of which being as appreciated by those versed in organic chemistry. The derivative in the context of the invention also includes the nucleoside derivative of NA (e.g. nicotinamide adenine). A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives (WO05/014549).

In connection with the above it has now been surprisingly found that when hSCs are differentiating in the presence of NA, their properties are altered and accordingly they gain the capability to respond to an inductive effect of one or more members of the TGFβ superfamily which directs their differentiation towards RPE fate, preferably mature and functional RPE cells. Hence the RPE differentiation-inductive effect of NA may be significantly enhanced when thereafter exposing the hSCs to the one or more member of the TGFβ superfamily of growth factors in combination with the pre-exposure of the cells in the culture to NA.

Thus, according to one embodiment the method comprises treating the cells with the one or more member of the TGFβ superfamily of growth factors is used in combination with prior exposure to NA. Combination may be for the preparation of a culture system comprising both TGFβ and NA; as well as for the preparation of a culture system comprising only the one or more member of the TGFβ superfamily, to be used for inducing/promoting differentiation and/or further differentiation of hSCs which have already been exposed to NA. Without being bound to theory, it is believed that NA acts as a differentiation inducer/promoter and that similarly, the one or more members of the TGFβ superfamily act as an RPE differentiation promoting factor. In addition, while not being bound by theory, it is believed that the prior exposure of the hSCs to NA provides the cells with properties that enable their response to the RPE differentiation promoting effect of the one or more members of the TGFβ superfamily.

Thus, in accordance with an embodiment of the invention, the hSCs are first cultured in a culture system comprising a basic medium supplemented with NA for at least several hours, preferably at least a day and more preferably, at least two days prior to culturing the cells in that cell culture in a basic medium (the same or different) supplemented with the one or more member of TGFβ superfamily.

In accordance with another embodiment, the undifferentiated hSCs are cultured in a culture system comprising a basic medium supplemented with NA and the one or more member of TGFβ superfamily.

It is noted that various basic mediums are known in the art for use in cell cultures and preferably for use in SC cultures. A non-limiting list of basic mediums which can be used in accordance with the present disclosure comprises Neurobasal™ (CAT#21103-049, Gibco 1998/1999), KO-DMEM (CAT#10829-018, Gibco 1998/1999), DMEM (CAT#41965-039, Gibco 2004), DMEM/F12 (CAT#21331-020, Gibco 2004), Cellgro™ Stem Cell Growth Medium (CAT#2001, CellGenix 2005), or X-Vivo™ (CAT#04-380Q, LONZA 2007).

The present disclosure also provides a method for inducing directed differentiation of hSCs into RPE fate, the method comprising:
(a) providing cell culture comprising hSCs;
(b) culturing cells in said cell culture in a culture system comprising a basic medium supplemented with one or more members of the TGFβ superfamily whereby directed differentiation of the hSCs into RPE fate is promoted.

Differentiation may occur within free floating clusters of hSCs or adherent cultures. Somatic differentiation within adherent cultures was described [U.S. Pat. No. 7,112,437]. Such adherent cultures may thus serve as a basis for inducing RPE differentiation by a culture system supplemented with at least one or more members of the TGFβ superfamily of growth factors.

The cells in the cell culture may be a population of undifferentiated hSCs or a population of cells in which at least part of the hSCs have initiated differentiation. The initial differentiation is a directed differentiation. Thus, in the context of the disclosure, the cells provided in the method are at times referred to as differentiating cells.

As already indicated above, the basic medium may be supplemented by the introduction thereto of soluble elements as well as by non-soluble elements. With respect to the supplementation with one or more members of the TGFβ superfamily of growth factors, the member may be presented in soluble form or affixed or associated to a matrix or cell added to the culture system or the element may be bound or complexed to other substances. The member may also be secreted to the culture system from cells present in the latter.

The hSCs may be provided in undifferentiated state as well as after being exposed to a differentiation promoting factor (differentiation priming agent), such as NA. Undifferentiated hSCs may be obtained from various culture systems in which hSCs may be maintained in an undifferentiated pluripotent state. For example, the cells may be cultivated in a feeder-free adherent or suspension system (WO06/070370) or on feeder cells. Commonly used feeder cells include a primary mouse embryonic fibroblast (PMEF), a mouse embryonic fibroblast (MEF), a murine fetal fibroblast (MFF), a human embryonic fibroblast (HEF), a human fibroblast obtained from the differentiation of human embryonic stem cells, a human fetal muscle cell (HFM), a human fetal skin cell (HFS), a human adult skin cell, a human foreskin fibroblast (HFF), a human cell obtained from the umbilical cord or placenta, a human adult fallopian tubal epithelial cell (HAFT) and human marrow stromal cells (hMSCs). The clusters of hSCs may be obtained from an adherent cell culture by dissociation of the cells from the feeder layer or extracellular matrix to form a suspension of cells. The suspension of cells may comprise the free floating clusters or an essentially single cell suspension from which clusters of cells are outgrown to form the cell clusters.

In accordance with a preferred embodiment, the cell culture comprises cell suspension, preferably free floating clusters in a suspension culture, i.e. aggregates of cells derived from human embryonic stem cells (hESCs). Sources of free floating stem cells were previously described in WO 06/070370, which is herein incorporated by reference in its entirety.

The culturing step in accordance with the present disclosure may comprise cultivation of the cells in the cell culture with one or more different culture systems, at least one of the culture systems comprising the one or more member of the TGFβ superfamily.

In accordance with one embodiment of the present disclosure, the cells in the culture are cultivated in a culture system comprising a basic medium supplemented with NA, in addition to said one or more member of TGFβ superfamily of growth factors.

In accordance with another embodiment, the cells are firstly cultured in a culture system comprising a basic medium and NA, the cells being undifferentiated hSCs, and preferably after hSCs differentiation is induced (i.e. after a predetermined time period or after confirming cell differentiation by techniques available in the art) the cells in the cell culture are cultured in a culture system comprising the one or more member of TGFβ superfamily of growth factors. The second culture system may also comprise NA, i.e. may be the same as the initial culture system, into which the member of the TGFβ superfamily is added. As a result, directed differentiation into RPE cells is induced.

In accordance with this embodiment, the hSCs in the initial cell culture are cultured in the NA comprising culture system for at least the time period required for hSCs differentiation to initiate. In accordance with one particular embodiment, the cell culture system is cultivated in the NA comprising culture system for several days, preferably at least two days and preferably for at least one week, more preferably, at least two weeks.

Without being bound by theory, it is stipulated by the inventors that NA induces the directed differentiation process which is also accelerated in its progression as compared to spontaneous differentiation (namely, that occurring in the absence of NA exposure or exposure to NA in combination with TGFβ member). It has been shown herein that in the directed differentiation, undifferentiated stem cells are more rapidly eliminated from the culture system. Hence, NA is used in a culture system of differentiating hSCs as a mean to promote and accelerate the directed differentiation process, and for the complete elimination of undifferentiated stem cells by thus preventing potential complications such as teratoma tumor formation from the presence of undifferentiated cells after transplantation.

It has been shown herein that exposure of the hSCs to NA followed by exposure to one or more member of the TGFβ superfamily induces differentiation into cells with a different phenotype as compared to spontaneously differentiating cells (i.e. in the absence of these factors).

Further, without being bound by theory, it is assumed by the inventors that NA induces differentiation into cells that express receptors to one or more member of the TGFβ superfamily (which are not expressed by spontaneously differentiating stem cells), thereby allowing directed differentiation into mature and functional RPE cells. Such receptor expression allows the inductive effect of the TGFβ superfamily member on directed differentiation of the differentiating cells in the culture towards RPE fate, namely, towards mature and functional RPE cells.

As indicated above, there is a variety of members of the TGFβ superfamily of growth factors. For example, the growth factor in accordance with the invention may be one or more of the following TGFβ1, TGFβ2, TGFβ3, activin A, activin B, activin AB, nodal, anti-mullerian hormone (AMH), BMP3, BMP4, BMP5, BMP6, BMP7 or growth and differentiation factor (GDF). However, preferably, the growth factor of the TGFβ superfamily is TGFβ3 or TGFβ1 or activin A or the combination of same.

The basic medium in accordance with the invention is any known cell culture medium known in the art for supporting cells growth in vitro, typically, a medium comprising a defined base solution, which includes salts, sugars, amino acids and any other nutrients required for the maintenance of the cells in the culture in a viable state. Non-limiting examples of commercially available basic media that may be utilized in accordance with the invention comprise Neurobasal™, KO-DMEM, DMEM, DMEM/F12, Cellgro™ Stem Cell Growth Medium, or X-Vivo™. The basic medium may be supplemented with a variety of agents as known in the art dealing with cell cultures. The following is a non-limiting reference to various supplements that may be included in the culture system to be used in accordance with the present disclosure:

- serum or with a serum replacement containing medium, such as, without being limited thereto, knock out serum replacement (KOSR), Nutridoma-CS, TCH™, N2, N2 derivative, or B27 or a combination;
- an extracellular matrix (ECM) component, such as, without being limited thereto, fibronectin, laminin and gelatin. The ECM may them be used to carry the one or more members of the TGFβ superfamily of growth factors;
- an antibacterial agent, such as, without being limited thereto, penicillin and streptomycin;
- non-essential amino acids (NEAA),
- neuortrophins which are known to play a role in promoting the survival of SCs in culture, such as, without being limited thereto, BDNF, NT3, NT4.

Once the cells are promoted into the RPE fate, the RPE cells may be withdrawn/harvested from the culture by known methods, for use in various applications.

The present disclosure also provides RPE cells obtained by directed differentiation of hSC in the presence of one or more members of the TGFβ superfamily. In accordance with one embodiment, the RPE cells are obtained by the method of the invention.

Further to the above, the RPE cells produced by the directed differentiation according to the present disclosure have specific properties in comparison to RPE cells that develop during spontaneous differentiation.

Figure 4A:
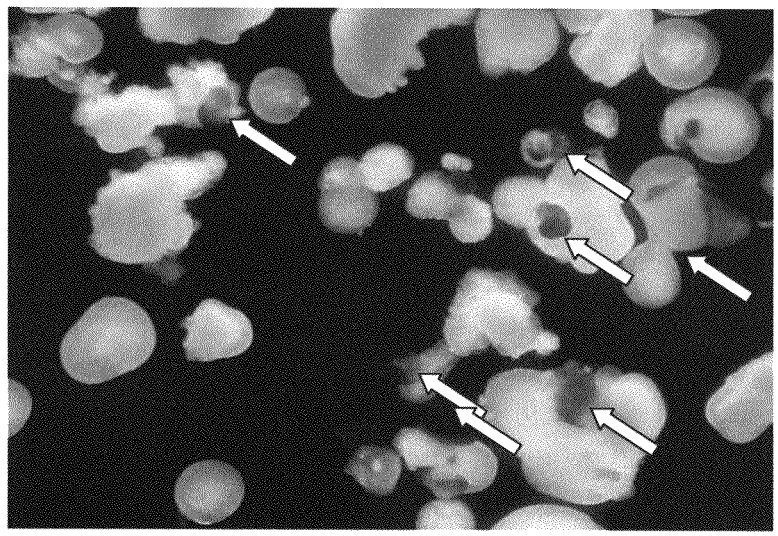
Figure 11A:
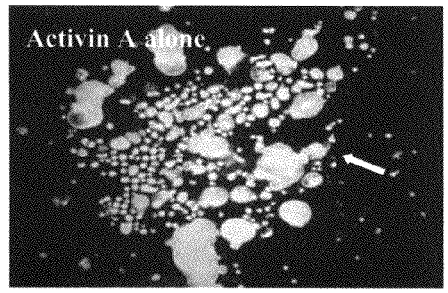
FIGS. 11A-11P: Analysis of morphology and gene expression showing that factors from the TGFβ family promote differentiation towards RPE fate. Dark field micrographs of hESC-derived clusters differentiating for 4 weeks showed the appearance of pigmented cells at this early stage in the presence of activin (FIG. 11A). as well as the increase in number of pigmented clusters differentiating in the presence of activin A and NA (FIG. 11C) as opposed to NA only (FIG. 11B). Similar to activin A, supplementation with TGFβ1 also increases the appearance of pigmented clusters (FIG. 11D). In contrast, the application of the inhibitor of activin signaling pathway, SB431542, together with activin A and NA reduced the effect of activin A on the appearance of pigmented clusters (FIG. 11E). The development of pigmented clusters was also abolished by culturing the cells in the presence of FGFβ together with NA (FIG. 11F). Expression of transcripts of activin receptors and activin A was demonstrated by RT-PCR analysis of 2 weeks old clusters cultured in the presence or absence of NA and undifferentiated hESCs as controls (FIG. 11G). Histogram analysis of the percentage of clusters containing pigmented areas at 4 weeks following culture in the presence of NA, NA+ActA, NA+SB431542, NA+ActA+SB431542, NA+TGFβ1 (FIG. 11H). Histogram analysis of the percentage of pigmented cells after 4 weeks of culture with NA (bars with bold line) or activin A and NA (bars with diagonal stripes) supplementation (FIG. 11I). Histogram analysis of the percentage of pigmented cells (FIG. 11J) and the level of expression of transcripts of the RPE markers, Bestrophin (FIG. 11K) and RPE65 (FIG. 11L) at different concentrations of activin A, that 140 ng/ml is optimal for RPE induction. Real-time PCR time-course analysis of the effect of activin A on the expression levels of retinal and RPE genes, Bestrophin (FIG. 11M), MiTF-total (FIG. 11N), Rx1 (FIG. 11O) and Chx10 (FIG. 11P), in hESCs differentiating in the presence of NA with (bars with diagonal stripes) or without (bars with bold line) activin A supplementation $**p<0.005$. (white arrows mark pigmented areas within differentiating clusters).
Figure 11D:
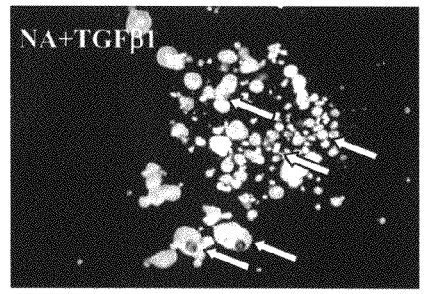
Figure 11B:
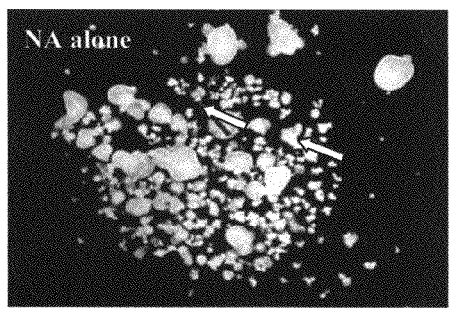
Figure 11E:
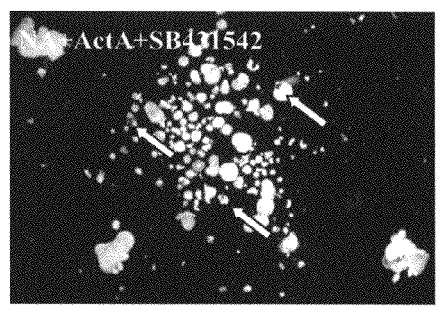
Figure 11C:
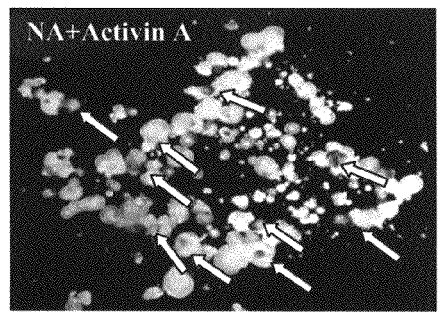
Figure 11F:
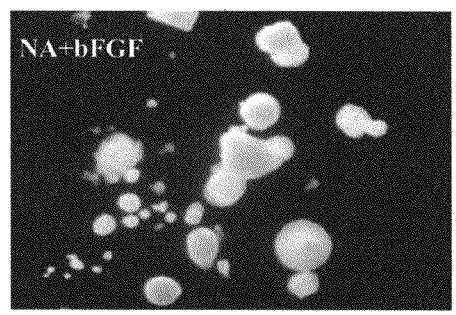
Figure 11G:
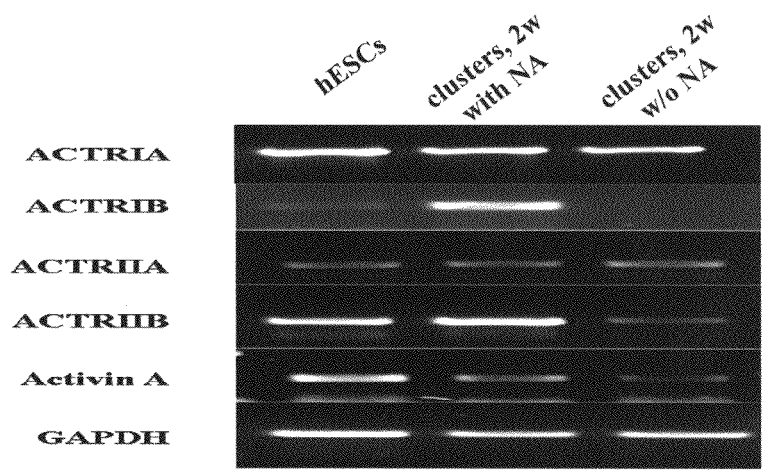
Figure 11H:
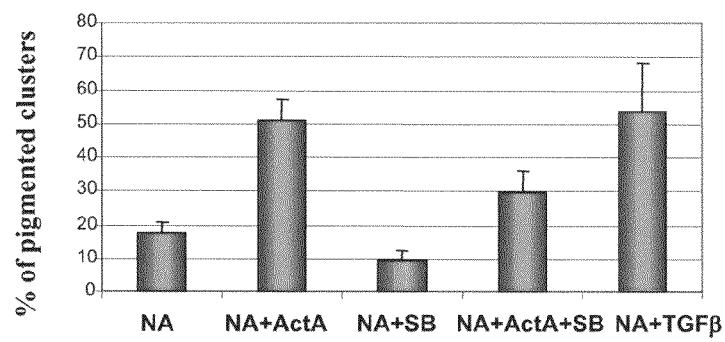
Figure 11I:
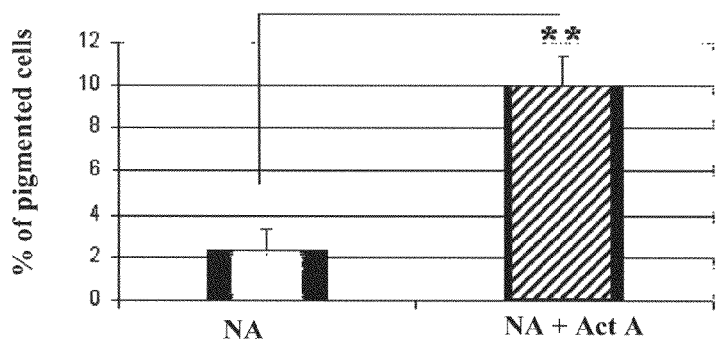
Figure 11J:
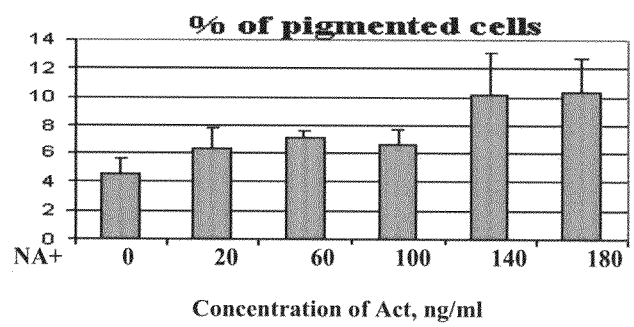
Figure 11K:
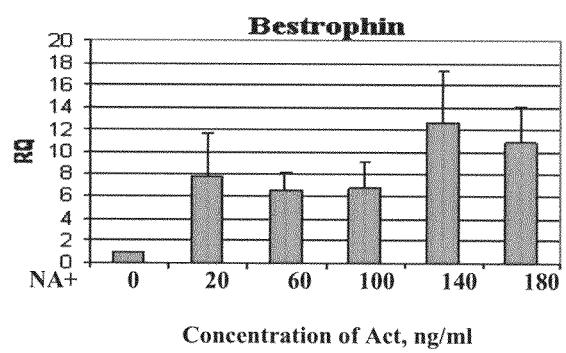
Figure 11L:
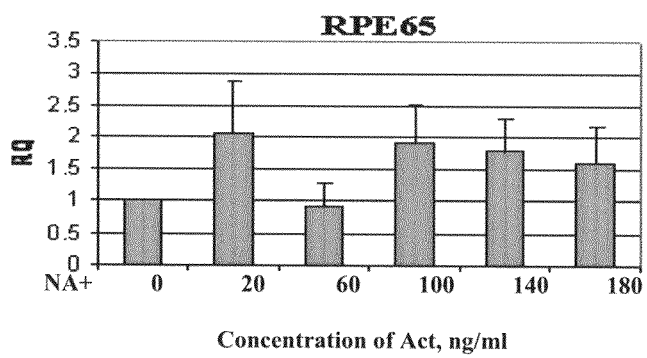
Figure 11M:
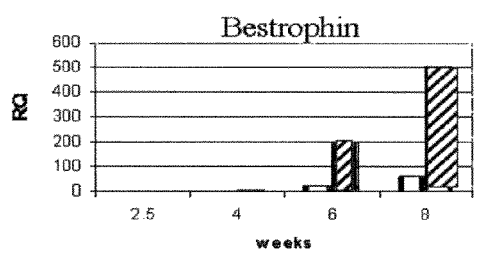
Figure 11N:
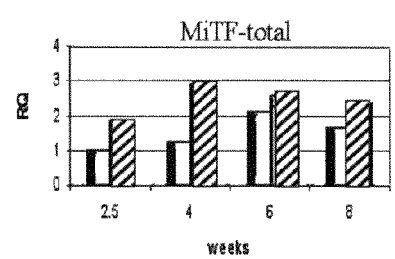
Figure 11O:
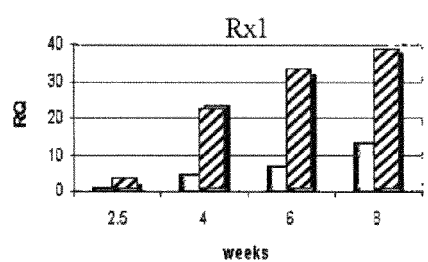
Figure 11P:
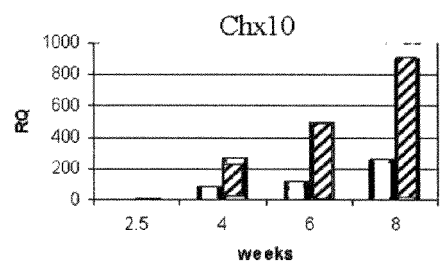

- The differentiating cells have the potential to respond to TGFβ signaling in their development and differentiation.
- The resulting RPE cells are mature cells (terminally differentiated);
- The mature RPE cells display darker pigmentation in comparison to RPE cells formed during spontaneous differentiation.
- The mature RPE cells express significantly higher levels of transcripts of markers of mature RPE cells such as bestrophin, and RPE65 as compared to their expression in RPE cells produced by spontaneous differentiation. In this connection, reference is made, for example, to FIGS. 9J, 11M and 11K showing the expression of bestrophin in spontaneous differentiation (no NA) as compared to differentiation in the presence of NA (FIG. 9J) and the augmenting effect of activin A on directed differentiation (FIGS. 11K, 11M and 4E). Further reference is made to FIGS. 1B and 9I showing the expression of RPE65 in spontaneous differentiation (no NA) as compared to differentiation in the presence of NA and further as compared to the augmenting effect of activin A in FIG. 4D.
- In electron microscope (EM) analysis the RPE cells display morphological characteristics of mature authentic RPE cells that are not demonstrated within RPE-like cells that were derived from spontaneously differentiating hSC such as apical villi, tight junctions, and basal membrane.

The RPE cells produced by the method of the present disclosure may be used for large scale and/or long term cultivation of such cells. To this end, the method of the invention is to be performed in bioreactors suitable for large scale production of cells, and in which undifferentiated hSCs are to be cultivated in accordance with the invention. General requirements for cultivation of cells in bioreactors are well known to those versed in the art.

Alternatively, the RPE cells produced by the method of the present disclosure may be expanded after their derivation. For expansion, they are dissociated, plated at low density on an extra cellular matrix, preferably poly-D-lysine and laminin, and cultured in serum-free KOM with NA. Under these culture conditions, the pigmented cells loose pigmentation and acquired a fibroid-like morphology. Following further prolonged culture and proliferation into high-density cultures, the cells re-acquired the characteristic polygonal shape morphology and pigmentation of RPE cells.

The RPE cells may be expanded in suspension or in a monolayer. The expansion of the RPE cells in monolayer cultures may be modified to large scale expansion in bioreactors by methods well known to those versed in the art.

It would be well appreciated by those versed in the art that the derivation of RPE cells from hSC is of great benefit. They may be used as an in vitro model for the development of new drugs to promote their survival, regeneration and function. hSC-derived RPE cells may serve for high throughput screening for compounds that have a toxic or regenerative effect on RPE cells. They may be used to uncover mechanisms, new genes, soluble or membrane-bound factors that are important for the development, differentiation, maintenance, survival and function of photoreceptor cells.

The RPE cells may also serve as an unlimited source of RPE cells for transplantation, replenishment and support of malfunctioning or degenerated RPE cells in retinal degenerations. Furthermore, genetically modified RPE cells may serve as a vector to carry and express genes in the eye and retina after transplantation.

Thus, in accordance with a further aspect of the present disclosure there is provided a method of transplanting RPE cells into a subject's eye, the method comprises:

(a) providing a cell culture comprising hSCs;

(b) culturing cells in a culture system comprising a basic medium supplemented with one or more member of TGFβ superfamily whereby the hSCs are promoted to differentiate into RPE cells;

(c) harvesting RPE cells from said cell culture; and (c) transplanting said differentiated RPE cells into said subject's eye.

Harvesting of the cells may be performed by various methods known in the art. Non-limiting examples include mechanical dissection and dissociation with papain. Other methods known in the art are also applicable.

The hSCs-derived RPE cells may be transplanted to various target sites within a subject's eye. In accordance with one embodiment, the transplantation of the RPE cells is to the subretinal space of the eye, which is the normal anatomical location of the RPE (between the photoreceptor outer segments and the choroids). In addition, dependant upon migratory ability and/or positive paracrine effects of the cells, transplantation into additional ocular compartments can be considered including the vitreal space, the inner or outer retina, the retinal periphery and within the choroids.

Further, transplantation may be performed by various techniques known in the art. Methods for performing RPE transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Opthalmology April 2000; 107 (4): 719-24; and Jpn J Opthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

In accordance with one embodiment, transplantation is performed via pars pana vitrectomy surgery followed by delivery of the cells through a small retinal opening into the sub-retinal space or by direct injection. Alternatively, cells may be delivered into the subretinal space via a trans-scleral, trans-choroidal approach. In addition, direct trans-scleral injection into the vitreal space or delivery to the anterior retinal periphery in proximity to the ciliary body can be performed.

The RPE cells may be transplanted in various forms. For example, the RPE cells may be introduced into the target site in the form of cell suspension, or adhered onto a matrix, extracellular matrix or substrate such as a biodegradable polymer or a combination. The RPE cells may also be transplanted together (co-transplantation) with other retinal cells, such as with photoreceptors.

Thus, the invention also pertains to a composition comprising hSCs-derived RPE cells obtained by the method of the invention. The composition is preferably such suitable for transplantation into the eye.

Various eye conditions may be treated or prevented by the introduction of the RPE cells obtained by the method of the invention to a subject's eye. The eye conditions may include retinal diseases or disorders generally associated with retinal dysfunction, retinal injury, and/or loss of retinal pigment epithelium. A non-limiting list of conditions which may be treated in accordance with the invention comprises retinitis pigmentosa, lebers congenital amaurosis, hereditary or acquired macular degeneration, age related macular degeneration (AMD), Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neovascular or traumatic injury.

Without being bound by theory, the transplanted RPE cells may exert their therapeutic effect through multiple mechanisms. One mechanism is trophic supportive effect promoting the survival of degenerating photoreceptors or other cells within the retina. RPE cells derived from hSCs by the methods of this disclosure and in the presence of a member of the TGFβ super family are capable of preserving the photoreceptors adjacent to them potentially by a trophic effect.

The transplanted RPE cells may also exert their effect through a regeneration mechanism replenishing mal functioning and/or degenerating host RPE cells. RPE cells derived from hSCs by the methods of this disclosure and in the presence of a member of the TGFβ super family can replenish mal functioning host RPE. The transplanted cells are mature and have the functional capability of phagocytosis of shed outer segments of photoreceptors which include rhodopsin.

As mentioned above the RPE cells derived from hSCs by the methods of this disclosure and in the presence of a member of the TGFβ super family are mature and as such they do not proliferate in vivo after transplantation. Therefore, RPE cells derived from hSCs by the methods of this disclosure are safer for transplantation therapy and carry a reduced risk for development into teratoma tumors or tumors of proliferating precursor cells.

As used herein, the term "treating" or "treatment" refers to the therapeutic as well as the prophylactic effect of the hSC-derived RPE cells of the invention on a subject's eye condition, the effect may generally include, amelioration of symptoms associated with the conditions, lessening of the severity or curing the condition, more specifically, the effect may include reversal of damage caused to the treated subject's retina and RPE, improved function of the subject's retina, rebuilding of the subject's retina and RPE by replacement and/or support of failing host retinal and RPE cells, directly or by paracrine effect as well as to the prophylactic effect which may be exhibited by the attenuation, inhibition or cessation in damage caused to the subject's retina as a result of the condition.

As used in the specification and claims, the forms "a", "an" and "the" include singular as well as plural references unless the context clearly dictates otherwise. For example, the term "a growth factor" includes one or more growth factors, and the term "growth factors" includes one growth factor as well as more than one growth factor.

As used herein, the term "or" means one or a combination of two or more of the listed choices. Furthermore, the use of the phrase "selected from . . . " followed by a list of choices separated by the term "and" includes one or a combination of two or more of the listed choices.

Further, as used herein, the term "comprising" is intended to mean that the methods or composition includes the recited elements, but does not exclude others. Similarly, "consisting essentially of" is used to define methods and systems that include the recited elements but exclude other elements that may have an essential significance on the functionality of the culture systems of the inventions. For example, a culture system consisting essentially of a basic medium, medium supplements and feeder cells will not include or will include only insignificant amounts (amounts that will have an insignificant effect on the propagation and differentiation of cells in the culture system) of other substances that have an effect on cells in a culture. Also, a composition consisting essentially of the elements as defined herein would not exclude trace contaminants from the isolation and purification method. "Consisting of" shall mean excluding more than trace amounts of other elements. Embodiments defined by each of these transition terms are within the scope of this invention.

Further, all numerical values, e.g., concentration or dose or ranges thereof, are approximations which are varied (+) or (−) by up to 20%, at times by up to 10%, from the stated values. It is to be understood, even if not always explicitly stated that all numerical designations are preceded by the term "about". It also is to be understood, although not always explicitly stated, that the reagents described herein are merely exemplary and that equivalents of such are known in the art.

SOME EXEMPLARY EMBODIMENTS

Materials and Methods

HES Cell Culture

Human ESC (HES1 cell line) and hESCs engineered by lentiviral vector to constitutively express eGFP [Gropp M, Itsykson P, Singer O, Ben-Hur T, Reinhartz E, Galun E, and Reubinoff B E. Stable genetic modification of human embryonic stem cells by lentiviral vectors. Molecular Therapy7: 281-7 (2003)] were cultured on human foreskin fibroblasts feeder layers in KO medium (KOM) consisting of 86% KO-DMEM (Gibco, Invitrogen, Gaithersburg, Md.), 14% KOSR (Gibco), 1 mM glutamine, 1% nonessential amino acids, 50 units/ml penicillin (Gibco), 50 μg/ml streptomycin, (Gibco) and 4 ng/ml bFGF (R&D Systems, Inc., Minneapolis, Minn.). hES cells were weekly passaged with type IV collagenase (1 mg/ml; Gibco) and plated onto a fresh feeder layer. A week before induction of differentiation, the cells were passaged by dissociation into nearly a single-cell suspension with Ca/Mg$^{++}$-free PBS supplemented with 0.05% EDTA (Biological Industries, Beit Haemek, Israel) and were re-plated on the feeders.

EB Formation in Suspension Culture

Six-eight days after plating the hES cells that were dissociated into single cells as above; they were removed from the feeders by treatment with type IV collagenase. The clumps were cultured for various periods up to 12 weeks in suspension within bacteriological dishes precoated with 0.1% low melting temperature agarose in KO medium (KOM) consisting of 86% KO-DMEM, 14% KOSR, 1 mM glutamine, 1% nonessential amino acids, 50 units/ml penicillin, and 50 μg/ml streptomycin, in the presence or absence of 10 mM nicotinamide (NA) (Sigma, St. Louis, Mo., USA). In some experiments the medium used was Neurobasal™ medium (Gibco) supplemented with N2 supplement (1:100) (Gibco) (NN medium), which was substituted after 1 week with DMEM/F12 (Gibco) supplemented with B27 (1:50) (Gibco).

Differentiation of hESCs into RPE Cells in the Presence of TGF-β Growth Factors or Inhibitors Human ESCs were allowed to differentiate as free-floating clusters in KOM as above for up to six weeks in the presence of nicotinamide (NA) 10 mM. After the first week or 2 weeks of differentiation, cultures were supplemented with activin A 20-180 ng/ml (PeproTech Inc, Rocky Hill, N.J.), with TGFβ3 (1 ng/ml; R&D Systems Inc, Minneapolis, Minn.) with TGFβ1 (1 ng/ml-20 ng/ml; R&D Systems Inc) or with SB431542 (5 μM-50 μM, Sigma). Control cultures were supplemented with NA alone.

Human ESCs in suspension in KOM were also supplemented after one week with the bone morphogenetic protein (BMP) antagonist noggin (700 ng/ml R&D Systems Inc, Minneapolis, Minn.) in the presence and absence of NA, or during the 3$^{rd}$ and 4$^{th}$ weeks with FGFβ (20 ng/ml PeproTech Inc) in the presence of NA and allowed to differentiate up to an age of 6 weeks as free-floating clusters in suspension.

Description of Expansion of the RPE Cells

To expand the RPE cells, the pigmented clusters were gently mechanically dissociated into small clamps and plated at low density on poly-D-lysine ((30-70 kDa, 10 μg/ml) and laminin (4 μg/ml), and cultured in KOM with NA. Under these culture conditions, the pigmented cells lost pigmentation and acquired a fibroid-like morphology. Following further culture for 1.5 month and proliferation into high-density cultures, the cells re-acquired the characteristic polygonal shape morphology and pigmentation of RPE cells.

Immunostaining and real-time RT-PCR were performed on all cultures as described below.

Indirect Immunofluorescent Staining of Differentiated Cells within Clusters

To characterize the immunophenotype of cells within the aggregates, the clusters cultivated for 2, 4, 6 or 8 weeks were gently dissociated either with 0.04% trypsin/0.04% EDTA or with Papain Dissociation System (Worthington Biochemical, Lakewood, N.J.), and the resulting small clumps and single cells were plated in KO medium supplemented with NA on poly-D-lysine (30-70 kDa, 10-20 μg/ml) alone or supplemented with either laminin (4 μg/ml) or fibronectin (10-20 μg/ml; all from Sigma, St. Louis, http://www.sigmaaldrich-.com). The cells were fixed with 4% paraformaldehyde after 2 hours and examined for the expression of nestin (1:200), polysialic acid NCAM (PSA-NCAM) (1:100), Musashi (1:200; all from Chemicon, Temecula, from CA), Pax6 (DSHB, 1:100 or Chemicon, 1:250), Otx2 (Chemicon, 1:200), MiTF (Lab Vision Corporation, Fremont, Calif.; mouse IgG$_1$, 1:50).

For immunostaining of enriched preparations of pigmented cells, the pigmented (Brown) clusters of cells within the floating clumps, that differentiated 8-10 weeks, were mechanically dissected and isolated by glass micropipettes or scalpel blades (No 15; Swarm-Morton Sheffield, Eng).

The isolated clusters that were enriched for pigmented cells were further dissociated into smaller clumps mechanically by trituration with/without the aid of trypsin (0.025%, 3 mM EDTA in PBS) digestion or papain dissociation (Papain Dissociation System; Worthington Biochemical Corporation, Lakewood, N.J.). The small clusters of cells were plated on poly-D-lysine-coated (30-70 kDa, 10 μg/ml; Sigma) and laminin-coated (4 μg/ml; Sigma) glass coverslips and cultured for an additional 3-5 weeks in the culture medium used for suspension culture of the hESC clusters. Differentiated cells within the outgrowth were fixed with 4% paraformaldehyde for 30 minutes at room temperature. For immunostaining with anti-intracellular marker antibodies, cell membranes were permeabilized with 0.2% Triton X100 (Sigma) in PBS for 30 minutes, supplemented with normal goat serum (5%, Biological Industries) for blocking. The cells were incubated with the following primary antibodies: anti-MiTF (Lab Vision Corporation, Fremont, Calif.; mouse IgG$_1$, 1:50); anti-RPE65 (Novus Biologicals, Littleton, Colo.; mouse IgG$_1$, 1:300); anti-Bestrophin (Novus Biologicals; mouse IgG$_1$, 1:150); anti-ZO-1 (Zymed Laboratories Inc., San Francisco, Calif.; rabbit polyclonal, 1:10); anti-Ki67 (Dako Denemark A/S, 1:50) and anti-CRALBP (kindly provided by John C. Saari, University of Washington, Seattle; rabbit polyclonal, 1:100). The cells were also incubated with Phalloidine (1:200 Sigma)

Primary antibody localization was performed by using fluorescein isothiocyanate (FITC)-conjugated goat anti-mouse immunoglobulins (Dako Denmark A/S; 1:20-1:50), goat anti-mouse IgG conjugated to Cy$^{TH}$3 (1:500) (Jackson ImmunoResearch Laboratories Inc, West Grove, Pa.), rabbit anti-goat IgG conjugated to Cy2 (1:200; Jackson ImmunoResearch Laboratories Inc) and swine anti-rabbit Ig conjugated to fluorescein isothiocyanate (FITC) (Dako; 1:50).

Analysis of hESC Clusters by RT-PCR and Real-Time PCR

Total RNA was extracted from hESCs grown under serum-free conditions (1 week after passage), and at sequential time points up to 8 weeks during culturing of hESC-derived clusters in the presence or absence of 10 mM nicotinamide and with or without supplementation with TGFβ-superfamily growth factors or antagonists. The RNA was isolated using TRIzol reagent (Invitrogen,http://www.invitrogen.com) or TRI-Reagent (Sigma). cDNA synthesis was carried out using Moloney murine leukemia virus reverse transcriptase (M-MLV RT) and random primers, according to the manufacturer's instructions (Promega Corporation, Madison, Wis., http://www.promega.com). Polymerase chain reaction (PCR) was carried out using standard protocols with Taq DNA Polymerase (Gibco-BRL). Amplification conditions were as follows: denaturation at 94° C. for 15 seconds, annealing at 55° C. for 30 seconds, and extension at 72° C. for 45 seconds. The number of cycles varied between 18 and 40, depending on particular mRNA abundance. Primer human sequences for identifying human gene transcripts (forward and reverse 5'-3') and the length of the amplified products were as follows (SEQ ID NOs. 1-12):

```
MiTF-A
(GAGCCATGCAGTCCGAAT, GACATGGCAAGCTCAGGACT;
486 bp);

RPE65
(GCTGCTGGAAAGGATTTGAG, CAGGCTCCAGCCAGATAGTC;
231 bp);

Bestrophin
(GAATTTGCAGGTGTCCCTGT, ATCCTCCTCGTCCTCCTGAT;
214 bp);

CRALBP
(AGCTGCTGGAGAATGAGGAA, CAAGAAGGGCTTGACCACAT;
218 bp)

MERTK
(AAGTGATGTGTGGGCATTTG, TCTAAGGGATCGGTTCTCCA,
189 bp);

ACTRIA
(AATGTTGCCGTGAAGATCTTC, CTGAGAACCATCTGTTGGGTA;
699 bp);

ACTRIB
(CACGTGTGAGACAGATGGG, GGCGGTTGTGATAGACACG;
346 bp);

ACTRIIA
(AACCATGGCTAGAGGATTGGC, CTTTCACCTACACATCCAGCTG;
551 bp);

ACTRIIB
(CACCATCGAGCTCGTGAAG, GAGCCCTTGTCATGGAAGG;
611 bp);

Activin A
(CTTGAAGAAGAGACCCGAT; CTTCTGCACGCTCCACCAC;
262 bp);

β-actin
(TTCACCACCACGGCCGAGC, TCTCCTTCTGCATCCTGTCG;
351 bp);

GAPDH
(AGCCACATCGCTCAGACACC; GTACTCAGCGCCAGCATCG;
301 bp).
```

For Real-time PCR the levels of transcripts were monitored using TaqMan primers and probes that were derived from the commercially available TaqMan® Assays-on-Demand Gene Expression Products (Applied Biosystems, Foster City, Calif.): Oct4, ID Hs01895061; Musashi, ID Hs01045894; Pax6, ID Hs00240871; Six3, ID Hs00193667; Rx1, ID Hs00429459; Chx10, ID Hs01584048; MiTF-A, ID Hs01115553; MiTF-total, ID Hs01115557; Bestrophin, ID Hs00188249; RPE65, ID Hs00165642; Sox 10, ID Hs00366918; Crx, ID Hs00230899. Quantitative PCR analysis was performed using an ABI Prism 7000HT and ABI Prism 7900HT Sequence Detection Systems and TaqMan® Universal PCR Master Mix (Applied Biosystems) according to the manufacturer's protocol. Housekeeping gene β-glucuronidase (GusB, assay ID Hs99999908) was selected as an internal reference for normalization in the Real-Time RT-PCR quantification analysis and the relative expression level of each gene is shown as a relative value when the expression level of day 0 (or untreated cells) was set at 1. Amplification reactions were carried out in duplicates or triplicates according to manufacturer's protocol (Applied Biosystems).

Transmission Electron Microscopy and Phagocytosis of Latex Beads

Human ESC-derived clusters were cultured in suspension in KOM. The pigmented areas were then separated mechanically and were processed for transmission electron microscopy. The cells were fixed with 2% glutaraldehyde and 4% formaldehyde in 0.1 M cacodylate buffer, pH 7.4. After three washes in 0.1 M cacodylate buffer the tissue was post-fixed with 1% osmium tetroxide and 1.5% potassium fericyanide, dehydrated with increasing concentrations of ethanol and embedded in Agar 100 resin. Ultra-thin sections cut by an LKB ultrotome 3 were stained with uranyl acetate and lead citrate. Micrographs were taken with Tecnai 12 electron microscope (Phillips, Eindhoven the Netherlands http://www.philips.com) equipped with a Megaview II CCD camera and an Analysis version 3.0 software (Soft Imaging System, http://www.soft-imaging.net).

To examine phagocytotic ability, the pigmented clusters were incubated with 1-μm latex beads (Polysciences Inc., Warrington, Pa.) at a concentration of $1.0 \times 10^9$ beads/mL for 18 hours at 37° C. The pigmented clusters were then washed with PBS+, dissociated into single cells or small clumps using Papain Dissotiation System and plated on poly-D-lysine. Following fixation, the membranes of the cells were stained with red fluorescent die, PKH (Sigma). The phagocytosis was analyzed using confocal microscope (Olympus Fluoview FV1000)

Flow Cytometry

Flow cytometric analysis was performed to determine the number of PSA-NCAM and TRA-1-60 positive cells at different time points within the hESC-derived clusters differentiating with or without nicotinamide supplementation. The clusters were dissociated with 0.04% Trypsin/0.04% EDTA. The single cells were then stained with anti-PSA-NCAM or anti-Tra-1-60 antibodies (both from Chemicon; 1:100), detected with goat anti-mouse immunoglobulins conjugated to FITC (Dako; 1:100), and counterstained with the cell viability dye Propidium iodide (0.005 mg/ml; Sigma) Control cells were incubated only with a secondary antibody. The cell-associated immunoreactivity was analyzed with FACScalibur (Becton Dickinson Immunocytometry Systems), using CellQuest software.

Intravitreal and Subretinal Transplantation of hESC-Derived Differentiated RPE Cells For intra-ocular transplantation, hESCs engineered to express eGFP [as previously described in Gropp et al., Stable genetic modification of human embryonic stem cells by lentiviral vectors. Molecular Therapy 2003; 7: 281-7.) were used to generate RPE cells in culture as described above. Briefly, clusters enriched with pigmented cells were mechanically isolated by dissection following differentiation for 6-8 weeks in the presence of NA alone or in the presence of NA supplemented with activin A. To allow injection through a small bore glass capillary, the clumps were further dissociated into smaller clusters of cells by digestion with Papain (Papain Dissociation System; Worthington Biochemical Corporation, Lakewood, N.J.) at 37° C. for 30 minutes, followed by trituration.

Fifteen adult albino rats (body weight 230-250 g) and over 100 1-3 weeks outbred dystrophic RCS rats were used for intraocular transplantation. In RCS rats, a mutation in the Mertk gene causes RPE dysfunction which leads to retinal degeneration over the first few months of life. All animal experiments were conducted according to the ARVO Statement for the Use of Animals in Ophthalmic and Vision Research, and approved by the Institutional Committee for Animal Research of the Hebrew University-Hadassah Medical School.

For transplantation (as well as for eletroretinographic recordings) animals were anaesthetized with Ketamine HCl (Ketalar, Parke Davis, UK; 100 mg/kg), injected intra-peritoneally in combination with the relaxing agent Xylazine (2.0 mg/kg). Local anaesthetic drops (Benoxinate HCl 0.4%; Fischer Pharmaceuticals, Israel) were administered. The pupils were dilated with Tropicamide 0.5% (Mydramide, Fisher Pharmaceuticals, Israel) and Phenylephrine HCl 2.5% (Fisher Pharmaceuticals, Israel). Under visualization of a dissecting microscope (Stemi SV 11, Zeiss, Germany), approximately 100,000 cells in 4 μL of medium were injected into the vitreous or into the subretinal space via a transscleral, transchoroidal approach through a glass capillary coupled to a pneumatic Pico-injector (PLI-100; Medical System Corp., Greenvale, N.Y., http://www.medicalsystems.com). Fellow, non-injected eyes served as one type of control. As an additional control, eyes were injected with saline (Sodium Chloride Injection BP, 0.9%, B. Braun Melsungen AG, Melsungen, Germany).

During and after injection, no choroidal bleeding was observed. Animals were kept warm throughout and after the procedure using a heating lamp. Following transplantation, all animals received the immunosuppressive agent cyclosporine A (Sandimmune, Novartis Pharma AG, Basel, Switzerland) in their drinking water at a concentration of 210 mg/l.

In-Vivo and Ex-Vivo Imaging of Transplanted Cells

To monitor survival and location of the transplanted cells in-vivo, anesthetized animals were imaged using a color fundus camera (Zeiss, Germany) and fluorescence of the GFP-expressing cells was detected using fluorescein filters on a scanning laser to opthalmoscope (Heidelberg HRA, Germany). In some eyes, location of the GFP-positive grafts was also determined ex-vivo in eye-cup preparations using a fluorescent microscope (Canon, Japan).

Assessment of Host Retinal Function Following Intra-Ocular Transplantation of hESC-Derived RPE Cells Four to six weeks after transplantation, retinal function was assessed in transplanted and control RCS rat eyes by electroretinography (ERG). Full field ERGs were recorded following overnight dark adaptation. Animals were anesthetized with Ketamine and Xylazine in dim red light, and pupils were dilated with tropicamide and phenyephrine. Monopolar rat ERG lens electrodes (Medical Workshop, Amsterdam, Netherlands) were placed on each eye following additional topical anesthesia, with a reference electrode and a ground electrode placed on the tongue and tail respectively. A commercial computerized ERG system (LKC technologies, UTAS 3000) was used to record retinal responses to full field stimuli generated using a Xenon photostrobe flash (Grass, PS-22) mounted on a Ganzfeld bowl. Dim blue flashes under scotopic conditions were used to elicit a largely rod-driven response. At stronger stimulus intensities of blue, and with white flashes in the dark-adapted state, mixed cone-rod responses were recorded. Under light-adapted (photopic) conditions, with white flashes on a rod-suppressing 34 cd/m$^2$ white background, 1 Hz and 16 Hz cone responses were generated. Signals were filtered between 0.3-500 Hz, and signal averaging was used.

Histological and Immunohistochemical Evaluation of Transplanted Eyes

Animals were sacrificed 4-8 weeks after transplantation and eyes enucleated for histological and immunohistochemical examination. Following fixation in Davidson solution, eyes were embedded in paraffin and sectioned at 4 μm serial sections. Each fifth slide was stained with hematoxylin and eosin for histomorphologic evaluation and quantification. For indirect immunofluorescent studies, to characterize state of differentiation of the transplanted cells, specimens were de-paraffinized in xylene and dehydrated in graded alcohols, rinsed with phosphate-buffered saline (PBS, pH 7.4), and incubated with 10 mM citrate buffer (pH 6.0) at 110° C. for 4 minutes. After washing with PBS, specimens were blocked for 1 hour at room temperature with PBS solution containing 1% bovine serum albumin (BSA), 0.1% Triton X100 (Sigma-Aldrich), and 3% normal goat or normal donkey serum. Subsequently, sections were incubated for 1 hour in a humidified chamber with appropriate combinations of the following primary antibodies: anti-green fluorescent protein (anti-GFP), conjugated with fluorescein (FITC) or rhodamine (TRITC) (Santa Cruz Biotechnology, Inc, Santa Cruz, Calif.; mouse monoclonal, 1:100); anti-RPE65 (Novus Biologicals, Littleton, Colo.; mouse IgG$_1$, 1:100); anti-Bestrophin (Novus Biologicals; mouse IgG$_1$, 1:100); anti-ZO-1 (Zymed Laboratories Inc., San Francisco, Calif.; rabbit polyclonal, 1:100); and anti-rhodopsin (Santa Cruz Biotechnology, Inc, Santa Cruz, Calif.; rabbit polyclonal, 1:100). Primary antibody localization was performed after washing in PBS by using Cy™2-conjugated goat anti-rabbit IgG (1:200), Cy™2-conjugated goat anti-mouse IgG (1:200), Cy™3-conjugated goat anti-rabbit IgG (1:200), Cy™2-conjugated donkey anti-mouse IgG (1:200), Cy™5-conjugated donkey anti-rabbit IgG (1:200; all from Jackson ImmunoResearch Laboratories, Inc, West Grove, Pa.). Nuclei were counterstained with 4,6-diamidino-2-phenylindole (DAPI)-containing mounting medium (Vector Laboratories, Burlingame, Calif.) or with propidium iodide 1 μg/ml (BioLegend, San Diego, Calif.). To determine the specificity of the antigen-antibody reaction, corresponding negative controls with an irrelevant isotype-matched antibody were performed. An Olympus BX41 microscope equipped with a DP70 digital camera (Olympus, Japan) was used for fluorescent and light microscopy imaging. Confocal images were collected on an Olympus Fluoview 300 (FV300) confocal microscope (Olympus, Japan) built around an IX70 inverted microscope. 488-nm Ar, 543 HeNe-Green, and 633 HeNe Red lasers were used in combination with Nomarski optics.

Quantification of Photoreceptor Layer Rescue in Vicinity to RPE Grafts

To quantify the effect of hESC-derived RPE transplantation on the degenerating host retina, high resolution microscopic images of hematoxylin and eosin stained sections were obtained and montages of the full length of the retina constructed using Photoshop software (Adobe, USA). Total retinal thickness, thickness of the outer nuclear (photoreceptor) layer as well as thickness of the inner- and outer-segments layer were measured in proximity to subretinal grafts of hESC-derived RPE cells using the J-image program (NIH). These were compared to measurements obtained in the corresponding opposite side of the retina, distant from the graft. Since the degenerative process in RCS rats is location-dependant, thickness was measured in areas that were of equal distance from the cilliary body. In each area, at least three equally spaced measurements were averaged.

Results

Characterization of Differentiated RPEs

Figure 3A:
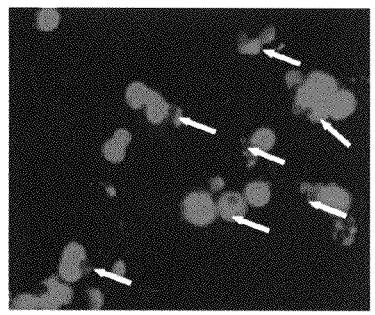
FIGS. 3A-3L: Melanin-expressing cells within free floating clusters of hESCs are putative RPE cells. Dark field micrograph of free floating clusters of differentiating hESCs with defined areas highly enriched for pigmented cells (FIG. 3A). Fluorescence (FIG. 3B) and phase contrast (FIG. 3C) images of pigmented cells following dissociation and plating that are immunoreactive with anti Otx2 and MiTF. A dark field micrograph of differentiating clusters after plating illustrating confined pigmented areas is shown (FIG. 3D). Phase contrast image of cells within the pigmented areas having morphological characteristics that are typical of RPE cells (FIG. 3E). Indirect immunofluorescent stainings showing that these cells express markers of RPE cells, including MiTF (FIG. 3F), ZO-1 (FIG. 3G), Bestrophin (FIG. 3H), RPE65 (FIG. 3I), and CRALBP (FIG. 3J). After dissociation, plating at low density and cultivation, the pigmented cells lose pigmentation and acquire fibroid-like morphology (phase contrast image) (FIG. 3K). Following further prolonged cultivation and proliferation into high density cultures the cells reacquire the morphology and pigmentation characteristic of RPE cells (FIG. 3L).

Differentiation of hESCs was induced by culturing them as free-floating clusters in KO medium supplemented with NA. Under these culture conditions defined areas highly enriched for pigmented cells developed within the differentiating clusters, as shown in FIG. 3A. These pigmented areas appeared after 4 weeks of differentiation and after 8 weeks 72.9±2.5% of the clusters had pigmented areas. Pigmented areas were not observed after 4 weeks of differentiation in the absence of NA supplementation, and in these conditions only 13.1±4.8% developed pigmented areas after 8 weeks (FIGS. 8A, and 8B). Thus, NA treatment augmented/promoted differentiation within hESC clusters into pigmented cells as compared to spontaneously differentiating hESC clusters.

Figure 3D:
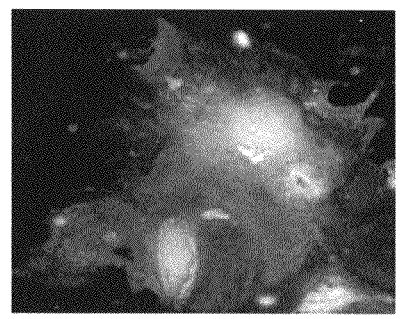
Figure 3B:
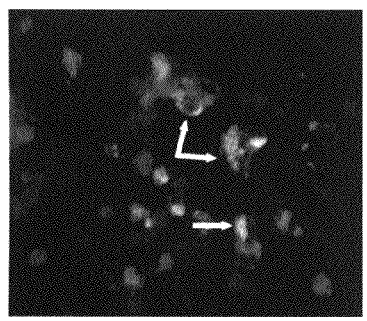
Figure 3E:
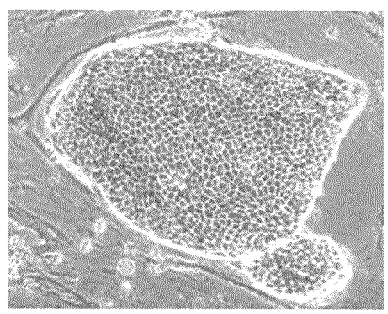
Figure 3C:
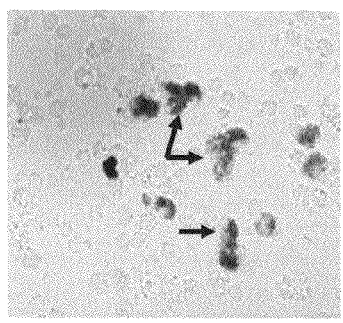
Figure 3F:
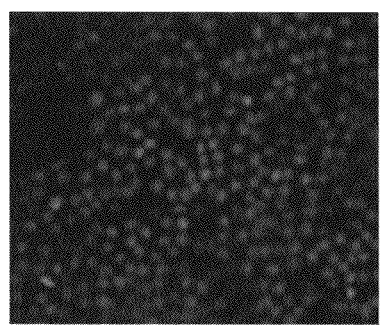
Figure 3G:
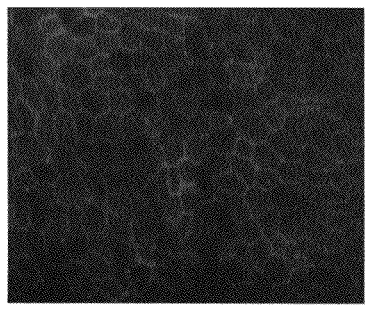
Figure 3J:
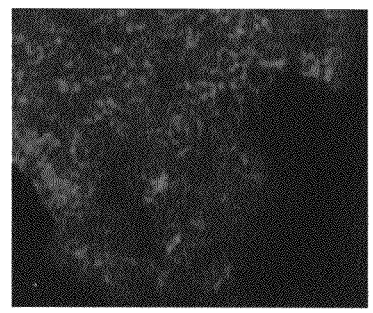
Figure 3H:
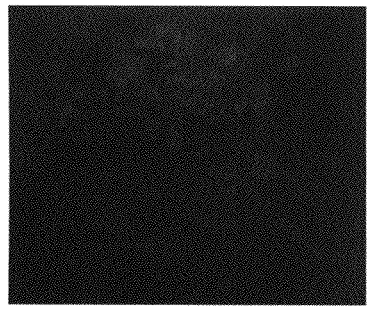
Figure 10A:
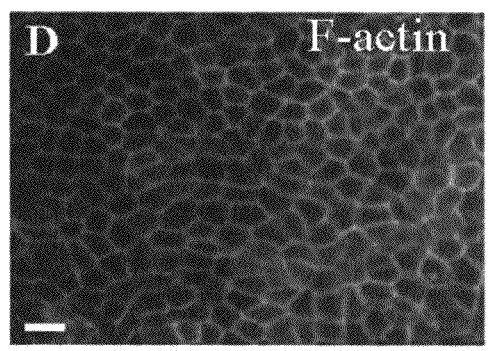
FIG. 10A-10J: Analysis of morphology, marker expression and function showing that the pigment-expressing cells within free-floating clusters of hESCs are putative RPE cells. Phalloidine staining showing distribution of F-actin within the hESC-derive pigmented progeny which is characteristic of RPE (FIG. 10A); After dissociation, plating at low density and cultivation, the pigmented cells lost pigmentation and acquired fibroid-like morphology (phase contrast image, 1 week of culture) (FIG. 10B). Following further prolonged cultivation and proliferation into high density cultures the cells reacquired the morphology and pigmentation characteristics of RPE cells (1.5 month of culture) (FIG. 10C). Electron microscopic analysis of hESC-derived RPE cells showing features characteristic of RPE: microvilli (FIG. 10D), a basal membrane (FIG. 10E), melanin granules (FIG. 10D), tight junctions (FIG. 10F). Phase contrast FIG. 10G and fluorescent images (FIG. 10H-J) showing phagocytosis of green fluorescent latex beads (Wight arrowheads) by the hESC-derived pigment cells; the cell membranes were stained with red fluorescent die PKH (grey color). The three confocal fluorescent images demonstrated serial z axis slices (FIG. 10H-J).

Within clusters that differentiated 8 weeks in the presence of NIC, 5.7±1.0% of the cells were pigmented, 5.4±1.1% expressed the early RPE marker MiTF and in most cases the expression of MiTF correlated with pigmentation (FIG. 8C). Partially dissociated and plated clusters of differentiated hESCs developed, among other types of differentiated cells, into colonies composed of monolayers of pigmented cells, as shown by a dark field micrograph (FIG. 3D) and a phase contrast image (FIG. 3E). The cells within these colonies assumed a polygonal shape and formed "cobble stone"-like sheets of cells with tight junctions between them (FIG. 3E), features that are highly characteristic of native RPE cells. The F-actin distribution within the cells was adjacent to their membranes, like authentic RPE cells as demonstrated by staining with Phalloidin (FIG. 10A). The pigmented, RPE cells co-expressed the RPE markers Otx2 (FIG. 3B) and MiTF-A (FIG. 3B and FIG. 3F), as well as ZO-1(FIG. 3G), Bestrophin (FIG. 3H), RPE65 (FIG. 3I), and CRALBP (FIG. 3J).

Figure 3K:
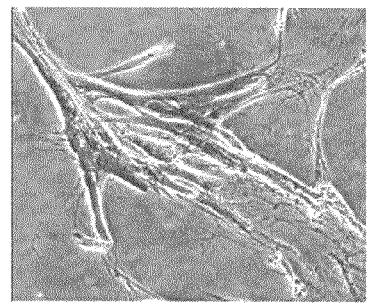
Figure 3I:
Figure 3L:
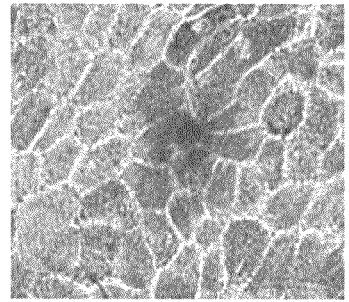
Figure 10B:
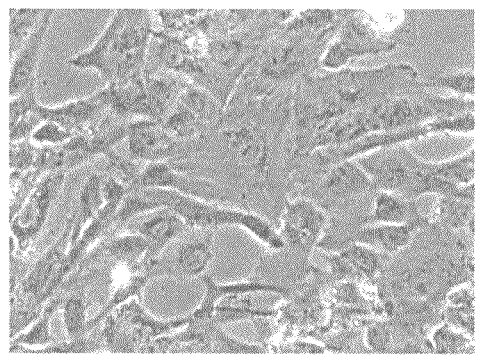
Figure 10C:
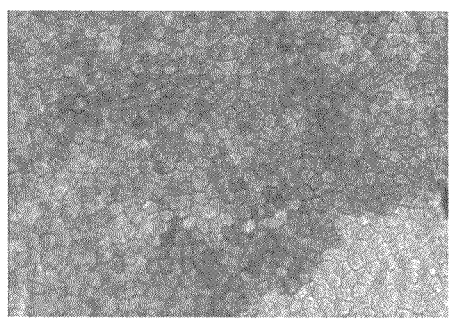

After dissociation, plating at low density and cultivation, the pigmented cells lost pigmentation and acquired a fibroid-like morphology, as shown by phase contrast imaging (FIGS. 3K, and 10B). Following further prolonged cultivation and proliferation into high-density cultures, the cells re-acquired the polygonal shape morphology and pigmentation of RPE cells (FIGS. 3L, and 10C).

Figure 10D:
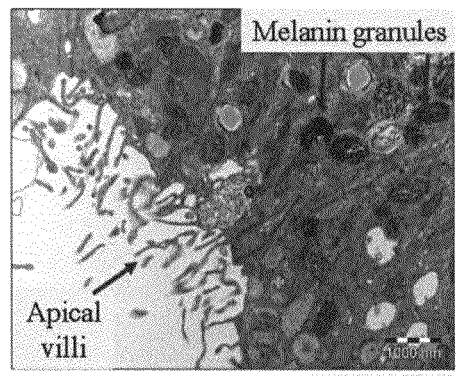
Figure 10E:
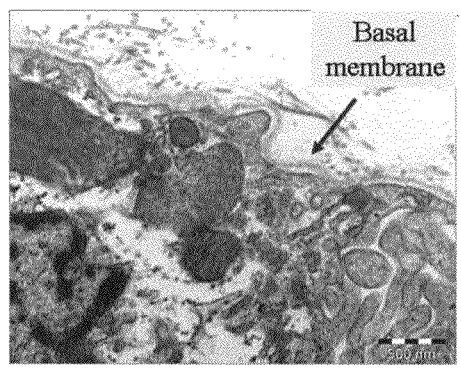
Figure 10F:
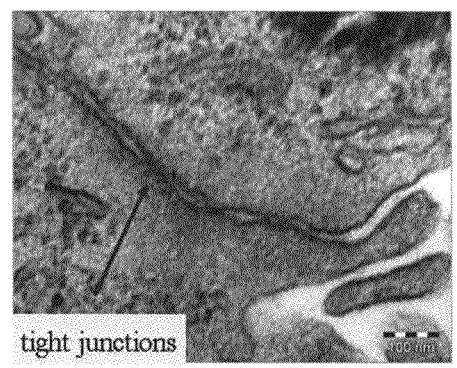
Figure 10G:
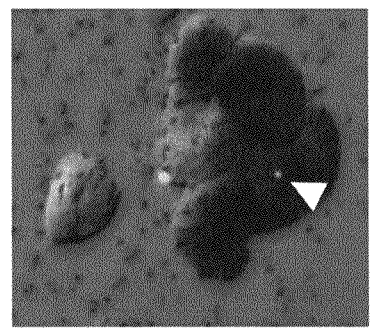

Electron microscopy (EM) analysis demonstrated that the hESC-derived pigmented cells had morphologic characteristics of native RPE cells including microvilli on their apical side (FIG. 10D), and basal membrane on their basal side (FIG. 10E). The cells contained melanin granules (FIG. 10D) and were attached by tight junctions (FIG. 10F).

Figure 10H:
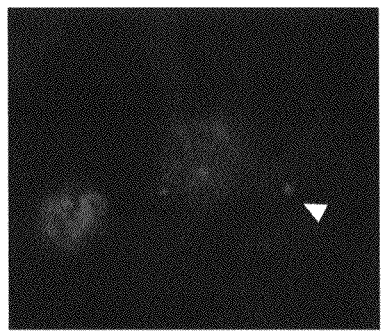
Figure 10I:
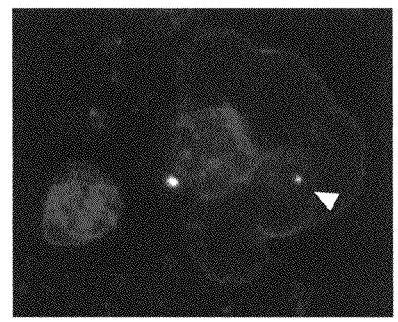
Figure 10J:
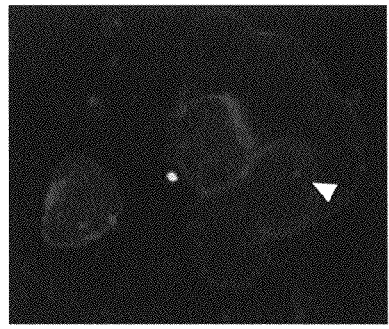

One of the most important functions of RPE cells is phagocytosis of photoreceptors shed outer segments. To examine whether the hESC-derived pigmented cells had phagocytic capability, they were incubated with 1-μm fluorescent latex beads. The three confocal fluorescent images demonstrate serial z axis slices (FIGS. 10H-10J). Confocal microscope analysis showed that the putative RPE cells were capable of phagocytosis of the fluorescent beads (FIGS. 10G-10J).

Differentiation-Inductive Effect of Nicotinamide

Figure 1A:
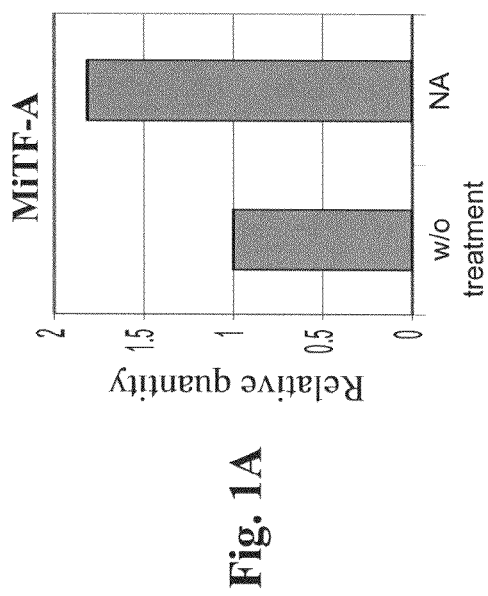
Figure 1C:
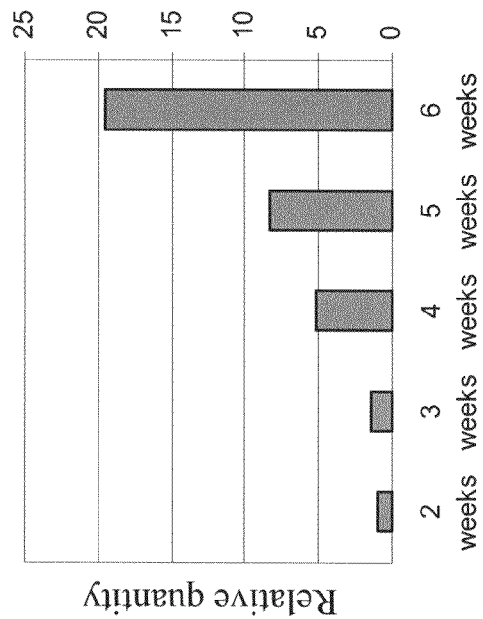
Figure 1D:
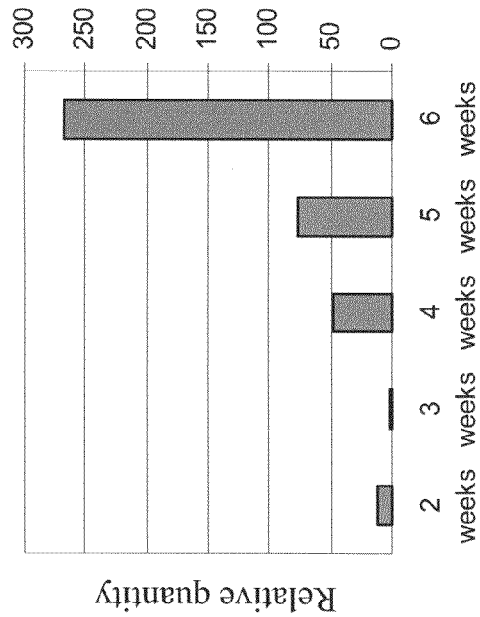
Figure 1E:
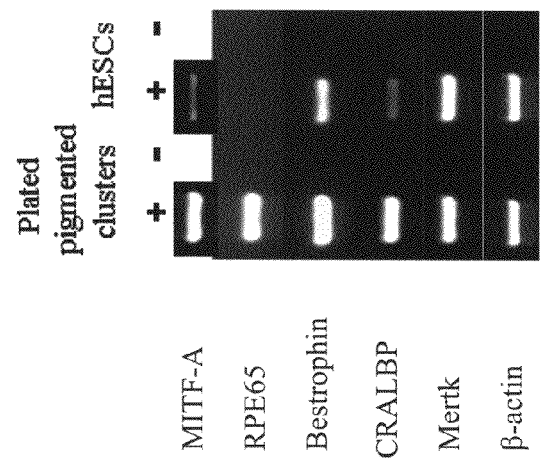

Differentiation of hESCs toward an RPE fate was examined by culturing them as free-floating clusters in KOM with or without NA (without providing spontaneously differentiating clusters as controls). After 6 weeks of differentiation, the level of expression of markers of RPE cells, MiTF-A and RPE65, was significantly enhanced in the presence of NA, as determined by Real-time RT-PCR (FIGS. 1A, and 1B; respectively). The expression of MiTF-A increased nearly two-fold in the presence of NA, while the expression of RPE65 increased nearly 30-fold. Since most pigmented cells co-expressed MITF-A (FIG. 8C), it appeared that in the presence of NA there was a significant and prominent increase in the level of expression of RPE65 per pigmented cell. Thus, in addition to its inductive effect towards RPE fate, NA also promoted the maturation of the RPE cells and had an effect on the phenotype of the cells. Q-PCR analysis at sequential time points between 2 and 6 weeks showed an increase in MiTF-A and RPE65 expression levels (FIGS. 1C and 1D, respectively), in the presence of NA. The expression of the markers was up-regulated after four weeks of differentiation, and the levels of expression continued to increase during the following four weeks (final two weeks not shown). Similar increased expression of the RPE markers Bestrophin, CRALBP and Mertk was shown by RT-PCR analysis of cells in plated, pigmented clusters (FIG. 1E).

Figure 9B:
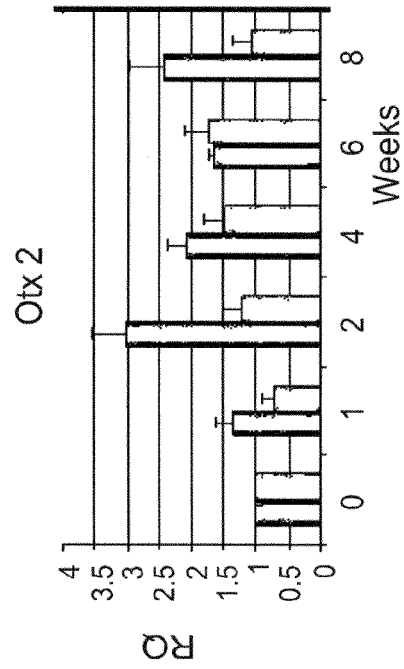
Figure 9D:
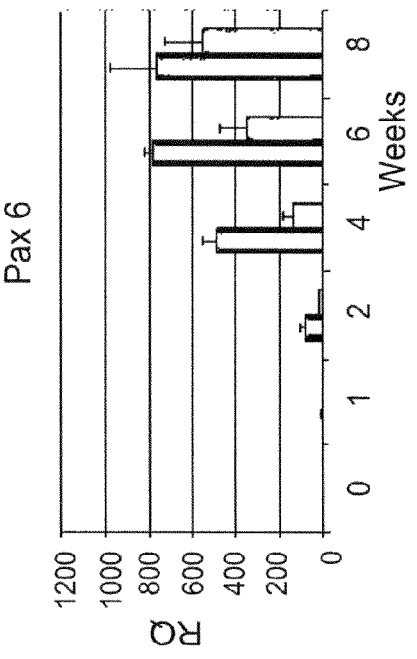
Figure 9A:
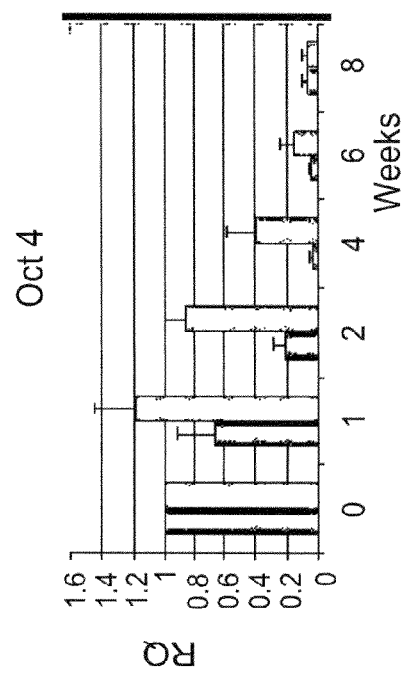
Figure 9C:
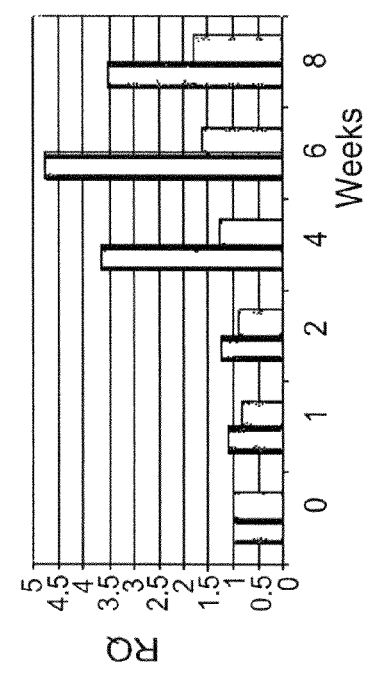
Figure 9E:
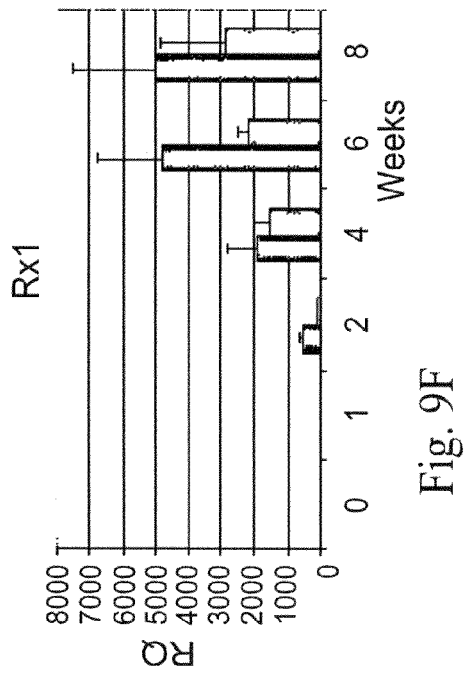
Figure 9F:
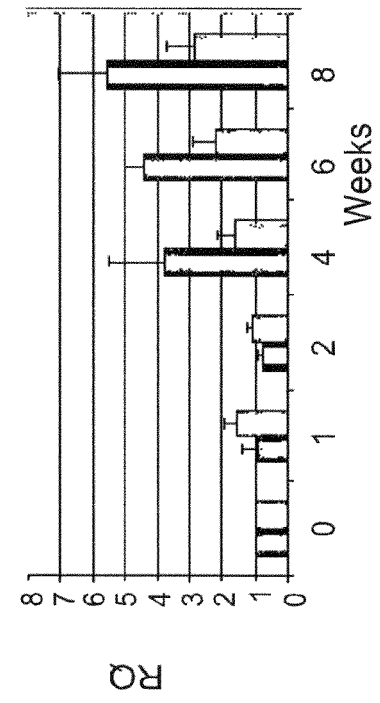
Figure 9G:
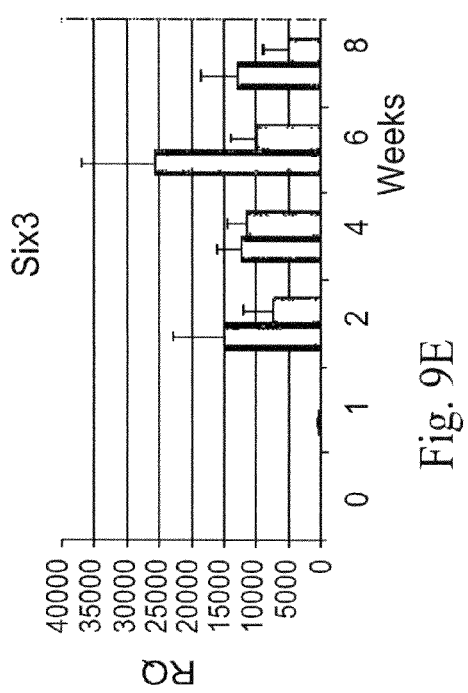

In order to find whether the development of RPE cells in vitro recapitulates the key developmental steps of RPE in vivo, time course experiments were performed including analyses of the expression within the hESC clusters of key markers during RPE development. Clusters differentiating in the presence or absence of NA were analyzed by Real-time PCR for the expression of markers of undifferentiated hESCs, early neural differentiation, retinal and RPE development (FIGS. 9A-9L). First it was demonstrated that the expression of Oct4 (FIG. 9A), a marker of undifferentiated hESCs, declined more rapidly during differentiation in the presence of NA. In accordance, FACS analysis demonstrated that the expression of TRA-1-60, a surface membrane marker of undifferentiated cells, also declined more rapidly in NA treated samples (FIG. 9M). Thus, differentiation in the presence of NA may be used to eliminate undifferentiated cells from the culture and may aid in avoiding teratoma tumor formation after transplantation.

In addition, NA treatment enhanced the process of early neural differentiation. In the presence of NA, the expression of transcripts of the early neural markers Otx2 (FIG. 9B), Pax6 (FIG. 9D) and Musashi (FIG. 9C) was significantly increased after 2, 2-6 and 4-6 weeks of differentiation, respectively. Similar results were demonstrated at the protein level by FACS analysis of the expression of PSA-NCAM, a marker of neural precursors (FIG. 9O). After 4 weeks of differentiation with NA, 81.4±6.3% of the cells expressed PSA-NCAM as compared to 14.4±5.9 in control clusters. Indirect immunofluorescence staining confirmed that at 4 weeks, the majority of cells within the NA-treated clusters acquired a neural phenotype and expressed PSA-NCAM (74.2±4.1%), nestin (55.9±10.1%), and Musashi (71.4%; FIG. 9N).

The expression of transcripts of Rx1 and Six3 (FIGS. 9F and 9E, respectively), which are key regulatory genes of retinal specification and morphogenesis, was demonstrated after 2 weeks of differentiation. NA treatment increased the expression of these genes.

Figure 9H:
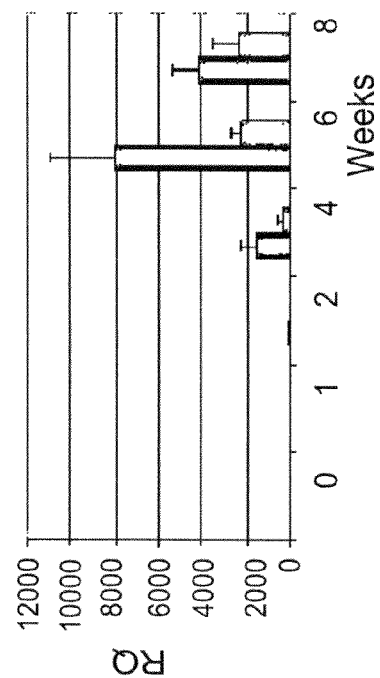

In the presence of NA the expression of transcripts of the early RPE marker, MiTF A was induced after 4 weeks of differentiation (FIG. 9H). The expression of markers of more mature RPE, Bestrophin and RPE65 was mainly up regulated after 4 and 8 weeks, respectively (FIGS. 9J and 9I, respectively). The expression of these transcripts was also higher in NA-treated cultures as compared to spontaneously differentiating hESC clusters as controls (FIGS. 9I, and 9J). The expression of RPE65 was augmented by more than a 100 folds further confirming that in addition to inductive effect NA also had an effect on the phenotype of the cells.). To rule out that the pigmented cells that were obtained are not neural crest-derived melanocytes, the expression of Sox10 was demonstrated, which is a developmental marker of these cells, was low compared to control cells of the M51 melanoma cell line and not dependent on NA supplementation. Thus the cultures were not comprised of melanocytes. Thus, it was concluded that NA promotes the induction of differentiation toward an RPE fate.

NA treatment also increased the expression of Chx10 which regulates the proliferation of neural retina retinal progenitors and of Crx, the marker of photoreceptor progenitors (FIG. 9K).

In summary, it was concluded by the inventors that the RPE differentiation process within the hESC clusters went through steps similar to authentic RPE development in vivo and was augmented by NA. Furthermore, NA had an effect on the phenotype of the RPE cells that were obtained. These cells were different from RPE cells that are obtained after spontaneous differentiation and expressed markers of mature RPE cells at significant higher levels.

NA Shows an Inductive Effect Regardless of Culture Medium

Figure 2A:
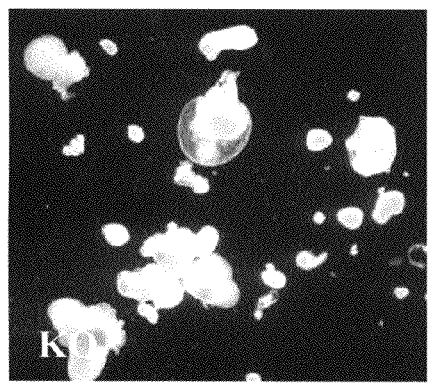
FIGS. 2A-2F: The RPE differentiation inductive effect of NA is not dependent on a specific medium composition. Dark field micrographs of hESC clusters differentiating 12 weeks in KO medium (FIG. 2A) or in Neurobasal medium supplemented with N2, which is substituted after 1 week with DMEM/F12 supplemented with B27 (NN medium) (FIG. 2C). In both media NA augmented the differentiation towards pigmented cells (FIGS. 2B, D) though the size of the differentiated hESC-clusters and their total number was smaller with NN medium (white arrows mark to pigmented areas within differentiating clusters). At the RNA level, in both media, NA supplementation enhanced the level of expression of MiTF-A and RPE65 (FIGS. 2E, and F; respectively).
Figure 2B:
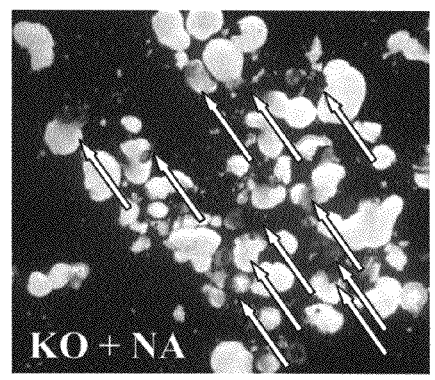
Figure 2C:
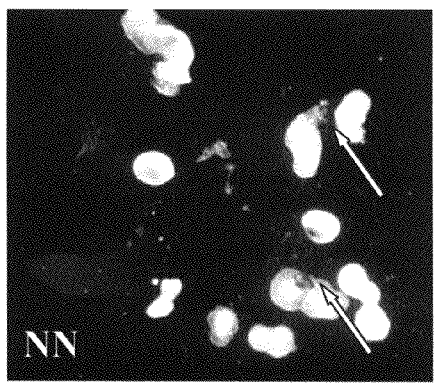
Figure 2D:
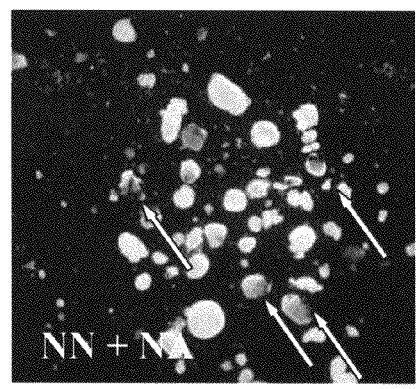
Figure 2E:
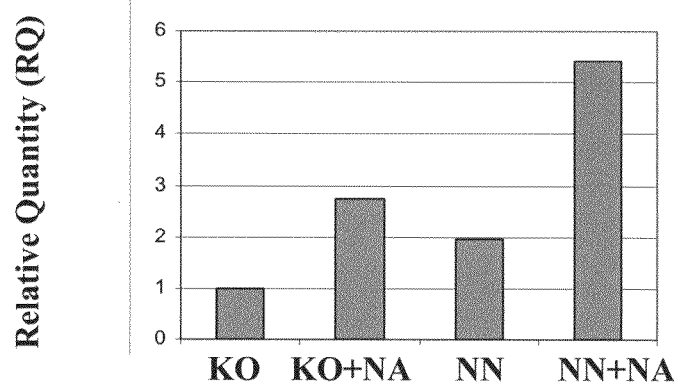
Figure 2F:
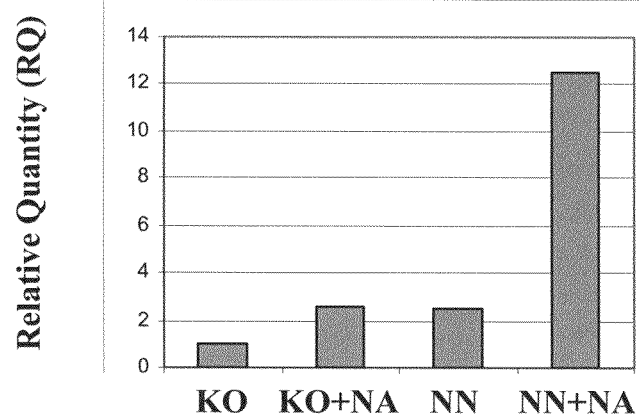

NA supplementation increased pigmentation in differentiated cells cultured in both KO medium and NN/DMEM medium for 12 weeks, as shown in dark field micrographs of clusters of differentiating hESCs (FIGS. 2A-2D). In NN medium that was further replaced after a week by DMEM/F12-B27 (NN/DMEM), as compared to KO medium, in the presence of NA, the percentage of pigmented hESC clusters from the total number of clusters was higher, although their size and total population numbers relative to clusters cultured in KO medium were smaller. RT-PCR analysis showed that NA supplementation enhanced the expression of MiTF-A approximately 3-fold in KOM and approximately 2.5-fold in NN/DMEM medium (FIG. 2E). The expression of RPE65 was approximately doubled in KOM, and increased nearly 6-fold in NN/DMEM medium, with supplementation of NA versus without NA (FIG. 2F). Thus, the differentiation-inductive effect of NA is shown in differentiated RPE cells regardless of the medium in which hESCs are cultured and differentiation occurs.

The Effect of Members of the TGFβ Superfamily on SC Differentiation

First analyzed was the expression of activin receptors as well as activin A in 2 weeks old clusters. Analysis was performed at this time point since the expression of early eye field markers is emerging at this time and therefore the differentiating cells are probably at a developmental stage parallel to early optic vesicle. It was demonstrated that the expression of the receptors ACTRIB and ACTRIIB was high in the presence of NA in comparison to lack or minor expression when the cells were differentiating without NA (FIG. 11G). Thus NA had an effect on the phenotype of cells differentiating in its presence.

Figure 4B:
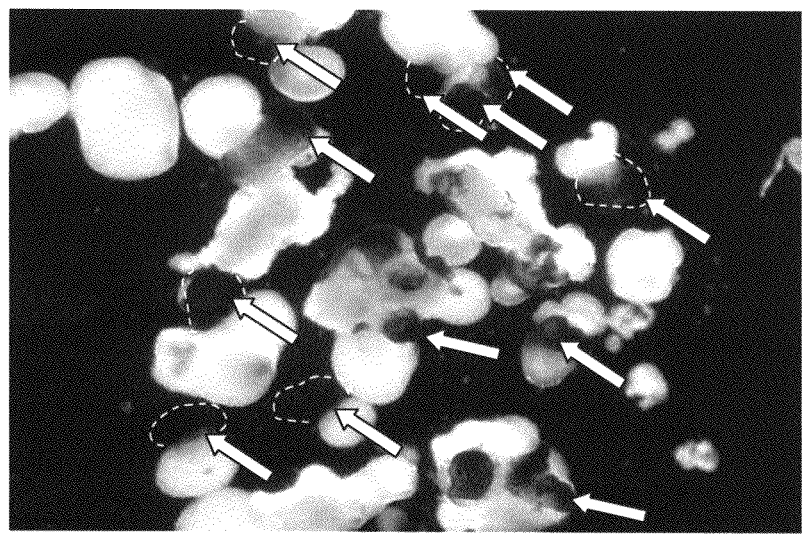

Activin A was found to augment differentiation towards RPE fate. Dark field micrographs of hESC-derived clusters differentiating for 4 weeks showed the appearance of pigmented cells at this early stage in the presence of activin (FIG. 11A) It was further shown that in the presence of NA, activin A significantly augmented the differentiation of hESCs towards RPE cells (FIGS. 4A-4B, and 11B-11C). The percentage of clusters that included pigmented cells (50.7±6.5_vs 17.7±3.2), as well as the percentage of pigmented cells from the total number of cells (9.9±1.4 vs 2.4±1.2), was significantly higher when differentiation was induced in the presence of activin A as compared to the control cultures supplemented with NA without activin A (FIGS. 11H and 11I). This result was confirmed with RT-PCR, which showed that activin A treatment significantly increased (over five-fold and over four-fold, respectively) the expression of the markers RPE65 (FIG. 4D) and Bestrophin (FIG. 4E) which are specific to mature RPE-cells. Furthermore, the morphological characteristics of clusters of pigmented cells that developed in the presence of activin A were different. Their pigmentation was darker and they displayed a very clear demarcation from surrounding non-pigmented cells (FIG. 4B). The expression of MiTF-A, a marker which appears earlier during RPE development was not affected by supplementation with activin A. Thus, activin A, which is a member of the TGFβ superfamily of growth factors, augments the differentiation of hESCs into RPE cells. The supplementation of the activin inhibitor, SB431542, significantly decreased the appearance of pigmented clusters under these conditions (FIGS. 11E, and 11H). The effect of activin A on RPE differentiation was studied in various concentrations. The effect was found to be dose dependent with optimal augmenting effect at 140 ng/ml on the percentage of pigmented cells and the expression of RPE markers, Bestrophin (FIG. 11K) and RPE65 (FIG. 11L). In most of the experiments activin A was supplemented for two weeks (weeks 3-4) after the clusters have already differentiated for 2 weeks, since we found that application at this time period was optimal for enhancing RPE differentiation. Given the observation that the expression of markers of early eye development also began after 2 weeks of differentiation (FIGS. 9A-9L), it appeared that activin augmented the process of eye and RPE development. Moreover, since the percentage of pigmented cells increased by 5-6 folds in the presence of activin A, while the expression of markers of mature RPE cells such as bestrophin increased by about 10 folds, it appears that activin A had an effect on the maturity and phenotype of the cells in addition to its inductive effect. This was supported by the morphological appearance of pigmented cells that were obtained in the presence of activin A as they were darker and with sharp demarcation from surrounding cells.

Q-PCR time-course analysis of the effect of 2 weeks activin A treatment on gene expression showed that activin A significantly increased the expression of the retinal progenitor markers Rx1 and Chx10 as well as the RPE marker Bestrophin. At 4 weeks of differentiation activin A treatment also increased the expression level of total MiTF-isoforms (FIGS. 11M-11P).

Figure 5E:
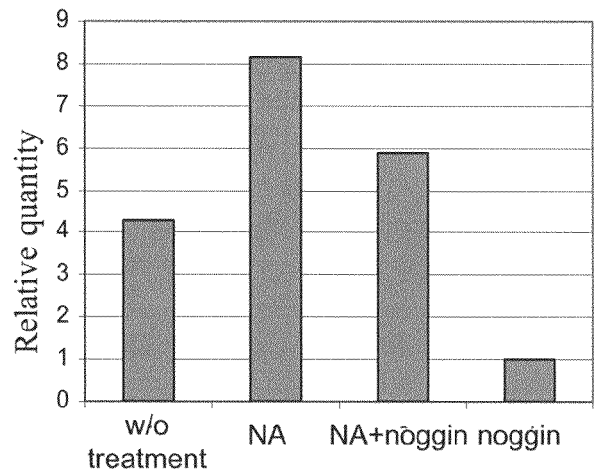
Figure 5F:
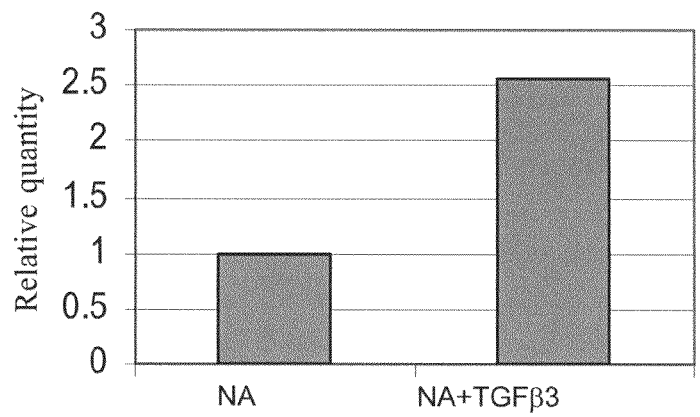
Figure 5G:
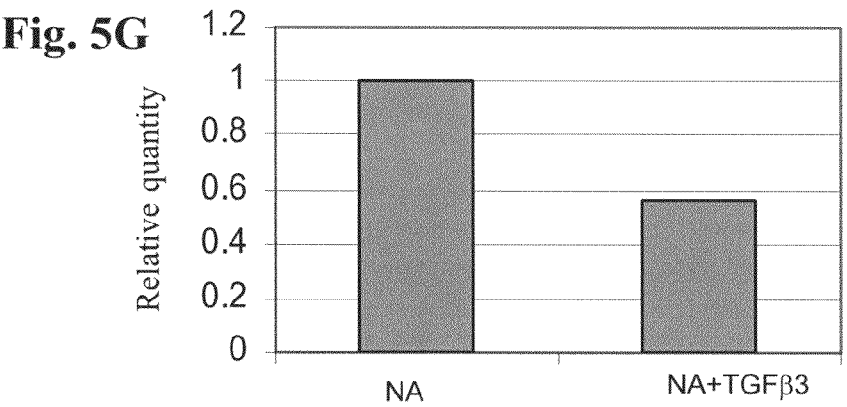

The inductive effect of activin A on retinal and RPE differentiation was observed also with other members of the TGFβ superfamily. Treatment of differentiating clusters with TGFβ3 significantly augmented the expression levels of transcripts of MiTF-A, which plays a key role in RPE development in vivo (FIG. 5F). Furthermore, treatment with TGFβ1, which is another member of the TGFβ superfamily also significantly enhanced the appearance of clusters harboring pigmented cells (FIGS. 11D, and 11H). In contrast, differentiation in the presence of NA and basic FGF (bFGF) instead of factors from the TGFβ superfamily abolished the appearance of pigmented cells (FIG. 11F).

In addition, it was shown that bone morphogenetic proteins (BMPs), which belong to a second sub-family of the TGFβ superfamily, play a role in RPE differentiation of hESCs. As shown in dark field micrographs, in the presence of the BMP antagonist noggin, differentiation of hESC clusters into pigmented RPE cells was blocked (FIG. 5D). Differentiation into pigmented cells was blocked with supplementation of noggin even when the medium was also supplemented with NA (FIG. 5C). At the RNA level, Real-Time RT-PCR demonstrated that noggin significantly reduced the expression of MiTF-A in both the presence and absence of NA in the culture medium (FIG. 5E). Thus, BMPs play a role in inducing differentiation of hESCs to RPE cells.

Figure 6A:
FIGS. 6A-6P: Survival and integration of transplanted hESC-derived RPE cells in rat eyes. Following intraocular transplantation of hESC-derived RPE cells, the pigmented cells could be readily identified in vivo in the eyes of albino rats (FIGS. 6A, 6B). Following enucleation of the eye (FIG. 6B) and removal of the cornea and lens, the main graft as well as additional dispersed pigmented spots could be seen (FIG. 6C). In histological sections, grafts that included dark pigmented cells which also co-express GFP could be identified (FIG. 6D-6G), attesting to the fact that the cells were hESC-derived. Transplanted cells could be found in the intravitreal area, between the retina and lens (FIG. 6H), in the retina (occasionally protruding into the vitreous along the tract of injection) (FIG. 6I), and also in the subretinal space (FIGS. 6I, 6O, 6P). Transplanted hESC-derived RPE cells (pigmented cells marked with arrows) integrated into the RPE layer of albino rats (FIG. 6J). Pigmented cells were not observed in the RPE layer of control non-transplanted eyes. Within grafts, immunostaining with ZO-1 (FIG. 6K-6N) showed that there were tight junctions between transplanted GFP+hESC-derived cells. Such junctions are characteristic of RPE cells. Following transplantation into the subretinal space of RCS rats with RPE dysfunction and retinal degeneration, relative preservation of the photoreceptor layer could be seen in proximity to the graft (FIG. 6O; the area within the rectangle is marked by an asterisk, and enlarged in FIG. 6P), as compared to areas distant from the graft (marked by arrows). Note the large transplanted hESC-derived RPE cells with polygonal shape and cobblestone-like appearance (FIG. 6P) (asterisk). In all cases shown here, RPE cells were derived from hESCs without presence of Activin-A.
Figure 6B:
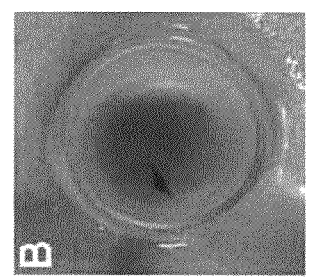
Figure 6C:
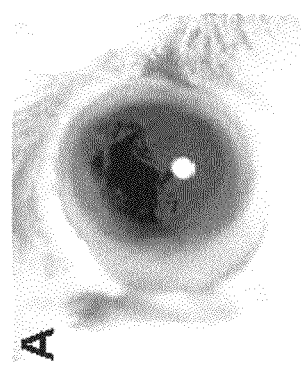
Figure 6D:
Figure 6E:
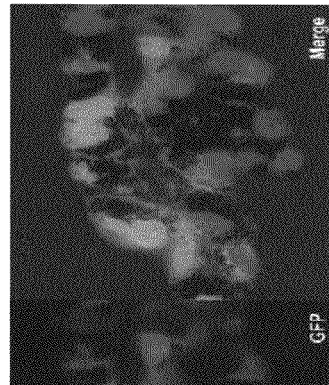
Figure 6F:
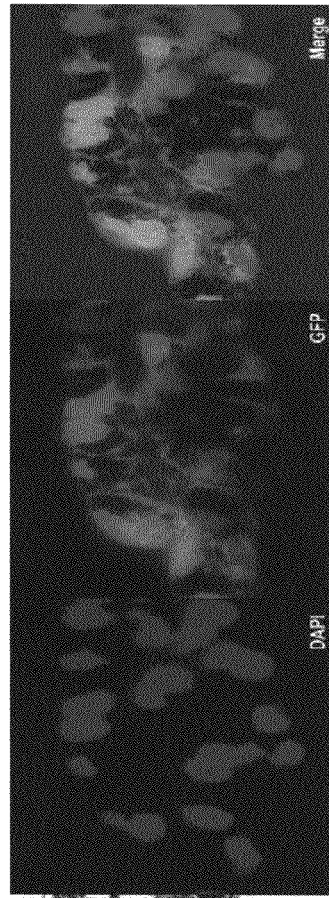
Figure 6G:
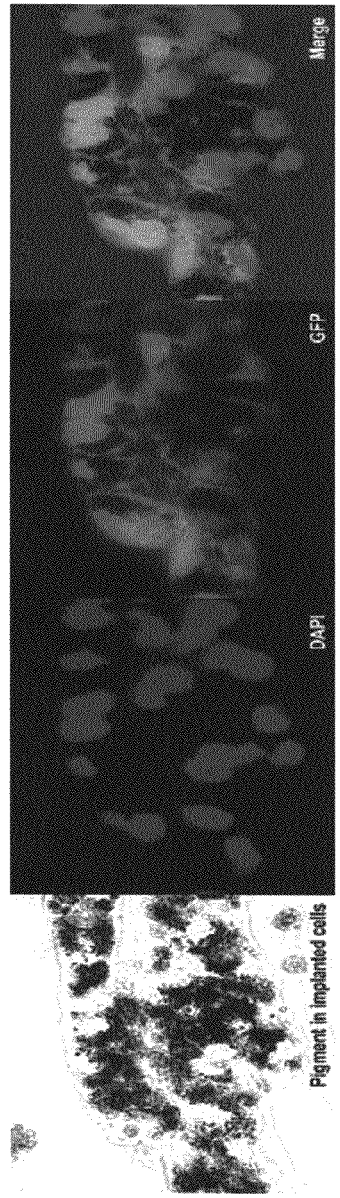
Figure 6H:
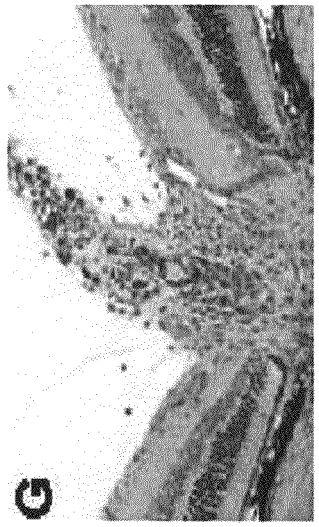
Figure 6I:
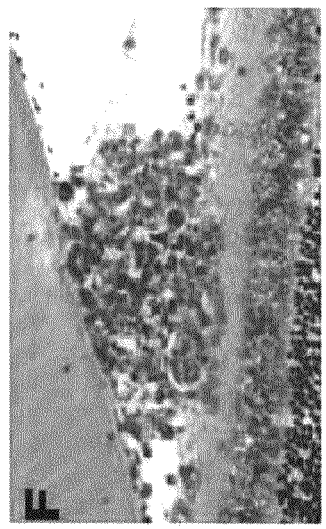
Figure 6J:
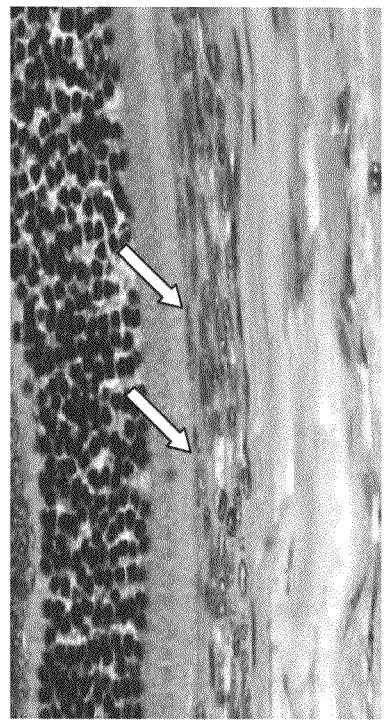

Differentiated RPE Cells Derived from hESCs May be Used for Intraocular Transplantation Enriched populations of hESC-derived RPE cells engineered to express eGFP were initially transplanted into the vitreous and subretinal spaces of albino rats, to facilitate localization of the pigmented cells. Following intraocular transplantation, the transplanted pigmented cells could be readily identified in vivo (FIGS. 6A and 6B). Following enucleation of the eye shown in FIG. 6B, removal of the cornea and lens and isolation of the retina, the retina showed the main graft as well as additional dispersed pigmented cells (FIG. 6C). In histologic sections, grafts that included viable pigmented transplanted cells which also expressed GFP were present (FIGS. 6D-6G). Transplanted cells could be found in the vitreal space, in the retina, along the tract of injection, and also in the subretinal space (FIGS. 6H, 6I, 6O, 6P). Transplanted RPE cells also migrated from subretinal grafts and integrated within the RPE layer of host rats (FIG. 6J). In the grafts, tight junctions, which are characteristic of RPE cells, were formed, as shown by expression of the tight junction marker ZO-1 in transplanted eGFP-positive cells (FIG. 6K-6N). Cells within the grafts also maintained the expression of RPE65, Bestrophin, and MiTF-A.

hESC-Derived RPE Cells Survive, Integrate and Maintain Characteristics of Differentiated RPE Following Transplantation into the Subretinal Space of RCS Rats The main body of transplantation experiments were performed in RCS rats which manifest an RPE and retinal degeneration caused by a mutation in the mertk gene, in an attempt to examine whether delivery of hESC-derived RPE cells can modulate the course of disease.

Figure 12A:
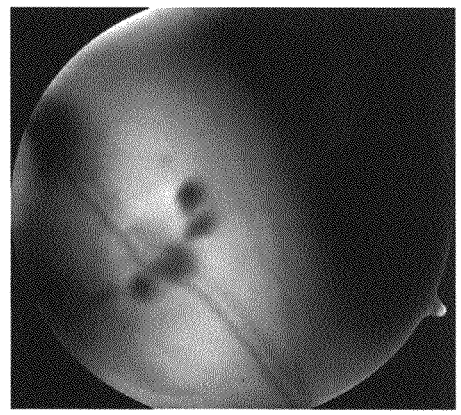
FIG. 12A-12E: RPE cells derived from hESCs treated by NA and Activin A survive following sub-retinal transplantation in dystrophic RCS rat eyes. Clusters of pigmented cells could be readily identified in-vivo in the eyes of RCS rats using fundus imaging systems (FIGS. 12A-12C); Fundus photo (FIG. 12A) and red-free photo (FIG. 12B) which showed the subretinal location of the grafts (note retinal vessels coursing over the pigmented areas). The hESC-derived, GFP-expressing cells can be seen to emit fluorescence when fluorescein excitation and emission filters were used (FIG. 12C). In eye cup preparations imaged ex-vivo in a fluorescence microscope (FIGS. 12D-12E), large clusters of subretinal GFP-positive cells can be seen (FIG. 12D) as well as multiple, dispersed smaller clusters (FIG. 12E).
Figure 12B:
Figure 12C:
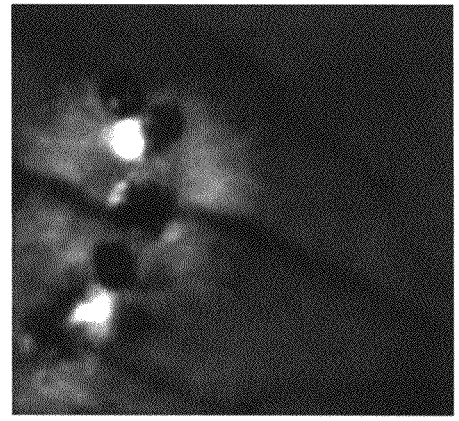
Figure 12D:
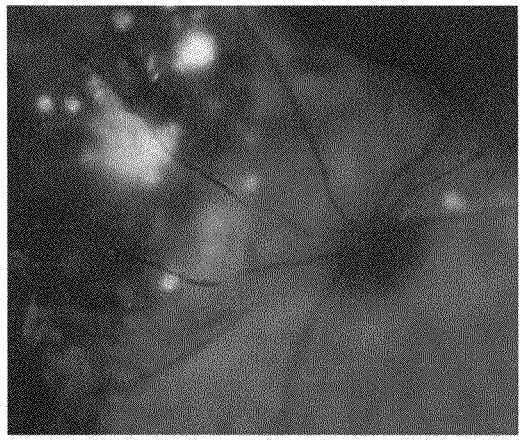
Figure 12E:
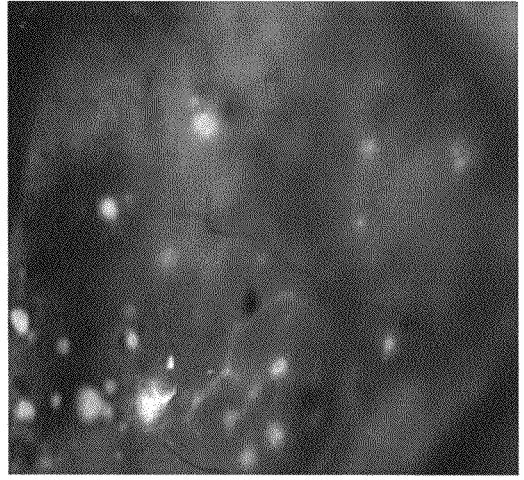

The transplanted pigmented cells could be readily identified in-vivo in the eyes of RCS rats using standard fundus imaging systems (FIGS. 12A-12C). The hESC-derived, GFP-expressing cells can be seen to emit fluorescence when fluorescein excitation and emission filters are used (FIG. 12C). In eye cup preparations imaged ex-vivo in a fluorescence microscope (FIGS. 12D-12E), large clusters of subretinal GFP-positive cells can be seen (FIG. 12D) as well as multiple, dispersed smaller clusters (FIG. 12E).

Figure 13A:
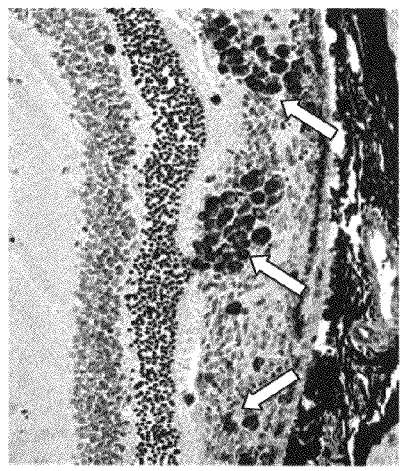
FIG. 13A-13F: Histologic appearance of sub-retinal hESC-derived, Activin-A-treated RPE cell grafts in RCS rat eyes. Histologic sections stained by hemotoxylin and eosin (FIGS. 13A, and 1B) showed the subretinal and occasionally intra-retinal location of transplanted hESC-derived pigmented cells, which appeared in clusters or as isolated cells (arrows). Immunostaining with GFP (FIGS. 13C-13F) confirmed that the cells are indeed hESC-derived. Grafts were often quite large and dispersed (FIGS. 13C, 13E), and pigmented cells co-expressing GFP can be clearly seen (FIGS. 13D, 13F). Note GFP-positive pigmented cells integrating within the host RPE layer (FIG. 13D, arrow).
Figure 13B:
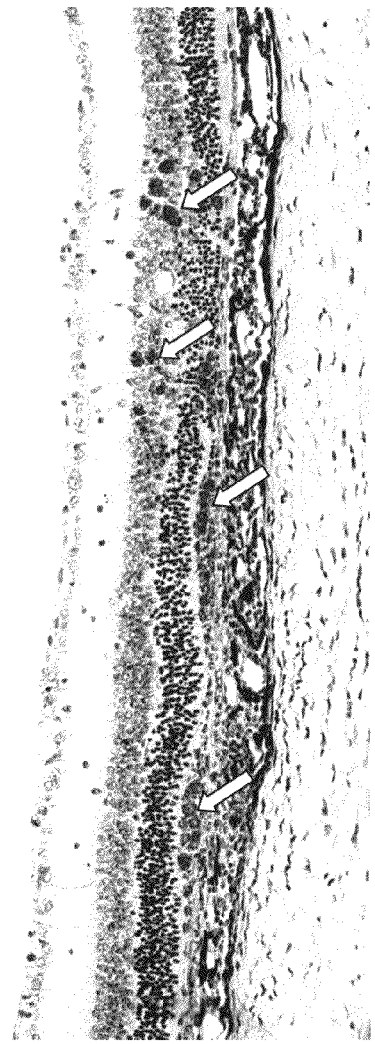
Figure 13C:
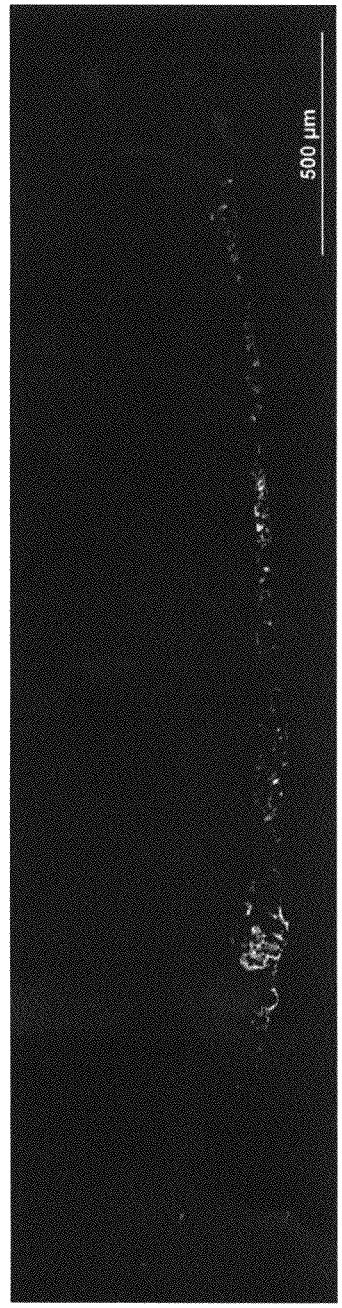
Figure 13D:
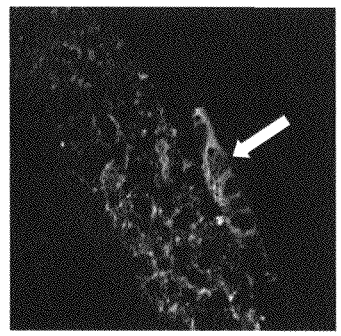
Figure 13E:
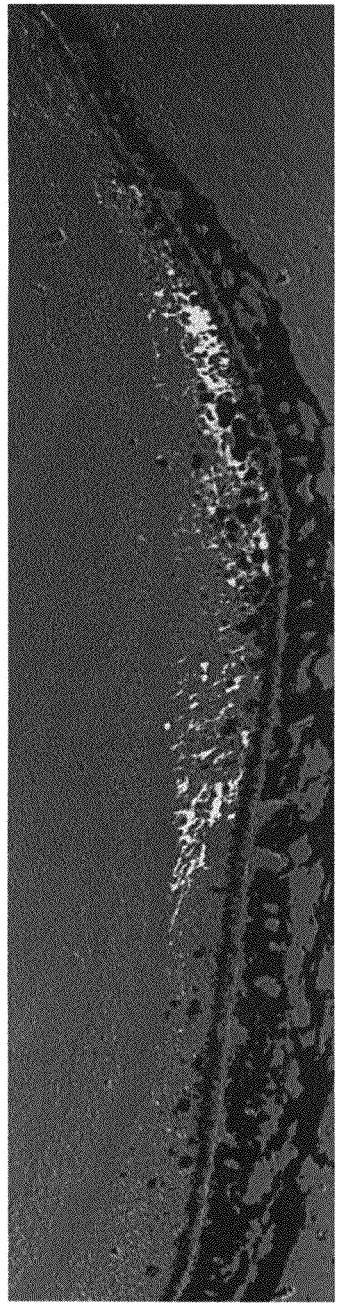
Figure 13F:
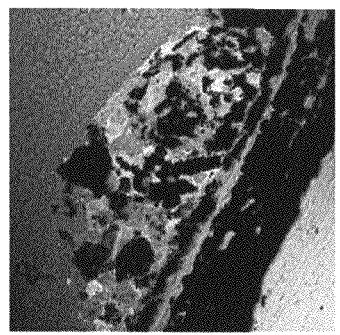
Figure 14C:
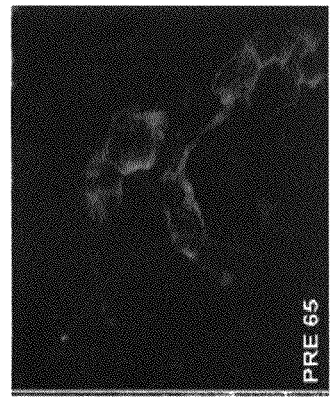
Figure 14B:
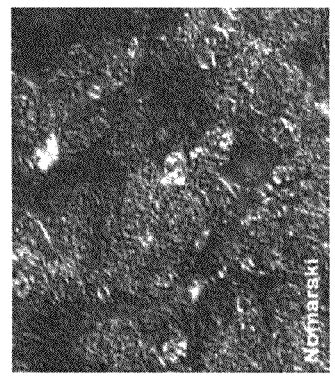
Figure 14A:
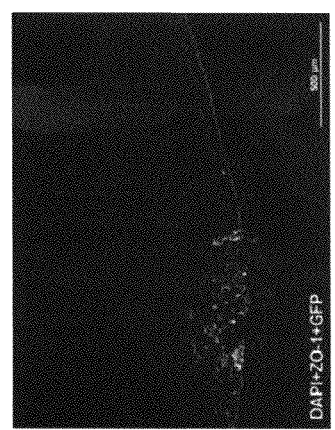
FIG. 14A-14O: Transplanted hESC-derived pigmented cells express markers of mature RPE. Immunostaining revealed that large numbers of transplanted cells within grafts express proteins which are characteristic of mature RPE cells, including the RPE-specific markers RPE65 (FIGS. 14A-14E) and Bestrophin (FIGS. 14F-14J) as well as the tight-junction marker ZO-1 (FIGS. 14K-14O).
Figure 14E:
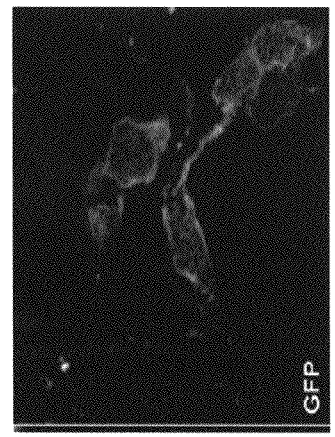
Figure 14D:
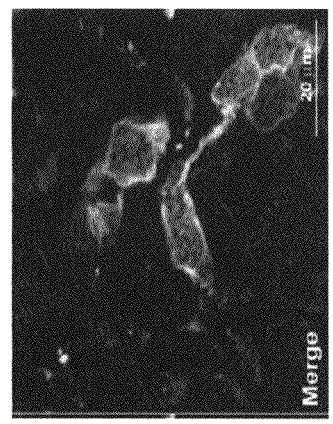
Figure 14M:
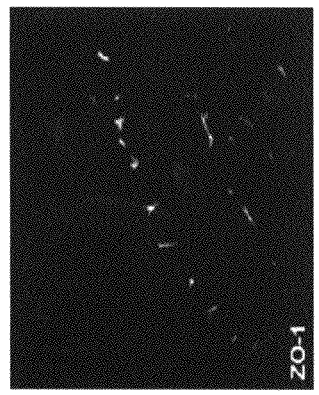
In FIG. 14M, note that the host RPE stains for ZO-1 (dashed arrow) while it is GFP-negative in FIGS. 14N, 14O (corresponding area is dark) as opposed to the ZO-1 positive hESC-derived cells (full arrow in FIG. 14M) which do co-express GFP (FIGS. 14N, 14O).
Figure 14L:
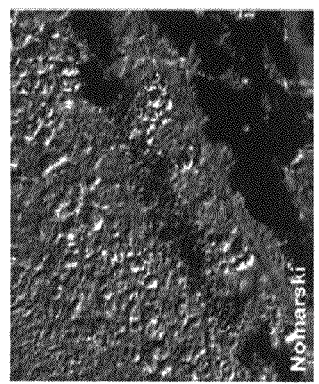
Figure 14K:
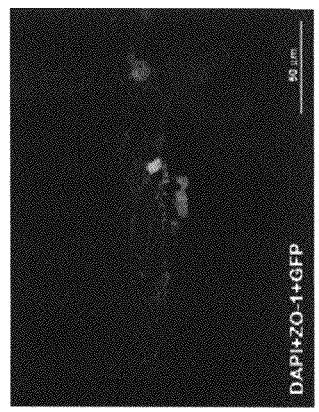
Figure 14O:
Figure 14N:
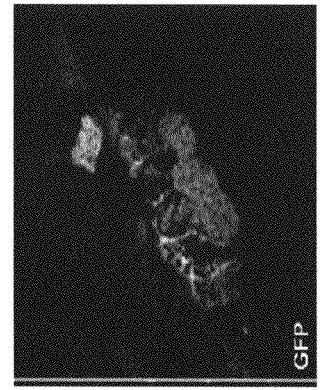

Histologic and immunohistochemical evaluation confirmed the in-vivo and ex-vivo macro observations. The transplanted cells survived and integrated in the subretinal space, and maintained expression of proteins that characterize and are often specific to mature RPE (FIGS. 13 and 14). It is important to note that no significant inflammation or immune reaction was present, and no tumors or teratomas were observed in over 100 transplanted eyes. Sections stained by hemotoxylin and eosin (FIGS. 13A and 13B) show the sub-retinal and occasionally intra-retinal location of transplanted hESC-derived pigmented cells, which appeared in clusters or as isolated cells (arrows). Immunostaining with GFP (FIGS. 13C-13F) confirmed that the cells are indeed hESC-derived. Grafts were often quite large and dispersed (FIGS. 13C, and 13E), and pigmented cells co-expressing GFP were clearly seen (FIGS. 13D, and 13F).

Figure 7:
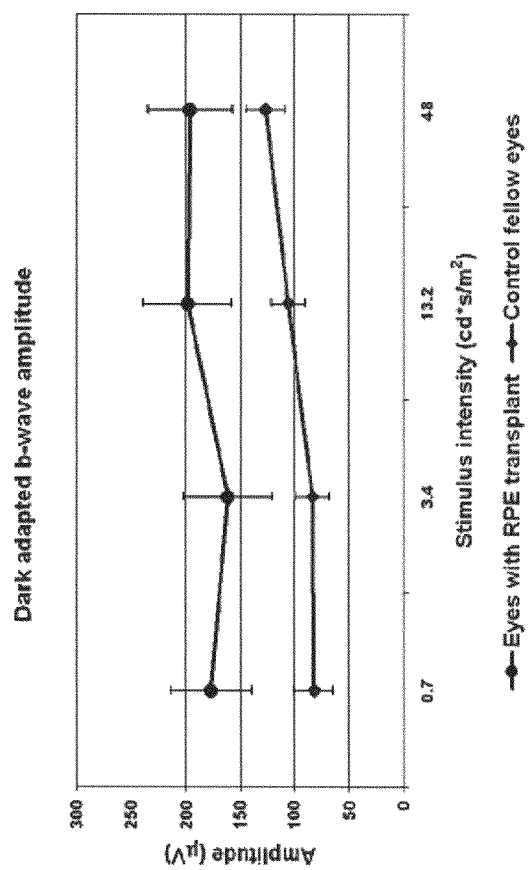
FIG. 7: Electroretinographic recordings show that transplantation of hESC-derived RPE cells provides rescue of retinal function in the eyes of dystrophic RCS rats. Full field ERG responses are higher in RCS rat eyes following transplantation of RPE cells derived from hESC compared to fellow non-transplanted control eyes (n=11 rats). RPE cells used in these experiments were derived without addition of Activin A to the culture medium. b-wave amplitudes of the dark-adapted mixed cone-rod responses to four stimuli of increasing intensity are shown.

Immunostaining revealed that large numbers of transplanted cells within grafts express proteins which characterize mature, differentiated RPE cells (FIG. 14). This included expression of the RPE-specific markers RPE65 (FIGS. 14A-14E) and Bestrophin (FIGS. 14F-14J). The cells were also capable of forming tight junctions (FIGS. 14K-14O), which is an important function of RPE cells and essential for maintaining the blood-retinal barrier. Left-most panel in each row shows low-magnification fluorescent image of grafts co-expressing GFP and the relevant marker. High magnification confocal images in each row show pigment (by Nomarski optics) as well as co-expression of GFP and the different markers at the single-cell level.

heSC-Derived RPE Cells Provide Functional and Structural Retinal Rescue in Dystrophic RCS Rats In the RCS rat model of retinal degeneration, retinal function is usually severely impaired by 2-3 months of age. Structurally, corresponding loss and thinning of the retinal outer nuclear layer (ONL) occurs and it is often reduced to less than 1-2 rows of photoreceptor nuclei at this age. In eyes transplanted with hESC-derived RPE cells, electroretinographic recordings revealed significant relative preservation of retinal function as compared to control untreated or medium-injected eyes (FIG. 7 and FIG. 15).

Figures 15A, 15B:
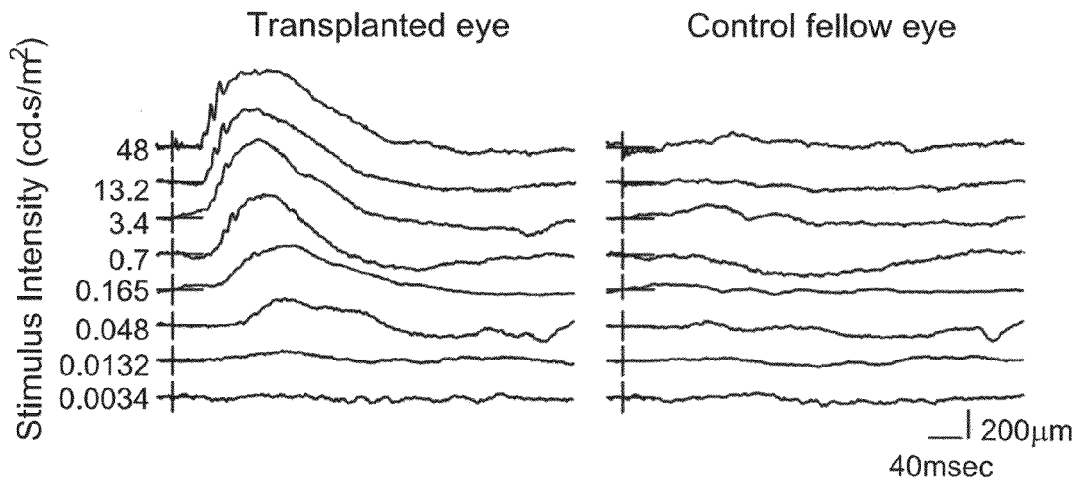
FIG. 15A-15C: Transplanted hESC-derived, Activin-A treated RPE cells provide functional rescue in the RCS rat retinal degeneration model. Full field ERG responses recorded at the age of 8 weeks were higher in RCS rat eyes following transplantation of activin-treated RPE cells derived from hESC as compared to fellow non-transplanted control eyes as well as compared to eyes in which subretinal injection of medium alone was performed. Representative ERG responses to a series of white flashes of increasing intensity in the dark-adapted state are shown in a transplanted eye (FIG. 15A) versus its fellow control eye (FIG. 15B).
Figure 15C:
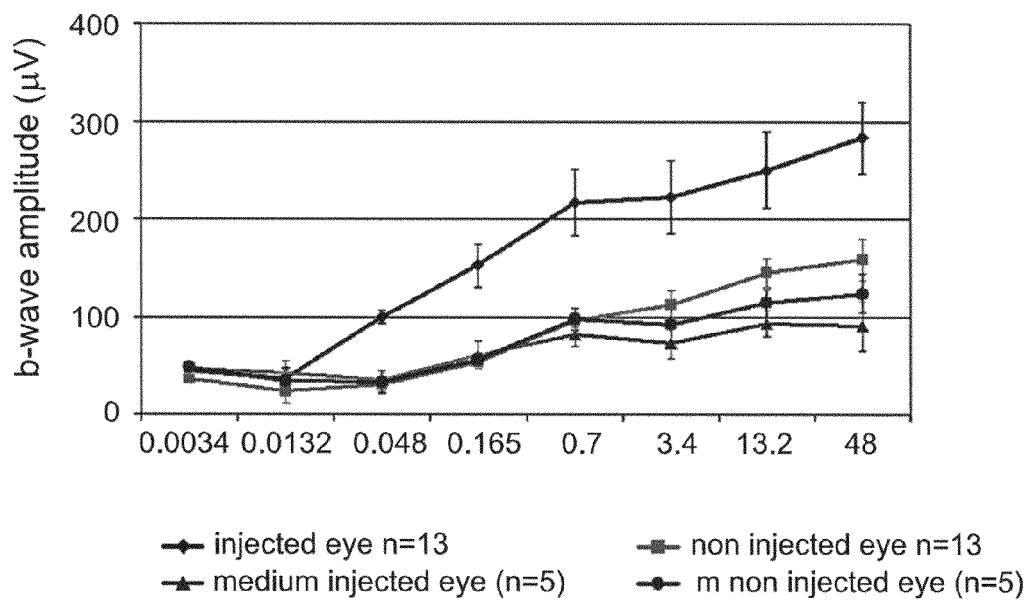

Representative ERG responses to a series of white flashes of increasing intensity in the dark-adapted (DA) state are shown in a transplanted eye (FIG. 15A) versus its fellow control eye (FIG. 15B). FIG. 15C shows the marked differences in mean amplitudes between transplanted eyes and the different groups of control eyes. At the highest intensity, mean DA b-wave amplitude in RPE-transplanted eyes was 283.3±37.5 (mean±SEM; n=13) versus 158.5±18.1 in fellow non-treated control eyes (n=13, p<0.01) and 89.9±14.4 in medium-injected eyes (n=5, p<0.01). It is important to note that there is a trend towards better preservation of retinal function following transplantation of Activin-A treated RPE cells (FIG. 15) as compared to the rescue effect achieved following transplantation of RPE cells derived without activin-A (FIG. 7).

Figure 16D:
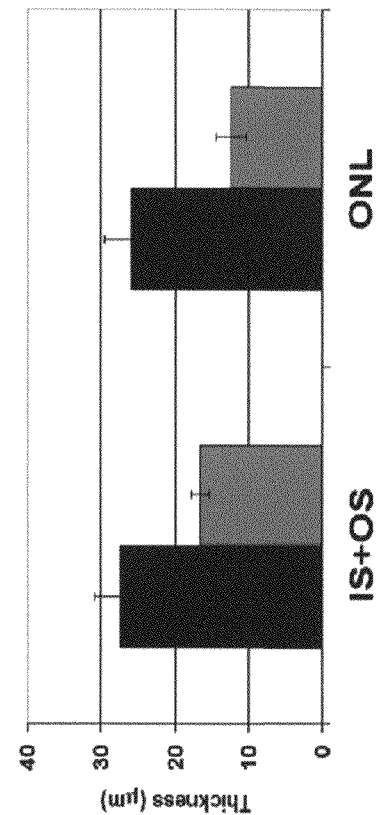
Figure 16C:
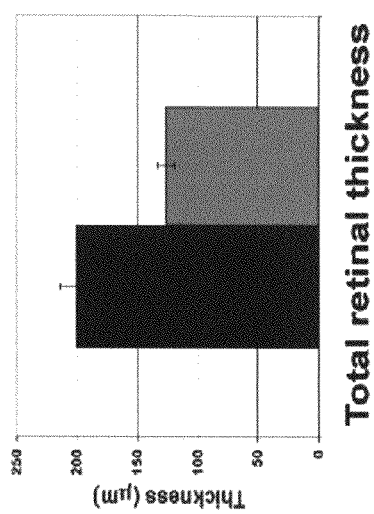

Qualitative as well as quantitative assessment of retinal structure corroborated the functional findings (FIG. 16). Relative preservation of the photoreceptor (ONL) layer and of the inner and outer photoreceptor segments (IS+OS) was observed in proximity to sub-retinal RPE grafts as compared with areas distant from the grafts (two examples shown in FIGS. 16A, 16B). Total retinal thickness (FIG. 16C) as well as ONL and IS+OS thickness (FIG. 16D) are significantly increased in vicinity to hESC-derived RPE grafts (black bars, mean±SEM, n=7) as compared to areas distant from grafts (gray bars). This type of structural rescue was observed only in proximity to sub-retinal and deep intra-retinal grafts, and not when grafts were exclusively intra-vitreal (not shown).

Transplanted hESC-Derived, Activin-A Treated RPE Cells Uptake Rhodopsin In-Vivo

Figure 17C:
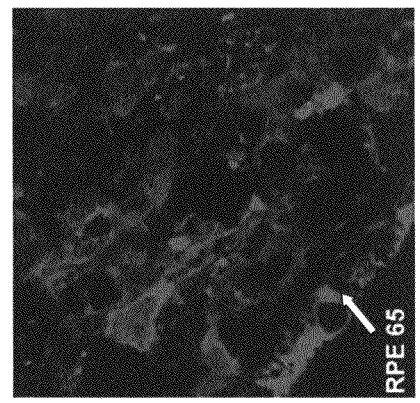
FIG. 17A-17E: Transplanted hESC-derived, Activin-A treated RPE cells uptake rhodopsin in-vivo. Confocal images of subretinal transplanted RPE cells show the co-localization of pigment, GFP, RPE65 and rhodopsin within the same single cells. The native RPE cells of the RCS rat express RPE65 (FIG. 17C, arrow) but do not express GFP (FIG. 17D, arrow) and contain minimal amounts of rhodopsin (FIGS. 17B, 17E).
Figure 17B:
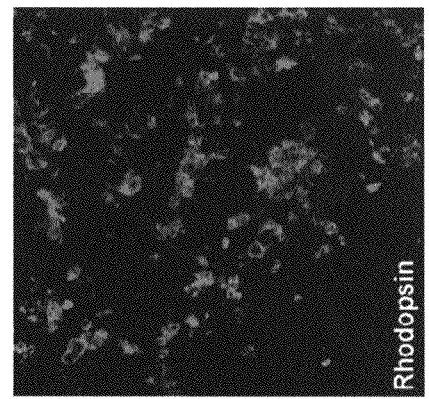
Figure 17A:
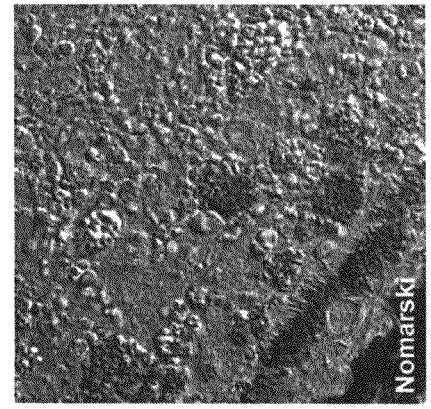
Figure 17E:
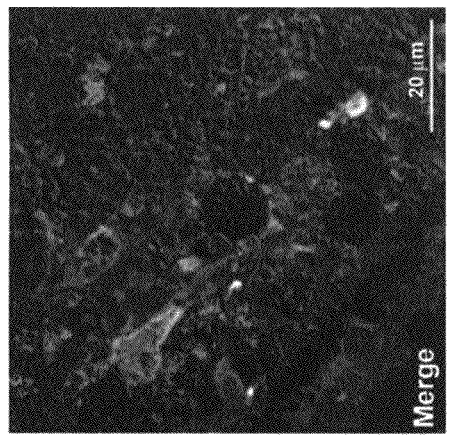
Figure 17D:
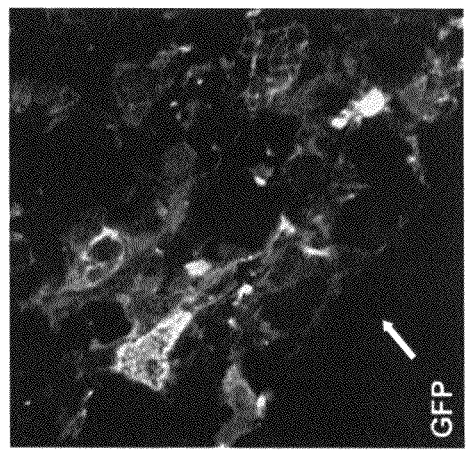

One of the key functions of healthy RPE is the uptake and recycling of shed photoreceptor outer segments, as part of the renewal process of the photoreceptor. Confocal images of subretinal transplanted RPE cells show the co-localization of pigment, GFP, RPE65 and rhodopsin within the same single cells. This suggested that the transplanted cells have the phenotype of mature RPE and are able to perform uptake of shed outer segments (which contain rhodopsin). Note that the native RPE cells of the RCS rat express RPE65 (FIG. 17C, arrow) but do not express GFP (FIG. 17D, arrow) and contain minimal amounts of rhodopsin (FIGS. 17B, 17E).

The above results thus provide evidence that hSCs derived RPE cells obtained by culturing in a culture system comprising a member of the TGFβ superfamily and preferably in the presence of NA can be utilized in vivo for transplantation to provide essentially fully functional RPE cells in the eye.

The invention claimed is:

1. A method for promoting directed differentiation of human pluripotent stem cells into retinal pigment epithelium (RPE) fate, the method comprising:
   (a) culturing human pluripotent stem cells in a medium supplemented with nicotinamide (NA) to generate differentiating cells; and subsequently
   (b) culturing said differentiating cells in a medium supplemented with activin A under conditions which induce said differentiating cells to differentiate into RPE cells.

2. The method of claim 1, wherein said culturing in said medium supplemented with NA is effected for at least two days prior to culturing in said medium supplemented with said activin A.

3. The method of claim 1, wherein said cells are cultured in a suspension.

4. The method of claim 1, wherein said human pluripotent stem cells are human embryonic stem cells.

5. The method of claim 1, wherein culturing said differentiating cells in said medium supplemented with nicotinamide is effected for about two weeks.

6. The method of claim 1, wherein culturing said differentiating cells in said medium supplemented with activin A in step (a) is effected for about two weeks.

7. The method of claim 1, wherein a concentration of said nicotinamide is about 10 mM.

8. The method of claim 1, wherein a concentration of said activin A is between 20-180 ng/ml.

9. The method of claim 1, wherein said medium supplemented with activin A is further supplemented with nicotinamide.

* * * * *

```
                              SEQUENCE LISTING

<160> NUMBER OF SEQ ID NOS: 12

<210> SEQ ID NO 1
<211> LENGTH: 38
<212> TYPE: DNA
<213> ORGANISM: Homo sapiens

<400> SEQUENCE: 1
gagccatgca gtccgaatga catggcaagc tcaggact                              38

<210> SEQ ID NO 2
<211> LENGTH: 40
<212> TYPE: DNA
<213> ORGANISM: Homo sapiens

<400> SEQUENCE: 2
gctgctggaa aggatttgag caggctccag ccagatagtc                            40

<210> SEQ ID NO 3
<211> LENGTH: 40
<212> TYPE: DNA
<213> ORGANISM: Homo sapiens

<400> SEQUENCE: 3
gaatttgcag gtgtccctgt atcctcctcg tcctcctgat                            40

<210> SEQ ID NO 4
<211> LENGTH: 40
<212> TYPE: DNA
<213> ORGANISM: Homo sapiens

<400> SEQUENCE: 4
agctgctgga gaatgaggaa caagaagggc ttgaccacat                            40

<210> SEQ ID NO 5
<211> LENGTH: 40
<212> TYPE: DNA
<213> ORGANISM: Homo sapiens

<400> SEQUENCE: 5
aagtgatgtg tgggcatttg tctaagggat cggttctcca                            40

<210> SEQ ID NO 6
<211> LENGTH: 42
<212> TYPE: DNA
<213> ORGANISM: Homo sapiens

<400> SEQUENCE: 6
aatgttgccg tgaagatctt cctgagaacc atctgttggg ta                         42

<210> SEQ ID NO 7
<211> LENGTH: 38
<212> TYPE: DNA
<213> ORGANISM: Homo sapiens

<400> SEQUENCE: 7
```

-continued

```
cacgtgtgag acagatgggg gcggttgtga tagacacg                        38

<210> SEQ ID NO 8
<211> LENGTH: 43
<212> TYPE: DNA
<213> ORGANISM: Homo sapiens

<400> SEQUENCE: 8
aaccatggct agaggattgg cctttcacct acacatccag ctg                  43

<210> SEQ ID NO 9
<211> LENGTH: 38
<212> TYPE: DNA
<213> ORGANISM: Homo sapiens

<400> SEQUENCE: 9
caccatcgag ctcgtgaagg agcccttgtc atggaagg                        38

<210> SEQ ID NO 10
<211> LENGTH: 38
<212> TYPE: DNA
<213> ORGANISM: Homo sapiens

<400> SEQUENCE: 10
cttgaagaag agacccgatc ttctgcacgc tccaccac                        38

<210> SEQ ID NO 11
<211> LENGTH: 39
<212> TYPE: DNA
<213> ORGANISM: Homo sapiens

<400> SEQUENCE: 11
ttcaccacca cggccgagct ctccttctgc atcctgtcg                       39

<210> SEQ ID NO 12
<211> LENGTH: 39
<212> TYPE: DNA
<213> ORGANISM: Homo sapiens

<400> SEQUENCE: 12
agccacatcg ctcagacacc gtactcagcg ccagcatcg                       39
```